(12) United States Patent
Kunding

(10) Patent No.: US 11,693,001 B2
(45) Date of Patent: Jul. 4, 2023

(54) FLOW SYSTEM AND METHODS FOR DIGITAL COUNTING

(71) Applicant: SELMA DIAGNOSTICS APS, Herlev (DK)

(72) Inventor: Andreas Hjarne Kunding, Herlev (DK)

(73) Assignee: Selma Diagnostics APS, Herlev (DK)

( * ) Notice: Subject to any disclaimer, the term of this patent is extended or adjusted under 35 U.S.C. 154(b) by 547 days.

(21) Appl. No.: 16/913,179

(22) Filed: Jun. 26, 2020

(65) Prior Publication Data

US 2020/0319178 A1 Oct. 8, 2020

Related U.S. Application Data

(62) Division of application No. 15/551,410, filed as application No. PCT/EP2016/074045 on Oct. 7, 2016, now Pat. No. 10,746,734.

(Continued)

(51) Int. Cl.
*G01N 33/543* (2006.01)
*B01L 3/00* (2006.01)
(Continued)

(52) U.S. Cl.
CPC ........ *G01N 33/54386* (2013.01); *B01L 3/502* (2013.01); *B01L 3/5088* (2013.01); *G01N 33/521* (2013.01); *G01N 33/54366* (2013.01); *G06M 11/00* (2013.01); *B01L 2200/142* (2013.01); *B01L 2300/0636* (2013.01); *B01L 2300/089* (2013.01);
(Continued)

(58) Field of Classification Search
CPC ........ G01N 33/54386; G01N 33/54366; B01L 3/502; B01L 2300/0636; B01L 2300/0816; B01L 2300/0819; B01L 2300/0877; B01L 2300/165; B01L 2400/049
See application file for complete search history.

(56) References Cited

U.S. PATENT DOCUMENTS 5,384,261 A 1/1995 Winkler et al.
5,412,087 A 5/1995 McGall et al.
(Continued)

FOREIGN PATENT DOCUMENTS

CN 101935703 A 1/2011
CN 102296116 A 12/2011
(Continued)

OTHER PUBLICATIONS

Méndez-Vilas et al., Ultrasmall Liquid Droplets on Solid Surfaces: Production, Imaging, and Relevance for Current Wetting Research, 2009, Nano Micro Small, vol. 5, No. 12, pp. 1366-1390 (Year: 2009).*

(Continued)

*Primary Examiner* — Melanie Brown
(74) *Attorney, Agent, or Firm* — Womble Bond Dickinson (US) LLP

(57) ABSTRACT

The present invention relates to methods and systems for testing for the presence of a material such as one or more analyte types within a sample and more particularly, for improved single enzyme-linked immunosorbent assay (sELISA) testing as well as other variants of single-enzyme linked molecular analysis (SELMA).

23 Claims, 16 Drawing Sheets

Specification includes a Sequence Listing.

Related U.S. Application Data

(60) Provisional application No. 62/368,564, filed on Jul. 29, 2016, provisional application No. 62/238,171, filed on Oct. 7, 2015.

(51) Int. Cl.
*G01N 33/52* (2006.01)
*G06M 11/00* (2006.01)

(52) U.S. Cl.
CPC .................. *B01L 2300/0816* (2013.01); *B01L 2300/0819* (2013.01); *B01L 2300/0877* (2013.01); *B01L 2300/165* (2013.01); *B01L 2400/049* (2013.01)

(56) References Cited

U.S. PATENT DOCUMENTS

| | | |
|---|---|---|
| 6,849,462 B1 | 2/2005 | Winkler et al. |
| 6,902,705 B1 | 6/2005 | Caillat et al. |
| 2004/0009543 A1 | 1/2004 | Kiechl et al. |
| 2004/0018491 A1 | 1/2004 | Gunderson et al. |
| 2004/0058450 A1 | 3/2004 | Pamula et al. |
| 2005/0244863 A1 | 11/2005 | Mir |
| 2007/0218452 A1 | 9/2007 | Delattre et al. |
| 2007/0238096 A1 | 10/2007 | Reich et al. |
| 2008/0026379 A1 | 1/2008 | Siddiqi et al. |
| 2009/0142755 A1 | 6/2009 | Albitar |
| 2010/0075407 A1 | 3/2010 | Duffy et al. |
| 2010/0112342 A1 | 5/2010 | Cho |
| 2011/0159564 A1 | 6/2011 | Odawara |
| 2011/0195852 A1 | 8/2011 | Walt et al. |
| 2012/0190030 A1 | 7/2012 | Chun et al. |
| 2013/0052649 A1 | 2/2013 | Lee et al. |
| 2014/0087386 A1 | 3/2014 | Chiu et al. |
| 2014/0248610 A1 | 9/2014 | McKernan et al. |
| 2017/0168040 A1 | 6/2017 | Turner et al. |

FOREIGN PATENT DOCUMENTS

| | | |
|---|---|---|
| CN | 102890474 A | 1/2013 |
| CN | 104531853 A | 4/2015 |
| CN | 104535769 A | 4/2015 |
| CN | 104620093 A | 5/2015 |
| EP | 1 053 784 A2 | 11/2000 |
| EP | 1 156 329 A2 | 11/2001 |
| EP | 1 626 278 A2 | 8/2005 |
| EP | 2 565 279 A1 | 3/2013 |
| EP | 3 048 445 A2 | 7/2016 |
| JP | 2001-059844 A | 3/2001 |
| JP | 2002-525573 A | 8/2002 |
| JP | 2004-309405 A | 11/2004 |
| JP | 2006-088034 A | 4/2006 |
| JP | 2006-88034 A | 4/2006 |
| JP | 2006-194897 A | 7/2006 |
| JP | 2007-020526 A | 2/2007 |
| JP | 2009-068995 A | 4/2009 |
| JP | 2020-515074 | 5/2010 |
| JP | 4 531055 B2 | 8/2010 |
| JP | 2010-210308 A | 9/2010 |
| JP | 2010-538260 A | 12/2010 |
| JP | 2014/021025 A | 2/2014 |
| WO | WO 98/47003 A1 | 10/1998 |
| WO | WO 01/61054 A2 | 8/2001 |
| WO | WO 2006/038647 A1 | 5/2008 |
| WO | WO 2008/053406 A1 | 5/2008 |
| WO | WO 2008/081203 A2 | 7/2008 |
| WO | WO 2009/029073 A1 | 3/2009 |
| WO | WO 2009/109753 A2 | 9/2009 |
| WO | WO 2010/019388 A2 | 2/2010 |
| WO | WO 2010/039180 A2 | 4/2010 |
| WO | WO 2011/097028 A1 | 8/2011 |
| WO | WO 2011/109364 A3 | 9/2011 |
| WO | WO 2012/022482 A1 | 2/2012 |
| WO | WO 2012/072822 A1 | 6/2012 |
| WO | WO 2012/100198 A2 | 7/2012 |
| WO | WO 2012/135730 A2 | 10/2012 |
| WO | WO 2013/063230 A1 | 5/2013 |
| WO | WO 2013/110146 A2 | 8/2013 |
| WO | WO 2013/176767 A1 | 11/2013 |
| WO | WO 2014/001459 A1 | 1/2014 |
| WO | WO 2014/029012 A1 | 2/2014 |
| WO | WO 2015/061362 A1 | 4/2015 |
| WO | WO 2015/109020 A1 | 7/2015 |
| WO | WO 2016/161402 A1 | 10/2016 |
| WO | WO 2017/004463 A1 | 1/2017 |
| WO | WO 2017/034970 A1 | 3/2017 |
| WO | WO 2017/048815 A1 | 3/2017 |

OTHER PUBLICATIONS

Ackermann, B., et anon, Corrections for "Kinetics of alkaline phosphatase from pig kidney. Influence of complexing agentse on stability and activity," *Biochemical Journal*, 1976, vol. 153, pp. 151-157.

Bigelow, W., et al., "Oleophobic Monolayers. I. Films Adsorbed From Solution in Non-Polar Liquids," from the Naval Research Laboratory, Washington, D.C., 1946, pp. 513-538.

Birdi, K., et anon, "A Study of the Evaporation Rates of Small Water Drops Placed on a Solid Surface," *J. Phys. Chem.*, 1989, vol. 93,pp. 3702-3703.

Dressman, D., et al., "Transforming single DNA molecules into fluorescent magnetic particles for detection and enumeration of genetic variations," *PNAS*, 2003, vol. 100(15), pp. 8817-8822.

Gorris, et anon, "Mechanistic Aspects of Horseradish Peroxidase Elucidated throuigh Single-Molecule Studies," *J. Am. Chem. Soc.*, 2009,vol. 131, pp. 6277-6282.

Huebner, A., et al., "Static microdroplet arrays: a microfluidic device for droplet trapping, incubation and release for enzymatic and cell-based assays," *Lab Chip*, 2009, vol. 9, pp. 692-698.

Kim, S., et al., "Large-scle femtoliter droplet array for digital counting of single biomolecules," *Lab Chip*, 2012, pp. 4986-4991.

Kunding, A., et al., "Micro-droplet arrays for micro-compartmentalization using air/water interface," *Lab Chip*, 2018, vol. 18, pp. 2797-2805.

Li, Z., et al., "Detection of Single-Molecule DNA Hybridization Using Enzymatic Amplification in anArray of Femtoliter-Sized Reaction Vessels," *J. Am. Chem. Soc.*, 2008, vol. 130, pp. 12622-12623.

Lien, E., et anon., "Partition Coefficients," *Encyclopedia of Pharmaceutical Technology*, Informa Healthcare USA, 2007, pp. 2595-2603.

Mao, L., et al., "Horseradish Peroxidase Inactivation: Heme Destruction and Influence of Polyethylene Glycol," *Scientific Reports*, 2013, vol. 3(3216), pp. 1-7.

Pekin, D., et al., "Quantitative and sensitive detection of rare mutations using droplet-based microfluidics," *Lab Chip*, 2011, vol. 11, pp. 2156-2166.

Pohl, G., et anon, "Principle and applications of digital PCR," *Expert Rev. Mol. Diagn.*, 2004, vol. 4(1), pp. 41-47.

Rissin, D., et al., "Single-molecule enzyme-linked immunoabsorbent assey detects serum proteins at subfemtomolar concentrations," *Nature Biotechnology*, 2010, vol. 28(6), p. 595-600.

Ritchie, J., et al., "Metastable Sessile Nanodroplets on Nanopatterned Surfaces," *The Journal of Physical Chemistry*, 2012, vol. 116, pp. 8634-8641.

Sasagawa, K., et al., "Lensless CMOS-Based Imaging Device For Fluorescent Femtoliter Droplet Array Counting," *17th International Conference on Miniaturized Systems for Chemistry and Life Sciences*, Freiburg, Germany, 2013, vol. 3, pp. 1565-1567.

Temiz, Y., et al., "Lab-on-a-chip devices: How to close and plug the lab?," *Microelectronic Engineering*, 2015, vol. 132, pp. 156-175.

Vogelstein, B., et anon, "Digital PCR," *Proc. Natl. Acad. Sci. USA*, 1999, vol. 96, pp. 9236-9241.

Weinrich, D, et al., "Applications of Protein Biochips in Biomedical and Biotechnological Research," *Angew. Chem. Int. Ed.*, 2009, vol. 48, pp. 7744-7751.

(56) References Cited

OTHER PUBLICATIONS

Witters, D., et al., "Digital microfluidics-enabled single-molecule detection by printing and sealing single magnetic beads in femtoliter drops," *Lab Chip*, 2013, vol. 13, pp. 2047-2054.
Witters, D., et al., "Digital biology and chemistry," *Lab Chip*, 2014, vol. 14, pp. 3225-3232.
Rust, Michael, et al., Sub-diffraction-limit imaging by stochastic optical reconstruction microscopy (STORM), Nature Methods, 2006, vol. 3(10), pp. 793-795.
Guo, Q., et al., "A molecular beacon microarray based on a quantum dot label for detecting single nucleotide polymorphisms," *Biosensors and Bioelectronics*, 2016, vol. 77, pp. 107-110.

* cited by examiner (i)

(ii)

SEQUENCE LISTING

<160> NUMBER OF SEQ ID NOS: 7

<210> SEQ ID NO 1
<211> LENGTH: 14
<212> TYPE: DNA
<213> ORGANISM: Artificial sequence
<220> FEATURE:
<223> OTHER INFORMATION: PNA analogue of DNA sequence

<400> SEQUENCE: 1
acatagttga cacg                                                      14

<210> SEQ ID NO 2
<211> LENGTH: 50
<212> TYPE: DNA
<213> ORGANISM: Artificial sequence
<220> FEATURE:
<223> OTHER INFORMATION: Model oligonucleotide

<400> SEQUENCE: 2
tctgtcgtag gcacagagcg gtcttacggc cagtcgcgtg tcaactatgt               50

<210> SEQ ID NO 3
<211> LENGTH: 12
<212> TYPE: DNA
<213> ORGANISM: Artificial sequence
<220> FEATURE:
<223> OTHER INFORMATION: Biotin-labelled DNA oligonucleotide

<400> SEQUENCE: 3
gcctacgaca ga                                                        12

<210> SEQ ID NO 4
<211> LENGTH: 48
<212> TYPE: DNA
<213> ORGANISM: Artificial sequence
<220> FEATURE:
<223> OTHER INFORMATION: Model target DNA

<400> SEQUENCE: 4
tctgtcgtag gcacagagcg gtcttacggc cagtcgcgtg tcaactat                 48

<210> SEQ ID NO 5

```
<211> LENGTH: 48
<212> TYPE: DNA
<213> ORGANISM: Artificial sequence
<220> FEATURE:
<223> OTHER INFORMATION: Model non-target DNA

<400> SEQUENCE: 5
tctgtcgtag gcacagagcg gtcttacggc cagtcgcgtg tccactat                  48

<210> SEQ ID NO 6
<211> LENGTH: 14
<212> TYPE: DNA
<213> ORGANISM: Artificial sequence
<220> FEATURE:
<223> OTHER INFORMATION: PNA-modified capture probe

<400> SEQUENCE: 6
gtgcctacga caga                                                       14

<210> SEQ ID NO 7
<211> LENGTH: 11
<212> TYPE: DNA
<213> ORGANISM: Artificial sequence
<220> FEATURE:
<223> OTHER INFORMATION: Single stranded DNA label

<400> SEQUENCE: 7
atagttgaca c                                                          11
```

FLOW SYSTEM AND METHODS FOR DIGITAL COUNTING

CROSS-REFERENCE TO RELATED APPLICATIONS

This application is a divisional of U.S. application Ser. No. 15/551,410, Aug. 16, 2017, which is a national stage filing under 35 U.S.C. 371 of PCT/EP2016/074045, filed Oct. 7, 2016, which International Application was published by the International Bureau in English on Apr. 13, 2017, and application claims priority from U.S. application Ser. No. 62/238,171, filed Oct. 7, 2015, and U.S. Application No. 62/368,564, filed Jul. 29, 2016, which applications are hereby incorporated in their entirety by reference in this application.

FIELD OF THE INVENTION

The present invention relates to methods and systems for testing for the presence of a material such as one or more analyte types within a sample and more particularly, for improved single enzyme-linked immunosorbent assay (sELISA) testing as well as other variants of single-enzyme linked molecular analysis (SELMA).

BACKGROUND OF THE INVENTION

Scientists are developing techniques for analyzing changes in biological and chemical systems, where these changes often relate to the switching between two or more states. For example, Witters et al. in Digital Biology and Chemistry (DOI: 10.1039/C4LC00248B, (Frontier) Lab on a Chip, 2014, 14, pp. 3225-3232) discuss the development of various digital biological and chemical technologies. These digital technologies can work quite well, as digital techniques offer advantages in terms of robustness, assay design, and simplicity because quantitative information can be obtained with qualitative measurements. However, digital techniques can be relatively complex, in part due to the technical difficulty in isolating and manipulating single molecules. For example, some techniques use micron-sized magnetic beads to process samples of femtoliter volumes. See Rissin et al., in Single-molecule enzyme-linked immunosorbent assay detects serum proteins at subfemtomolar concentrations (DOI:10.1038/nbt.1641, Nature Biotechnology 2010, 28, pp. 595-599). Other techniques use even smaller volumes of attoliters. These tiny volumes can create challenges because the fluid dynamics of small volumes present behaviors, at typical laboratory temperature and pressure that make processing difficult.

For example, most digital detection techniques rely on the micro-compartmentalization of a liquid containing analytes and various detection- and capture-probes. The analytes and detection/capture probes are carried, or exist within, micron-sized droplets, typically of pico-to-attoliter volumes.

Therefore, the way to partition the sample in to smaller volumes is the most important part of a digital detection process. The most readily available device format relies on solid or polymeric substrates forming an array of micro-compartments into which the sample can be transferred. These arrays mainly come in two varieties; (i) the micro-well arrays and (ii) the capillary arrays. In a micro-well array, the compartment is made up by a recess in the substrate, whereas in a capillary array the compartment extends all the way through the substrate, thus forming a through hole. A major challenge inherent in both of these array types is the way that they are loaded with sample and accessory reagents. In the micro-well array, the recess may not readily be filled up with a liquid sample, because air cannot leave the well due to the microscopic dimensions of the well, as an example of this see the research article by Kim et al. entitled "Large-scale femtoliter droplet array for digital counting of single biomolecules" published in Lab on a Chip, (2012) vol. 12, pp. 4986-4991 (DOI: 10.1039/c2lc40632b). This problem is absent from capillary arrays, because each compartment has two openings, such that if the liquid sample is added from the top opening, then air can escape through the bottom opening. However, when it comes to exchanging the liquid held within the micro-well or capillary compartments with another liquid, an additional issue arises, which is caused by the slow diffusion of molecules. Because both the micro-wells and capillaries are positioned perpendicular to the flow of the liquid phase being added, then good mixing cannot take place, and hence liquid exchange can only take place by molecular diffusion from the bulk liquid into the capillary and vice versa. Consequently, to ensure proper liquid exchange a time-delay (the length of which will depend on the dimensions of the micro-wells/capillaries and the type of molecular species being added) will have to be applied.

To overcome these challenges a third kind of array has been developed, which will be referred to as surface-tension arrays. A surface-tension array is planar and consists of hydrophilic features patterned in or onto a hydrophobic substrate. When a surface-tension array is contacted with an aqueous sample (e.g. by immersion into the aqueous phase and withdrawal of the array) individual droplets may form on the hydrophilic features due to the surface-tension difference between the features and the surrounding substrate. Because the droplets rest on a planar surface, then liquid loading as well as liquid exchange may take place instantaneously (or at least several orders of magnitude faster than for diffusion-limited transport) when a liquid sample is introduced on the array. Unlike the micro-well array, no air can be trapped beneath the liquid and the hydrophilic features and since the array does not rely on depressions/recesses/cavities in the substrate, then liquid mixing between droplets and the bulk liquid is not limited by molecular diffusion. However, all three types of micro-compartmentalization formats (micro-well, capillary and surface tension arrays) are facing the challenge of preserving a large number of liquid micro-droplets for a sufficient long time in order to allow digital counting to be conducted.

At typical ambient temperature and pressure for a laboratory, these microdroplets evaporate within seconds, see for example the research article by Birdi, K. S., Vu, D. T. and Winter, A. entitled "A study of the evaporation rates of small water drops placed on a solid surface" published in The Journal of Physical Chemistry, 1989, vol. 93, pp. 3702-3703 (DOI: 10.1021/j100346a065).

Once evaporated, the ability to process the molecule within the microdroplet is gone, the digital technique cannot be carried out.

Accordingly, it is necessary to prevent rapid evaporation and maintain the microdroplet of a period of time sufficient to measure for the presence of the molecule of interest.

To this end, scientists and engineers have developed certain techniques that seal the compartments that are holding the microdroplets. These seals prevent the microdroplets from contacting the ambient environment and thus prevent evaporation.

There are in general two techniques for sealing a compartment: a physical seal and a chemical seal. The physical seal is used when the compartments are structured as micro-recesses or micro-cavities in a substrate. To physically seal the compartments, an air-tight lid is attached on top of the compartments. In this way, the content of individual compartments cannot evaporate and neighboring compartments cannot exchange their content, which would otherwise lead to cross-contamination. The disadvantage of having a physical seal is that once the compartments have been sealed off, the analysis ends, because the lid cannot be easily removed without disrupting the integrity of the micro-compartments. Furthermore, to apply a physical seal, the compartments have to be structured as micro-wells/-cavities/-recesses, which, due to slow molecular diffusion, results in technical difficulties with exchanging the liquid in the compartments during the initial preparative steps.

One type of chemical seal relies on covering the compartments with an oil (or non-polar liquid) phase. In this way, evaporation of the sample is reduced, because water from the sample only slowly partitions into the oil phase. The advantage of a chemical seal is that it is based on interfacial tension, and hence the compartments do not need to be structured as cavities, but can instead be formed as droplets resting on a surface. This feature enables fast reagent exchange, which is not limited by molecular diffusion, but is instead determined by the flowrate at which the new reagent is introduced. Furthermore, unlike the physical seal, the chemical seal may be removed more easily by aspirating the oil phase from the sample. However, one of the disadvantages of a chemical seal is that analytes or other biomolecules from the sample may partition into the non-polar phase and lead to (i) sample loss and/or (ii) inter-droplet contamination. In particular, biomolecules such as proteins, are prone to be soluble in non-polar liquids, mainly due to the fact that hydrophobic amino acids in the protein may rearrange themselves upon exposure to a hydrophobic interface. This property of molecules to partition from water into a non-polar phase is described by the partition coefficient, i.e. oil-water partition coefficient, water-octanol partition coefficient, etc, e.g. in Lien, E. J. and Ren, S. S. in Chapter 186 in Encyclopedia of Pharmaceutical Technology, Third Edition, 2006, ISBN: 9780849393990. Furthermore, it has been shown that even water—although slowly—partitions into a surrounding oil phase, e.g. see the work of Huebner, A. et al published in Lab on a Chip, 2009, vol. 9, pp. 692-698 (DOI: 10.1039/B813709A). Even further, when a bulk aqueous phase is displaced by a bulk oil phase or vice versa there is a risk of producing emulsion droplets, i.e. micron-sized inclusions of water in oil or vice versa. Emulsion droplets may constitute an experimental nuisance, since they can foul the surfaces and/or deteriorate the flow-performance of the device.

WO2015061362 A1 entitled "Enrichment and detection of nucleic acids with ultrahigh sensitivity" describes how to prepare a non-sealed surface-tension array of liquid droplets exhibiting a fast evaporation rate. WO2013110146 A2 entitled "Patterning device" describes how to prepare a surface tension array of liquid droplets and how to use it for bioassays under a chemical seal. WO2013063230 A1 entitled "Device and method for apportionment and manipulation of sample volumes" describes methods for preparing and using chemically sealed surface-tension arrays for bioassays including digital counting measurements. JP2014021025A entitled "Apparatus and method for forming artificial lipid membrane" describes how to prepare a surface-tension array chemically sealed with a lipid membrane. WO2010039180 A2 entitled "High sensitivity determination of the concentration of analyte molecules or particles in a fluid sample" describes digital counting of analytes by dividing a sample into physically sealed micro-well compartments. WO2010019388 A2 entitled "Method and apparatus for discretization and manipulation of sample volumes" describes micro-well compartments, which may be used to capture and divide a liquid sample by applying a chemical seal comprised by one or more immiscible liquids. WO2012022482 A1 entitled "Microwell arrays for direct quantification of analytes on a flat sample" describes the use of physically sealed micro-well compartments for analyzing samples contained on a flat substrate. US20100075407 A1 entitled "Ultrasensitive detection of molecules on single molecule arrays" describes digital counting measurements conducted in physically sealed micro-well compartments. WO2012100198 A2 entitled "Methods and systems for performing digital measurements" describes a digital counting measurement conducted by preparing and analyzing arrays of liquid droplets. US20130052649 A1 entitled "Multilayer high density microwells" describes chemically sealed arrays of micro-well compartments for bioanalysis. WO2001061054 A2 entitled "Apparatus and methods for parallel processing of micro-volume liquid reactions" describes the use of chemically sealed capillary arrays for conducting bioassays. WO2014001459 A1 entitled "A method of charging a test carrier and a test carrier" describes the use of capillary arrays for conducting bioassays. WO1998047003 A1 entitled "An analytical assembly for polymerase chain reaction" describes digital counting of oligonucleotides.

Accordingly, there remains a need in the art for improved systems and methods for sealing compartments holding micro-droplets containing material being analyzed.

SUMMARY

In a first aspect disclosed herein, is a flow system for digital counting of one or more distinct analyte types in a sample comprising a support having a pattern of hydrophilic features in or on a hydrophobic substrate, the hydrophobic substrate being embedded in a flow compartment comprising at least one opening, the hydrophilic features configured to support a plurality of liquid nano-to-attoliter droplets.

In a further aspect disclosed herein, is a flow system (10) for digital counting of one or more distinct analyte types in a sample comprising a support (12) having a pattern of planar hydrophilic features (14) in or on a planar hydrophobic substrate (16), the hydrophobic substrate (16) being embedded in a flow compartment (18) comprising at least one opening (20), the hydrophilic features (14) configured to support a plurality of liquid nano-to-attoliter droplets, comprising at least one capture probe (22) for the one or more distinct analyte types, the capture probe(s) (22) being attached to the hydrophilic features (14).

In a second aspect disclosed herein, is a flow system for digital counting of one or more analyte types in a sample comprising a support having a pattern of hydrophilic features in or on a hydrophobic substrate, the hydrophobic substrate being embedded in a flow compartment comprising at least one opening, the hydrophilic features configured to support a plurality of liquid nano-to-attoliter droplets each having a maximum droplet volume, and the flow compartment configured to support a gas phase seal reducing evaporation of each nano-to-attoliter droplet.

In a further aspect disclosed herein, is a flow system (10) for digital counting of one or more analyte types in a sample, the flow system comprising a support (12) having a pattern of hydrophilic features (14) in or on a hydrophobic substrate (16), the hydrophobic substrate (16) being embedded in a flow compartment (18) comprising at least one opening (20), the hydrophilic features (14) configured to support a plurality of liquid nano-to-attoliter droplets each having a maximum droplet volume, and the flow compartment (18) configured to support a gas phase seal reducing evaporation of each nano-to-attoliter droplet, wherein the flow compartment (18) has a volume ($V_C$), where the volume ($V_C$) is greater than an aggregate maximum droplet volume ($V_{DA}$) of all liquid nano-to-attoliter droplets and is less than $V_{MAX}$ calculated by the following equation:

$$V_{MAX} = V_{DA} \frac{\rho_L RT}{(1-RHI)M_W P_0} \exp\left(\frac{\Delta H_{VAP}}{R}\left(\frac{1}{T} - \frac{1}{T_0}\right)\right)$$

where $\rho_L$ is the volume density of the liquid, R is the molar gas constant, T is the temperature, RHI is the initial relative vapor saturation of the gas component of the liquid, $P_0$ is a reference vapor pressure of the liquid at a corresponding reference temperature $T_0$, $M_W$ is the molar weight of the liquid and $\Delta H_{VAP}$ is the enthalpy of evaporation of the liquid. In a further aspect disclosed herein, is a method of preparing a flow system as disclosed herein.

In a further aspect disclosed herein, is a method of using a flow system as described herein for digital counting of at least one or more distinct analyte types.

In another aspect disclosed herein, is a method for digital counting of at least one or more distinct analyte types, the method comprising counting the analyte types contained in a plurality of liquid nano-to-attoliter droplets under a gas phase seal.

In another aspect disclosed herein, is a use of a plurality of liquid nano-to-attoliter droplets under a gas phase seal for digital counting of at least one or more distinct analyte types.

Herein, the feature of the hydrophilic features being configured to support a plurality of liquid nano-to-attoliter droplets may particularly mean that the hydrophilic features form a pattern of material having a first hydrophilic property surrounded by material having a second hydrophilic property, the first property being more hydrophilic than the second property, meaning that the contact angle is lower for droplets on the material with the first hydrophilic property. In one example, the material with the second hydrophilic property is considered to be hydrophobic whereby the droplets are essentially exclusively located at the material having the first hydrophilic property.

The feature of the flow compartment being configured to support a gas phase seal reducing evaporation refers to the volume of the flow compartment relative to the volume of the droplets. A flow compartment having a volume $V_C$ being within the boundaries set by the formula:

$$V_{DA} < V_C < V_{MAX} = V_{DA} \frac{\rho_L RT}{(1-RHI)M_W P_0} \exp\left(\frac{\Delta H_{VAP}}{R}\left(\frac{1}{T} - \frac{1}{T_0}\right)\right)$$

is herein considered to be within the definition of a compartment being configured to support a gas phase seal reducing evaporation.

An example of a gas phase, which reduces evaporation, could be a vapor essentially being at its saturation temperature and pressure such that it is incapable of increasing the relative humidity, i.e. near 100 pct. humidity or at least in the range of 90-100 pct. such as in the range of 95-100 pct. humidity. The term "opening" means an entrance for the sample to enter the hydrophilic features on the hydrophobic substrate. The opening could be formed by one or more inlets of the same or different sizes from outside into the compartment.

The flow compartment is a compartment in which the sample can flow and which houses the hydrophilic features on the hydrophobic substrate. The flow compartment could be formed by one or more distinct chambers. If it is defined by more than one chamber, the chambers are in fluid connection.

A capture probe is a feature which is capable of capturing a specific constituent. The capture probe may e.g. be based on PNA or DNA, e.g. a single-stranded PNA oligo.

In one embodiment, the support for the hydrophilic features is located centrally within the flow compartment. In one example, the support for the hydrophilic features are surrounded in the flow compartment by a hydrophobic material forming a boundary about the support for the hydrophilic features.

DETAILED DISCLOSURE

In an embodiment, the systems and methods described herein provide an improved seal for microdroplets and to that end provide a gas-phase seal. In one embodiment, the systems and methods described herein include a channel-shaped flow compartment that has a surface for supporting a plurality of microdroplets. In an embodiment, as disclosed herein the channel shaped flow compartment also has a surface that extends over the surface supporting the microdroplets and includes walls so that the channel-shaped flow compartment has two openings, one on either side of the flow compartment. In one embodiment, the channel is rectangular with a square cross-section so that each opening is square. In other embodiments, the flow compartment is cylindrical and each opening is circular. In both these embodiments, the microdroplets are spaced apart from each other, for example in an array, and located centrally within the flow compartment. In an embodiment, the centrally located microdroplets are spaced a length ($L_E$) away from each of the openings. In one embodiment, the height (h) of the flow compartment is selected based in part on the aggregate volume of fluid contained in the microdroplets, the temperature and pressure of the ambient environment contacting the flow compartment and the length $L_E$. In one embodiment, the height h is selected to create a vapor pressure within the flow compartment that reduces the rate at which the microdroplets will evaporate. Not to be bound by theory, but as the microdroplets evaporate, the vapor from the evaporation creates a gas-phase seal that reduces the rate at which evaporation takes place as compared to the rate that the microdroplets would experience if generally exposed to the ambient environment. In one practice, it is understood that for aqueous solutions, a certain fraction of the water will evaporate into the gas-phase. However, the degree of evaporation can be predicted and rationally controlled by choosing (i) the right flowchannel depth and geometry, (ii) the right droplet volume and (iii) the right microdroplet array geometry. By selecting the parameters correctly, the microdroplets will not evaporate due to the vapor pressure, and thus increased humidity, in the flowchannel. This provides a gas-phase seal, which is similar to a chemical seal, but instead of covering the flow compartments with a liquid phase, the micro-droplets are maintained in a gas-phase, such as air. The advantage of a gas-phase as compared to a liquid phase is that many large biomolecules (proteins, DNA, lipids, etc.) do not partition into air, because their boiling point is significantly higher than water. Unlike the chemical seal, a gas-phase seal allows reagents to be easily introduced on the array without having to remove an oil-phase.

For embodiments where the flow compartments store micro-droplets resting on a planar substrate held in place by surface tension and integrated into a flow channel, a gas-phase seal can be established by contacting the array with a liquid followed by liquid withdrawal. Upon liquid withdrawal the array will retain the micro-droplets and the flow channel will be filled with for example air, thus establishing a gas-phase seal. Thus, the systems and methods described herein provide, among other things, a surface-tension based micro-droplet array embedded in a flow channel, in which the geometry of the flow channel is matched to the geometry of the array, such as to reduce the evaporation below a certain fraction, e.g. less than 5%.

LEGENDS TO THE FIGURE

The foregoing and other objects and advantages of the invention will be appreciated more fully from the following further description thereof, with reference to the accompanying drawings wherein.

Figure 4:
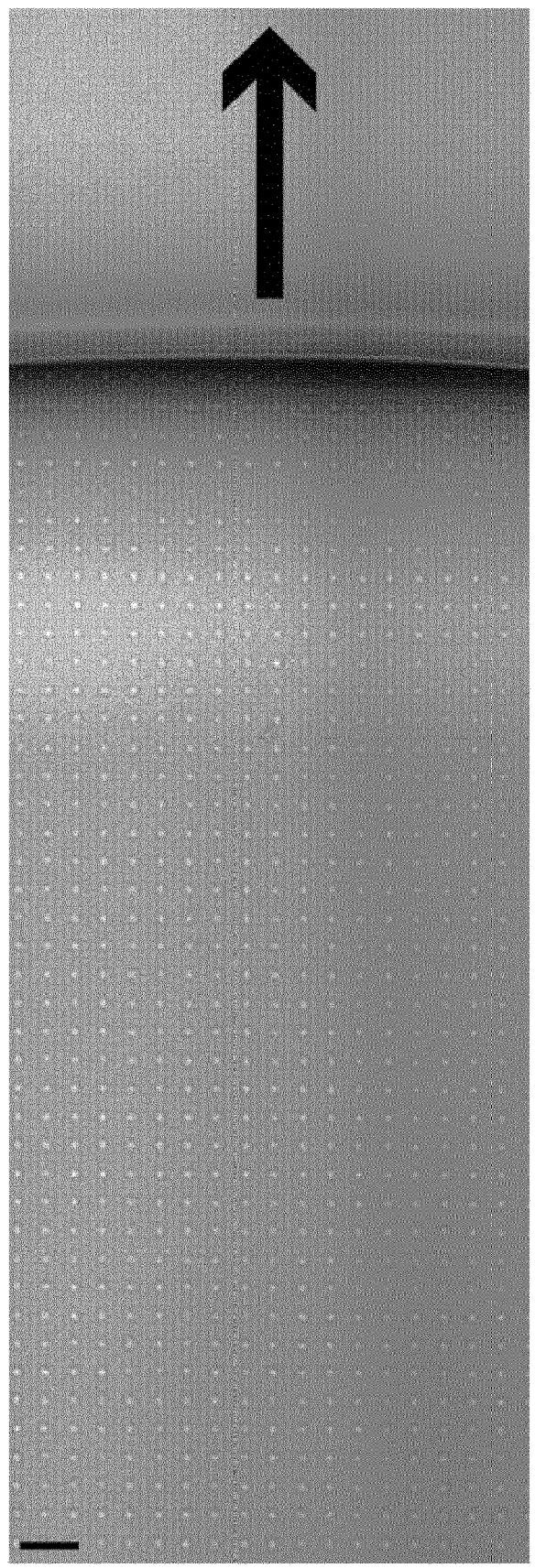
Figure 5:
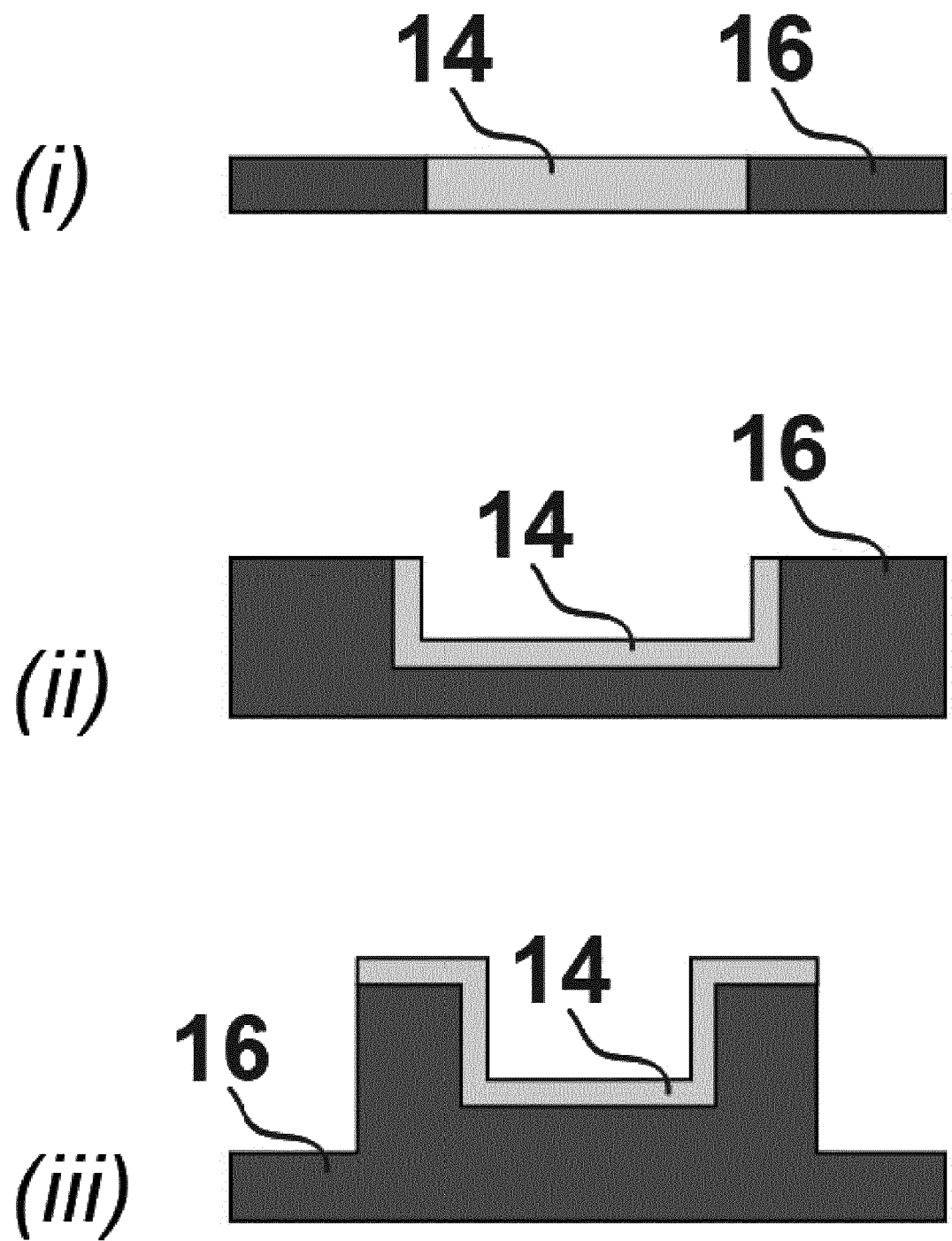
Figure 6:
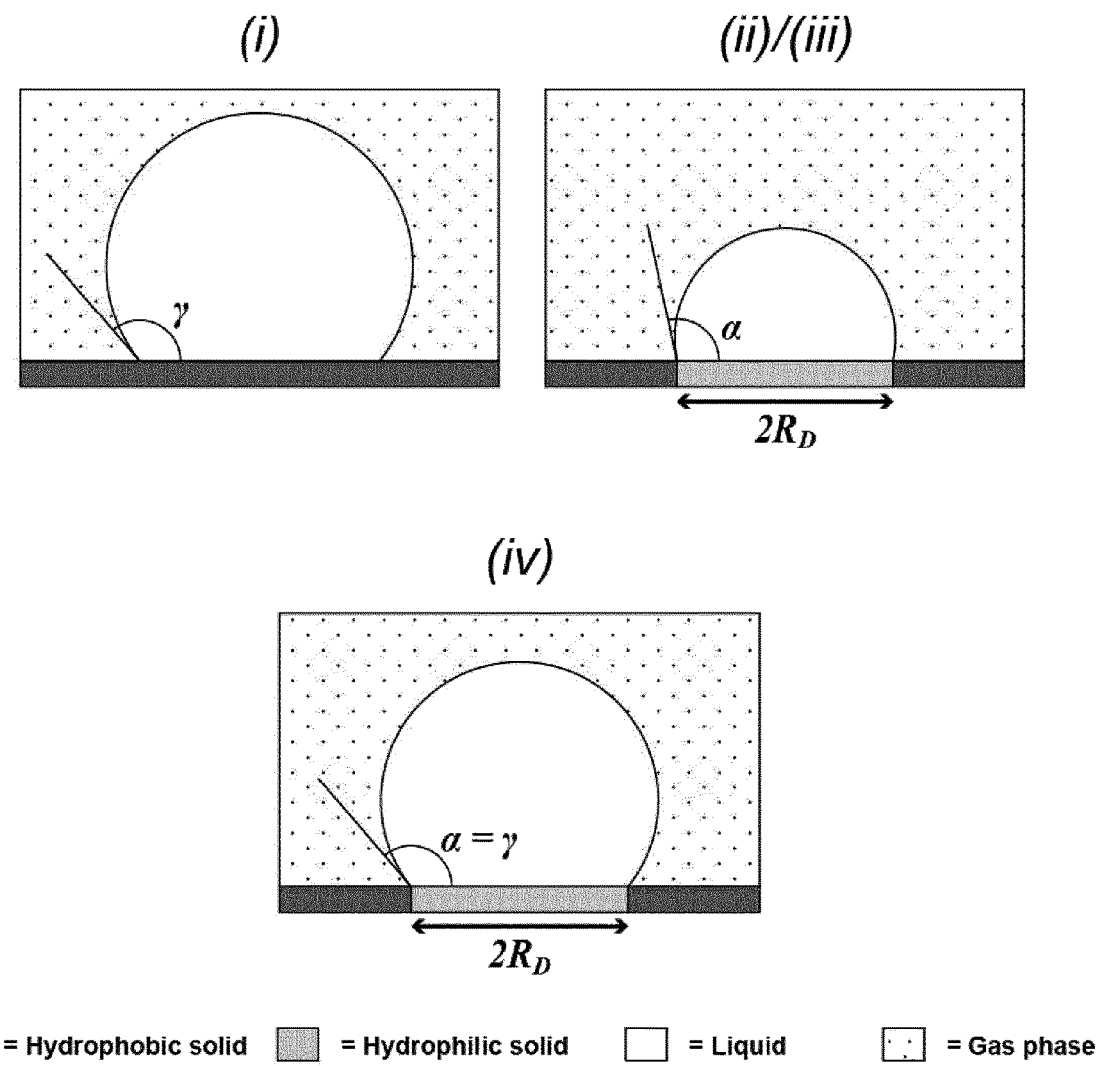
Figure 7:
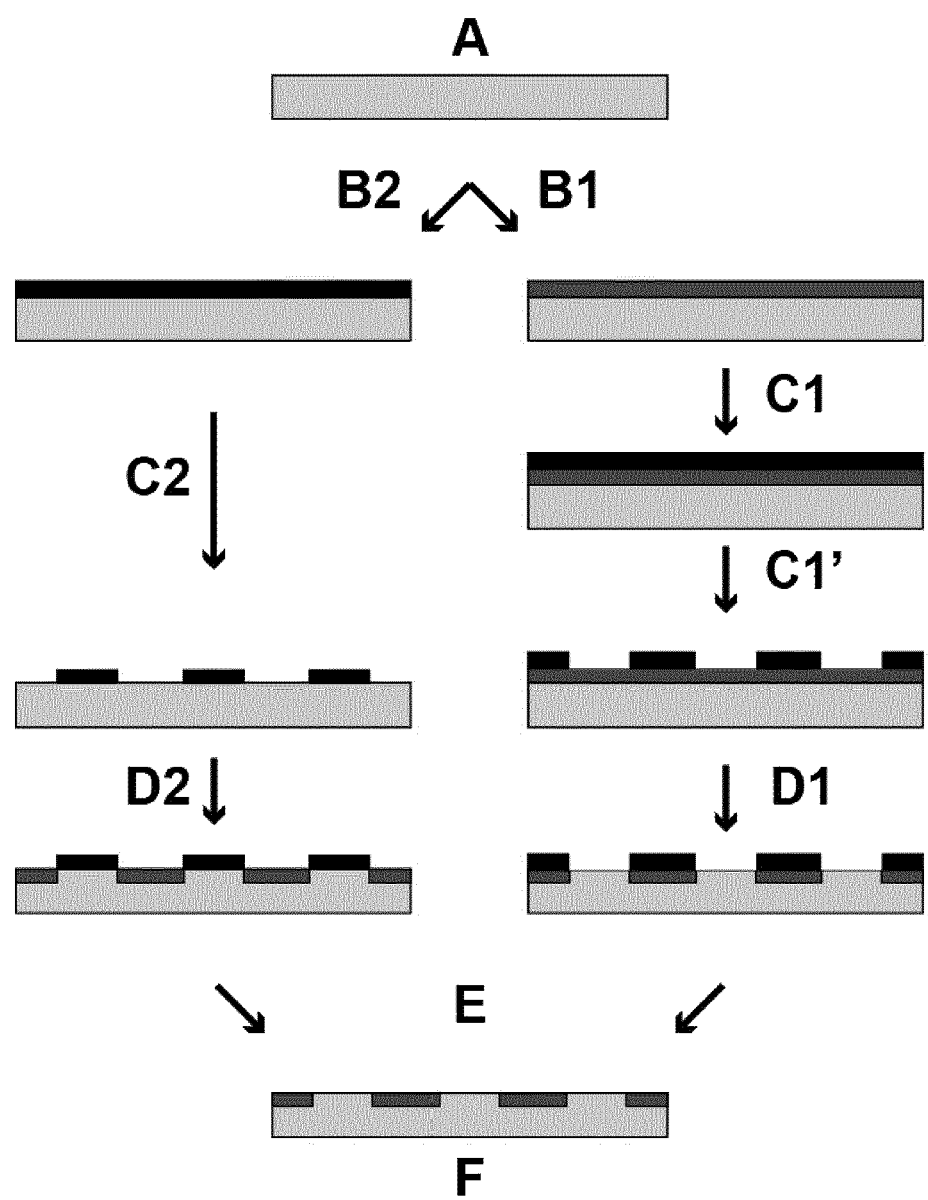

FIG. 4 depicts an exemplary representation of a process of drawing a fluid from the flow compartment to create a gas phase seal. The depiction is an excerpt from a brightfield micrograph acquired when the flow system is being operated, see Example 1-5. The scale bar on the brightfield micrograph is 20 µm;

FIG. 5 depicts exemplary representations of hydrophilic features 14 including (i) a planar feature, (ii) a feature shaped as a depression in the hydrophobic substrate 16 and (iii) a feature comprising a protrusion from the hydrophobic substrate in which a depression contains the hydrophilic zone. The sketch is not drawn to scale;

FIG. 6 depicts examples of liquid droplets in contact with a solid support. In this example, the following are shown on the sketches; examples of (i) the contact angle ($\gamma$) of a liquid droplet resting on a hydrophobic substrate in a gas atmosphere, (ii) the radius ($R_D$) of a circular planar hydrophilic feature, (iii) the contact angle ($\alpha$) of a liquid droplet resting on a circular planar hydrophilic feature and (iv) the geometrical definition of the maximum droplet volume for a circular planar hydrophilic feature. The sketch is not drawn to scale;

FIG. 7 depicts two exemplary photolithography-based processes to prepare a pattern of planar hydrophilic features surrounded by a hydrophobic substrate. The illustrated steps comprise:

A—providing a hydrophilic wafer substrate
B2—deposition of photosensitive thin film coating; or
B1—homogeneous surface modification of the wafer
 C2—UV exposure and development of the coating; or
 C1—deposition of photosensitive thin film coating, followed by C1'—UV exposure and development of the coating
D2—hydrophobic surface modification of the wafer, or
D1—selective etching of the hydrophobic layer E—removal of thin film coating, to achieve—F—a planar pattern of hydrophilic features.

Figure 8:
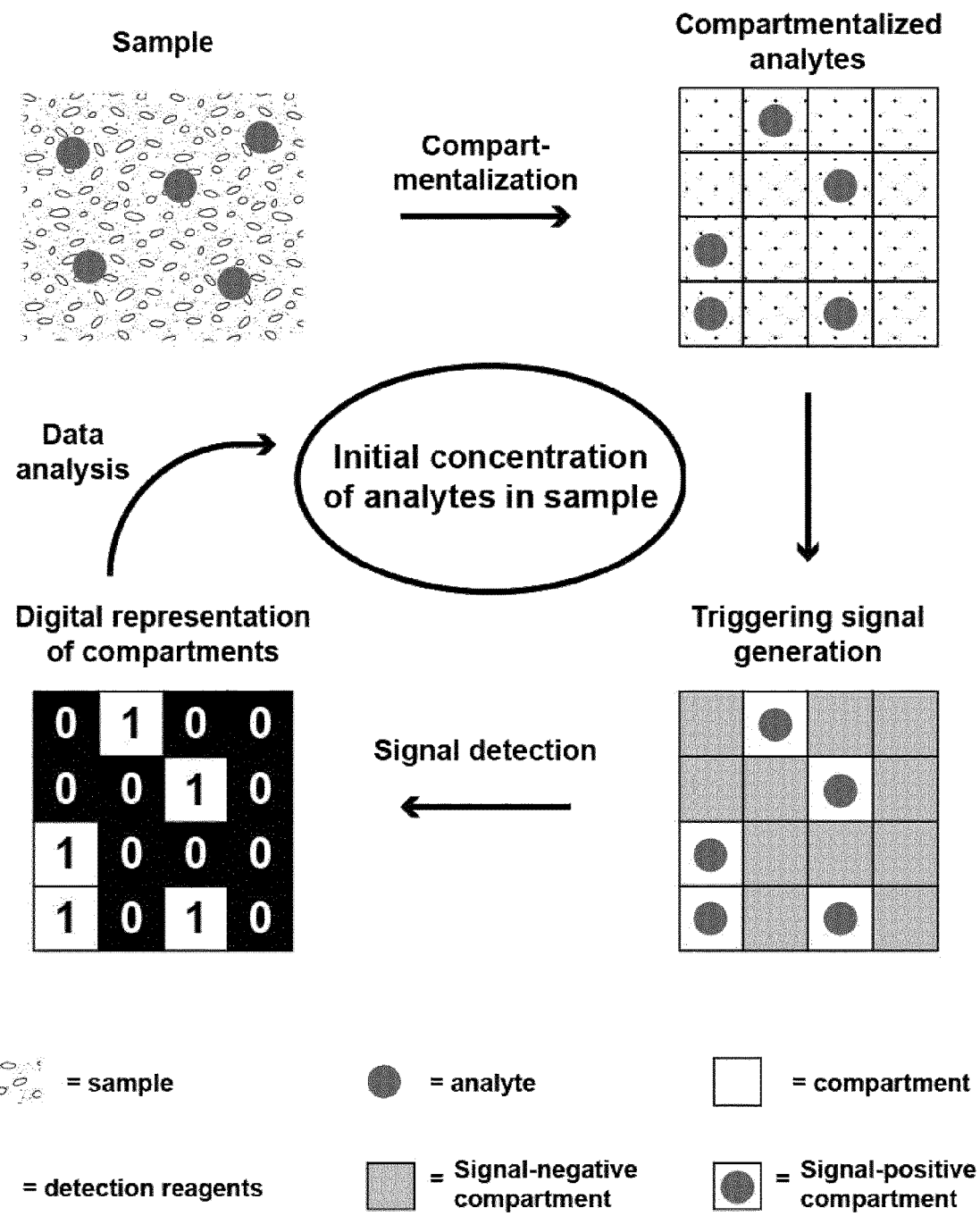
Figure 9A:
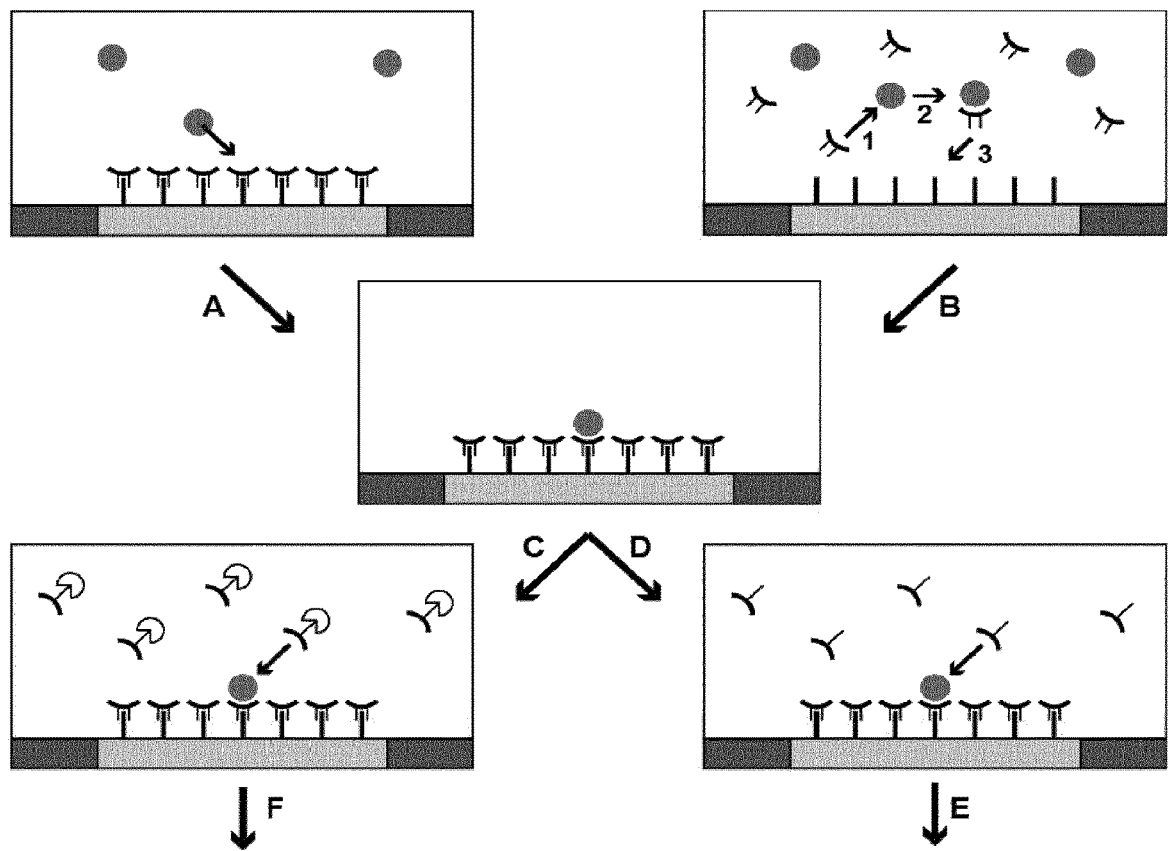
Figure 9B:
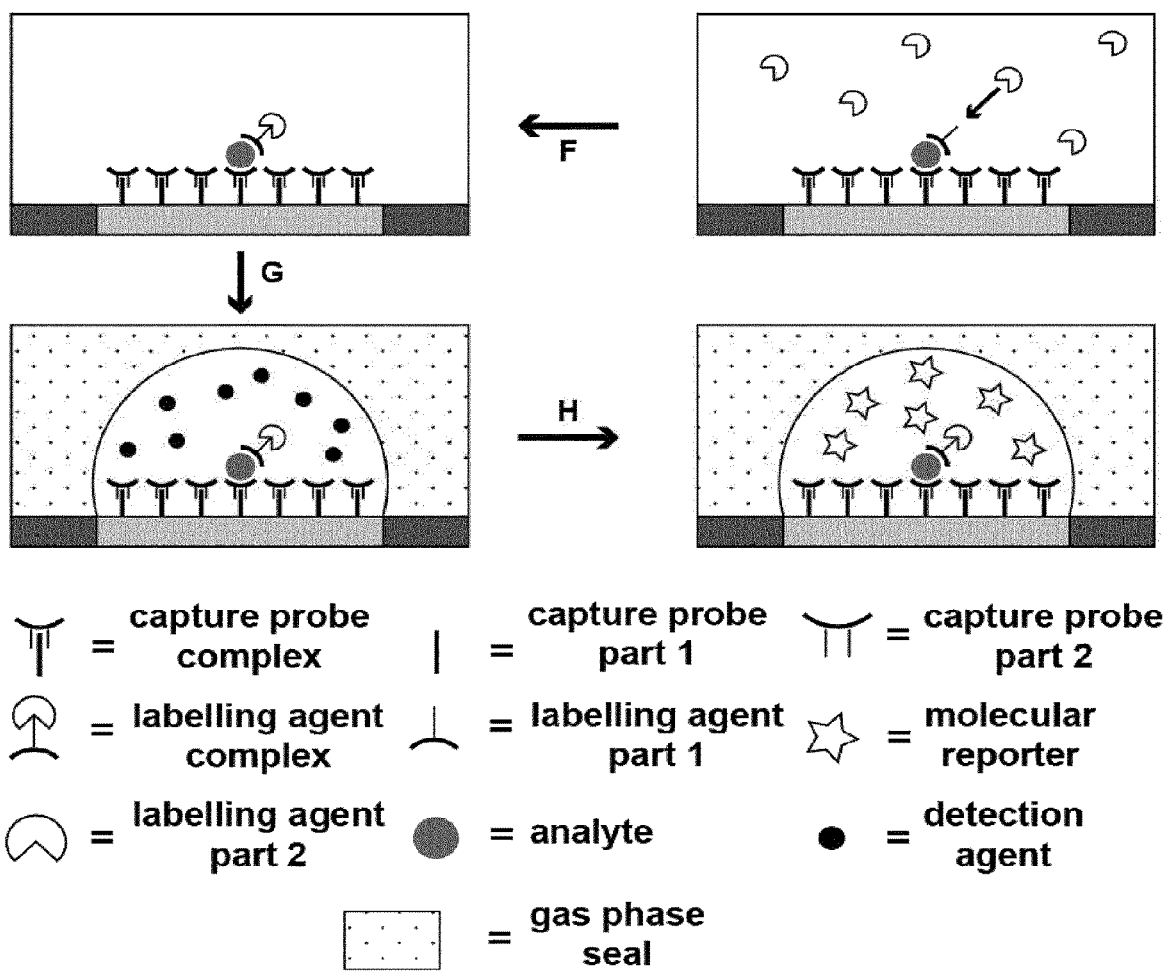
Figure 10:
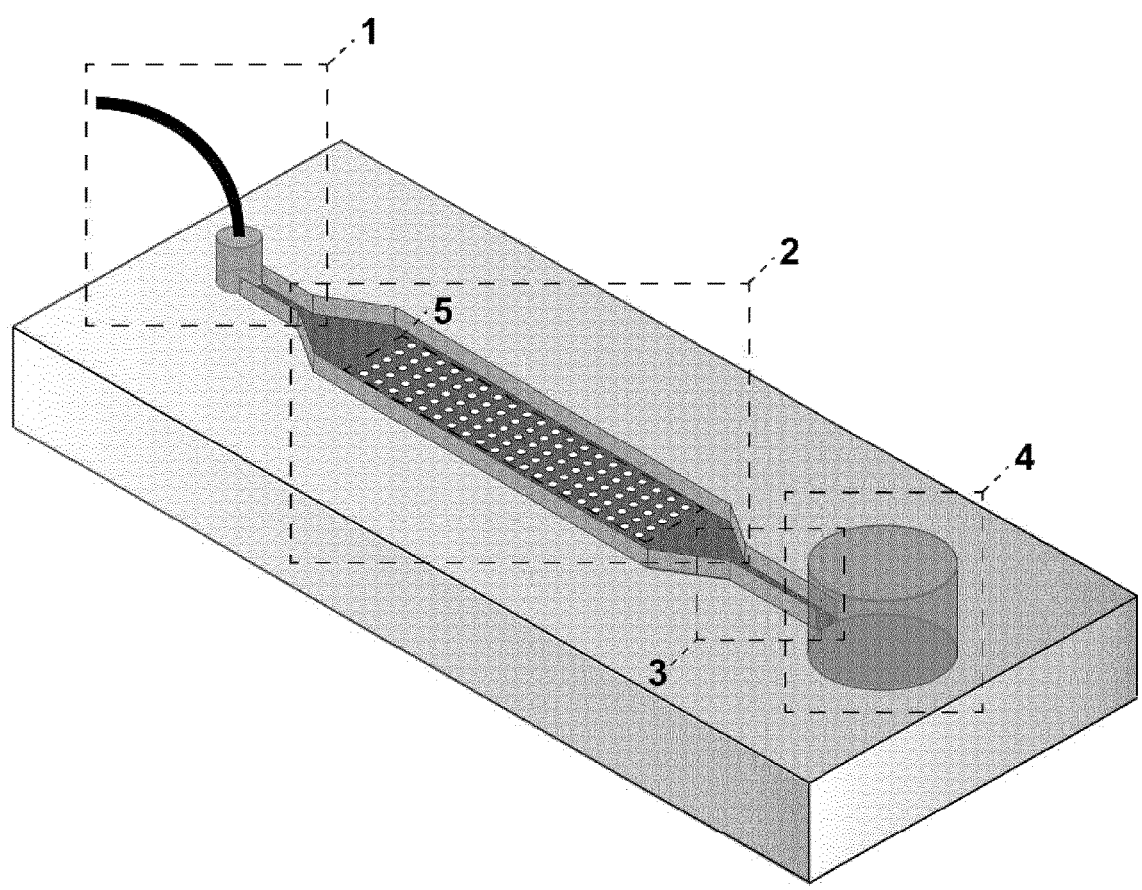
Figure 11:
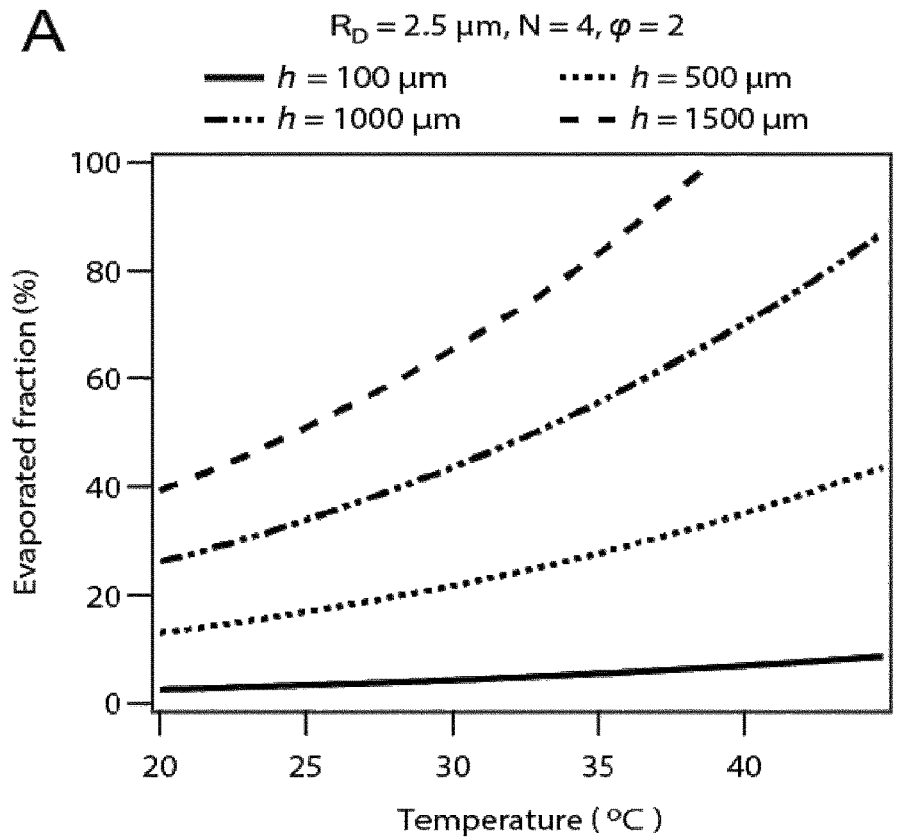
Figure 11:
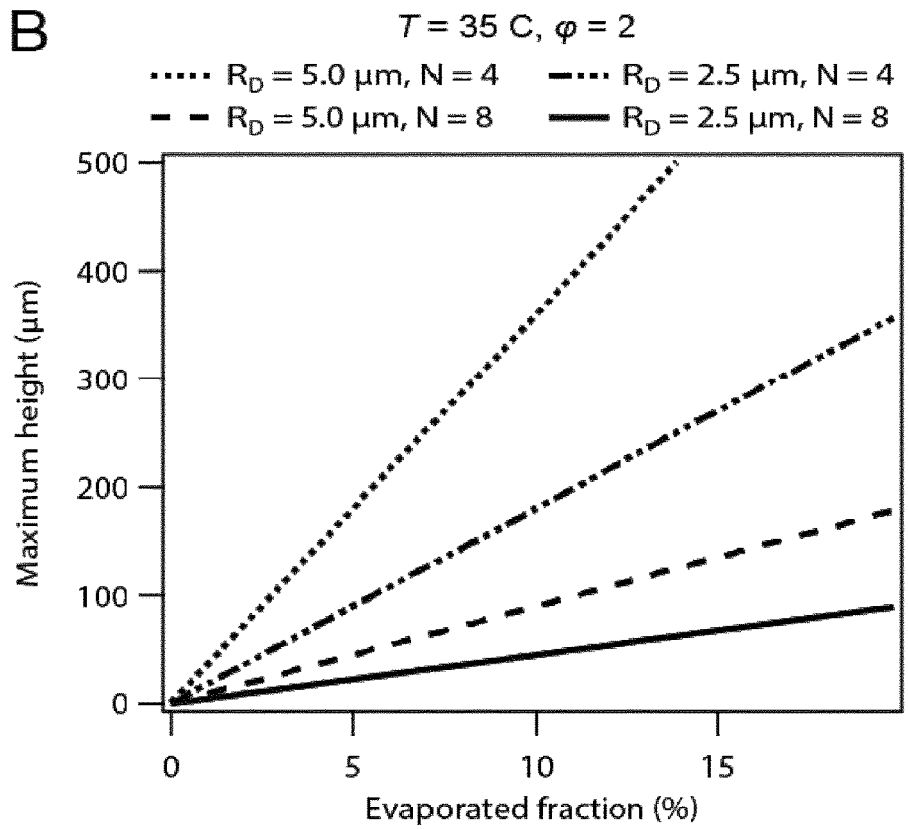
Figure 11:
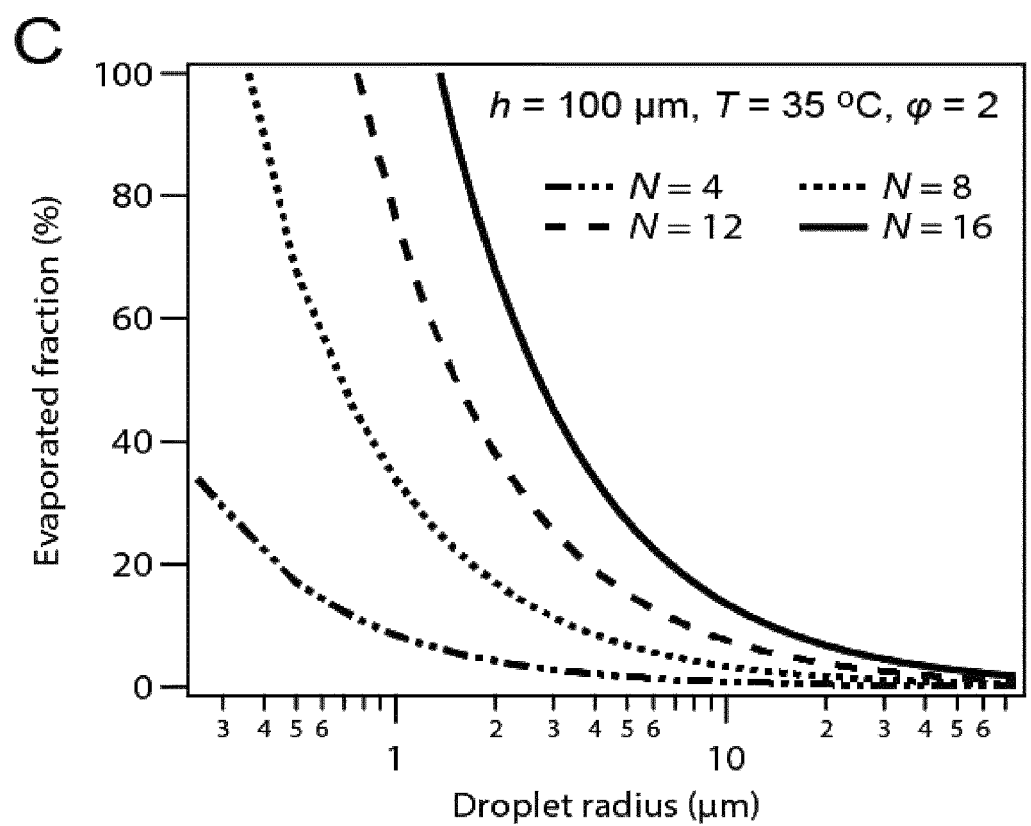
Figure 12:
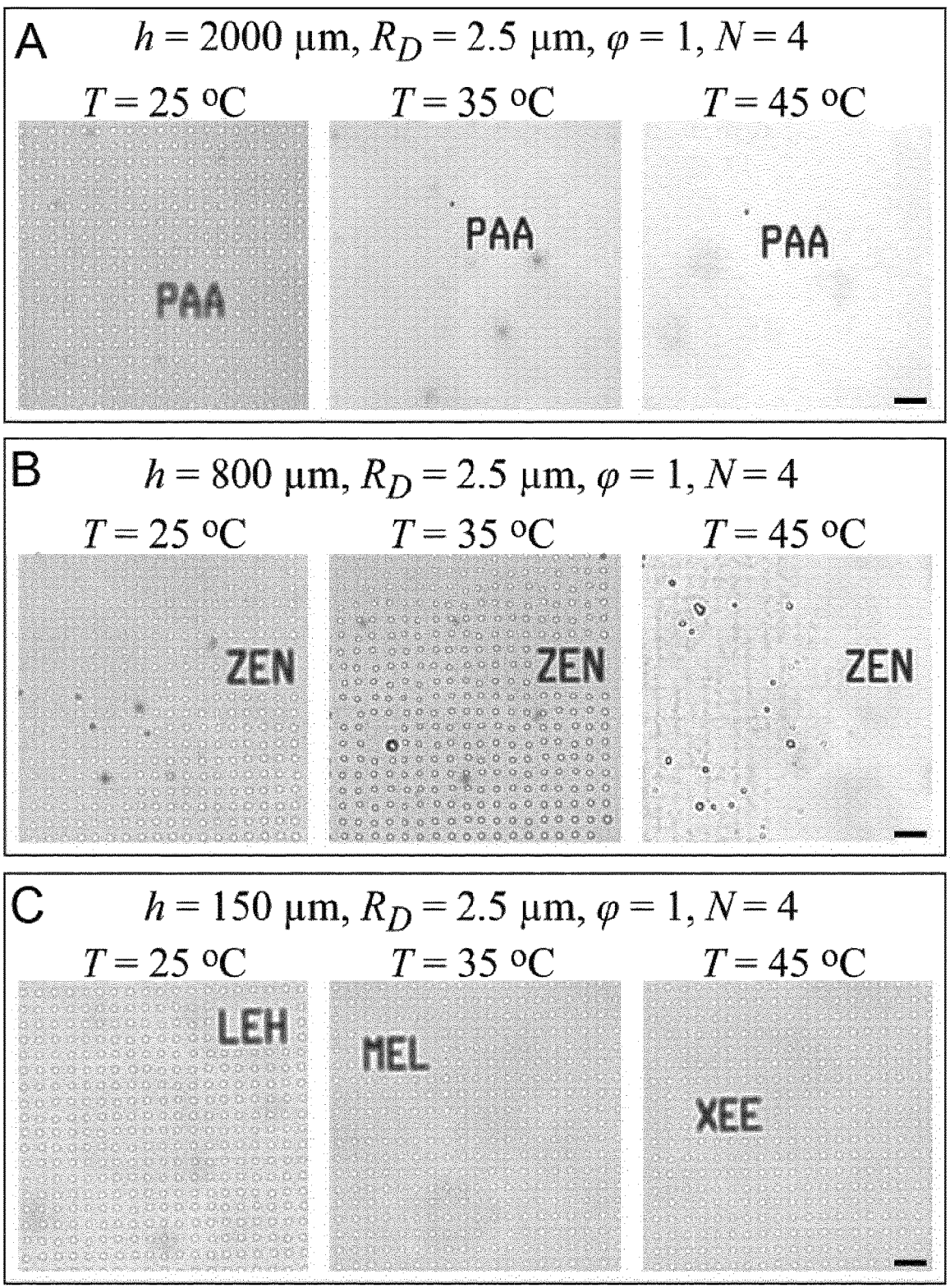
Figure 13:
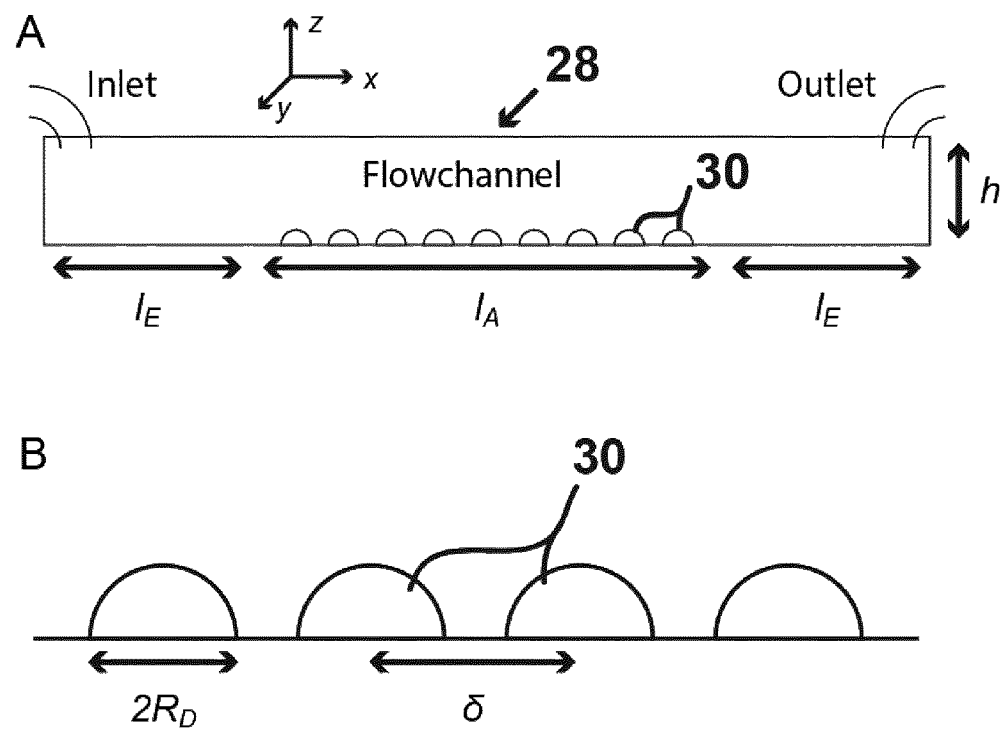
Figure 14:
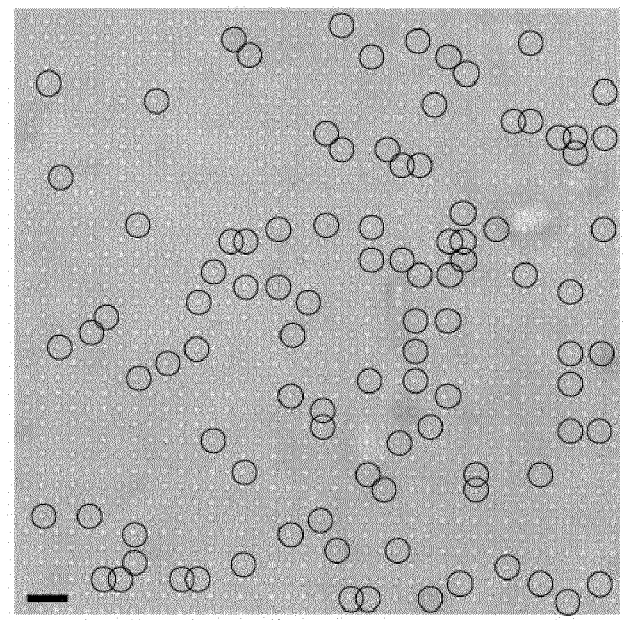
Figure 14:
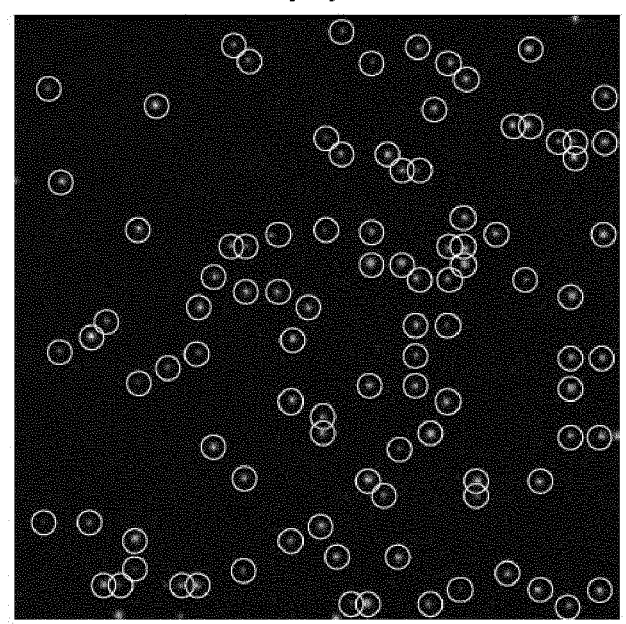
Figure 15:
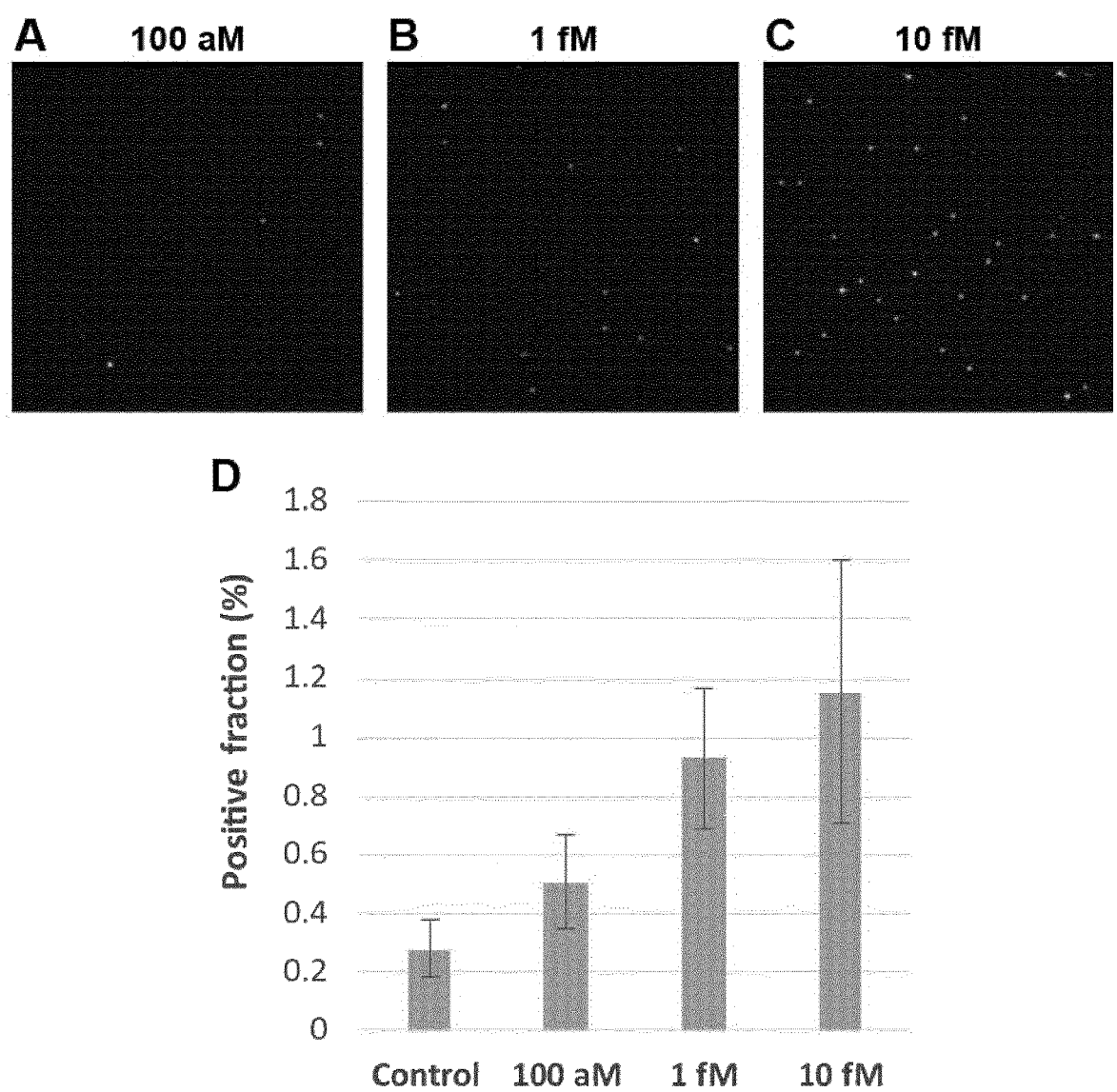
Figure 16:
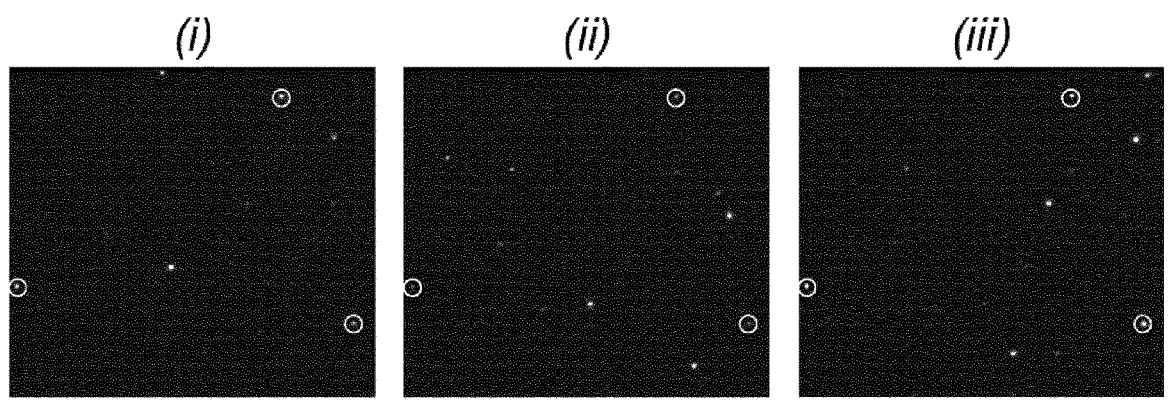

FIG. 8 schematically provides an example of a generic digital counting measurement in which the concentration of analytes from a sample is obtained by analysis of the number of compartments displaying a positive signal;

FIGS. 9A and 9B provide exemplary sketches of SELMA processes based on planar hydrophilic features. In step (A) analytes from a sample is bound in a single step to capture probes situated on a hydrophilic feature. In step (B1) a capture probe residing in the bulk liquid (capture probe part 2) binds to an analyte from the sample, thus in step (B2) leading to the formation of an analyte/capture probe part 2-complex. Step (B3) is subsequent to B2 and shows the binding of the analyte/capture probe part 2-complex to a capture probe residing on a solid support (capture probe part 1). Capture probes part 1 and 2 recognizes each other, and hence forms a capture probe part 1/capture probe part 2/analyte-complex on the solid support, thus immobilizing the analyte on the hydrophilic feature. In step (C) labelling agents are added to the capture probe/analyte-complex, such as to form a capture probe/analyte/labelling agent-complex. In step (D) the capture probe/analyte-complex is labelled by a first part of a labelling agent (labelling agent part 1). In step (E) the capture probe/analyte/labelling agent part 1-complex is secondary labelled by a second part of the labelling agent (labelling agent part 2). In step (F) a functional capture probe/analyte/labelling agent-complex has been formed. In step (G) a liquid droplet is formed on the surface of the hydrophilic feature. The droplet contains detection agents and are protected from evaporation by a gas phase seal. In step (H) the detection agents are converted to molecular reporters by processing of the labelling agent. he sketches are not drawn to scale;

FIG. 10 provides a sketch of an exemplary flow system. The flow system is composed of a rectangular slab comprising five functional elements. Each element is marked with a number and is enclosed by dashed squares. Element 1 is the liquid outlet connected to a pressure source to provide suction. Element 2 is the flow compartment. Element 3 is the liquid inlet connecting the flow compartment to the liquid loading pad. Element 4 is the liquid loading pad shaped as a receptacle for liquid reagents. Element 5 is the droplet region, which presents a pattern of hydrophilic features surrounded by a hydrophobic substrate. The droplet region is situated on the bottom part of the flow compartment. The sketch is not drawn to scale;

FIG. 11 shows an example of the theoretical relationship between evaporation and flowchannel-/droplet-/array-geometry. (A) Plot of Eqn. 17 for an array with droplet radius of 2.5 µm and scaling factors of N=4 and $\varphi$=2, the evaporated fraction will increase as the temperature increases, as well as when the flow channel height increases from 100 µm to 1500 µm. (B) Plot of Eqn. 18 for the maximum height ($h_{MAX}$) as a function of the maximum allowed evaporated fraction ($\theta_{MAX}$) at 35° C. and for various array/droplet geometries. (C) Plot of Eqn. 17 for a flowchannel displaying a height of 100 µm, a scaling factor of $\varphi$=2 and held at a temperature of 35° C. The greater spacing between neighboring droplets (greater N-values) leads to higher evaporated fractions, whereas greater droplet sizes decreases the evaporation;

FIG. 12 demonstrates an example of evaporation resistant micro-droplets under a gas phase seal and the droplet stability for various flowchannel geometries and temperatures. Brightfield micrographs showing droplets formed in flow channels exhibiting heights of (A) 2000 µm, (B) 800

μm and (C) 150 μm. The array parameters were identical for A-C, i.e. droplet radius $R_D=2.5$ μm, excess-to-array length ratio φ=1 and array pitch N=4. The three arrays were prepared in an identical manner: An aqueous solution was infused and withdrawn from the flowchannel and the temperature adjusted to 25° C. After an equilibration time of 30 min., micrographs were acquired and the temperature ramped to 35° C. Again micrographs were acquired after 30 min. equilibration. The procedure was repeated for 45° C. On panel A, droplets are clearly distinguishable only at 25° C. At higher temperatures, the droplets evaporate. On panel B, droplets can be distinguished at 25° C. and 35° C., although the droplet diameters appear to have shrunk due to evaporation. At 45° C. the array is largely disrupted due to evaporation and re-condensation of water-vapor, which indicates that the flowchannel/array had not reached thermal equilibrium at the time when the micrographs were acquired. On panel C, droplets are clearly distinguishable at all temperatures and the droplet diameters appear largely unchanged. Scalebars are 20 μm;

FIG. 13 provides an exemplary sketch of parameters defining (A) an exemplary flow channel 28 and (B) an exemplary micro-droplet array 30 embedded in the flow channel. The sketches are not drawn to scale;

FIG. 14 provides a corresponding pair of brightfield (i) and fluorescence (ii) micrographs for a calibration sample containing 1 pM DNA target. Fluorescence signals were identified as described in Example 4 and were marked with white circles. The positions of the fluorescence signals were applied to the brightfield micrograph and are shown as black circles. It is evident that the positions of the fluorescence signals correspond to the position of the liquid droplets. The scale bar is 10 μm;

FIG. 15 provides three representative fluorescence micrographs from samples containing the following concentration of DNA target; (A) 100 aM, (B) 1 fM and (C) 10 fM. The number of fluorescing droplets were counted for each sample and normalized to the total number of droplets present on the array, such as to provide the percentwise fraction of fluorescing droplets, i.e. the positive fraction. The positive fraction is plotted for samples containing 100 aM DNA target, 1 fM DNA target, 10 fM DNA target as well as a control sample containing no DNA target (D). The values on the bar chart represent average values collected from 5 detection experiments for each sample. The error bars represent the standard deviation of the positive fraction for the 5 identically conducted experiments;

FIG. 16 provides a series of fluorescence micrographs for a sample containing 100 aM target DNA as outlined in Example 5. The first micrograph in the series (i) was acquired after the first detection step, the second micrograph in the series (ii) was acquired on the same position after the second detection step and the third micrograph in the series (iii) was acquired on the same position after the third detection step.

Figure 17:
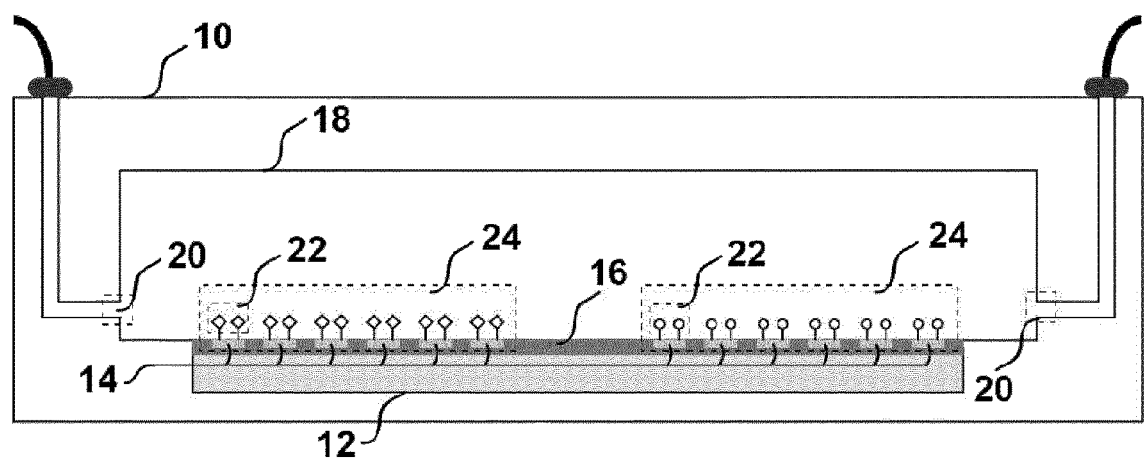

FIG. 17 provides a sketch of a cross-section of an exemplary flow system (10) for digital counting of one or more analytes in a sample comprising a support (12) displaying a pattern of hydrophilic features (14). The pattern is embedded in, placed on or surrounded by a hydrophobic substrate (16) and embedded in a flow compartment (18), which exhibits openings (20). Each hydrophilic feature has capture probes (22) attached to the surface. The support is divided into two regions (24) each region presenting a specific type of capture probe. The sketch is not drawn to scale;

DEFINITIONS

In the present context, the term "digital counting" refers to any analysis in which specific components of a sample are partitioned into compartments at a limiting concentration, such that the number of compartments is greater than the number of specific sample components. In this way, a binary/digital value may be assigned to each compartment depending on whether it is empty (value 0) or whether it is loaded (value 1). In this context, loaded refers to a compartment containing at least one of the specific sample components, whereas empty refers to a compartment containing none of the specific sample components. Digital counting takes place when the number of loaded and empty compartments are evaluated on the basis of a specific signal originating either from the specific sample component itself or from accessory detection reagents coupled to the presence of the specific sample component.

In the present context, the term "digital counting measurement" refers to a digital counting process as defined above, but further includes any mathematical treatment or calibration of the digital counting result, such as to infer the absolute number of specific sample components present in all compartments. This may include (i) accounting for the fact that loaded compartments may contain either 1, 2, 3, etc. copies of the same sample component, or (ii) accounting for the fact that loaded compartments may be falsely classified as empty and vice versa, due to imperfections in the signal generation process. Examples of digital counting measurements include digital polymerase chain reaction (dPCR), single enzyme-linked immunosorbent assay (sELISA) or digital single-enzyme linked immunosorbent assay (dELISA). A sketch of a digital counting measurement process is outlined in FIG. 8.

In the present context, the term "SELMA" is used as an abbreviation for single-enzyme linked molecular analysis and refers to a specific kind of a digital counting measurement. In SELMA, the digital counting measurement takes place in a flow system, in which droplet compartments are organized in a pattern, and specific sample components become immobilized/captured inside the compartments. In this way, sample components may be subjected to several reaction steps without being lost, each reaction step comprised by immersion and withdrawal of solutions or reagents from the flow system. A sketch of exemplary SELMA-processes is provided in FIG. 9.

In the present context "hydrophilic feature" refers to a structure having a first set of material properties surrounded or supported by a solid substrate having another set of material properties. The material properties of the structure and the solid substrate should be adjusted, such that the structure is more wettable than the solid substrate. In other words, the material of which the structure is composed should exhibit a smaller contact angle with water than the solid substrate does. The structure may be defined by chemical and/or physical means. A non-limiting set of possible structures include (i) a closed planar region composed of a more hydrophilic material than the surrounding substrate and (ii) a depression, a protrusion or a combination thereof formed in the surrounding substrate in which one or more of the sides are composed of a more hydrophilic material than the surrounding substrate. Sketches of exemplary hydrophilic features are provided in FIG. 5. In the context of SELMA, hydrophilic features may be manipulated to present suitable reaction compartments for digital counting measurements, e.g. by providing distinct chemical functionality for analyte capture and by providing a pattern of liquid droplets for signal generation and detection.

In the present context, the term "planar hydrophilic feature" refers to a design in which the hydrophobic substrate is planar and the hydrophilic feature embedded in the hydrophobic substrate is planar. The ideal case of planarity is sketched in FIG. 5, however for practical applications planarity would have to be defined in terms of surface roughness. For example, because the hydrophobic substrate and hydrophilic features may be formed from different materials, there might be minute differences in the height between the hydrophobic and the hydrophilic regions. In one embodiment, a suitable criterion for a hydrophilic feature to be considered planar could be that the height difference (alternatively the surface roughness) between the hydrophobic and hydrophilic regions ($\Delta h$) should be negligible compared to the characteristic feature size. In the case of a circular hydrophilic feature having a radius $R_D$, the criterion could be $R_D \gg \Delta h$. In one embodiment, features exhibiting $\Delta h$-values less than 20 nm is considered to be planar.

In the present context, the term "contact angle" refers to the characteristic angle measured at a liquid/vapor/solid interface. In the context where a liquid droplet is deposited on a solid surface in a gas phase, the contact angle is measured through the liquid at a point on the line, where the liquid/vapor interface meets the solid surface. The angle is measured between the solid surface and the tangent of the liquid interface, as defined in the work of W. C. Bigelow, D. L. Pickett and W. A. J. Zisman in "Oleophobic monolayers I: Films adsorbed from solution in non-polar liquids" published in Journal of Colloid Science, vol. 1, pp. 513-538 (1946) (DOI: 10.1016/0095-8522(46)90059-1). A sketch of an exemplary contact angle is provided in FIG. 6.

In the present context, the term "RH" means "the relative vapor saturation of the gas component of the liquid", which is a generalization of the term "relative humidity". Relative humidity is defined as the ratio between the partial vapor pressure of water ($P_W$) to the saturation pressure of water in atmospheric air ($P_{SAT}$) i.e. $RH=P_W/P_{SAT}$. The saturation pressure is here defined as the partial pressure exerted by water vapor in thermal equilibrium with liquid water. The RH-value may be generalized to include other liquids than water. In this case, RH still equals $P_W/P_{SAT}$, but here $P_W$ is to be understood as the partial pressure exerted by the gas component of a given liquid, and $P_{SAT}$ is to be understood as the partial pressure exerted by the gas component in thermal equilibrium with the given liquid. The partial pressures refer to the case, where the gas phase is constituted by several gas species. RH may thus be thought of as an indicator of the vapor saturation level of the corresponding gas phase. That is for RH=0, the gas phase does not contain any gas component of the liquid, whereas for RH=1, the gas phase has taken up the maximum possible content of the gas component of the liquid.

In the present context, the term "RHI" means the "the initial relative vapor saturation of the gas component of the liquid". When the term "the initial relative vapor saturation of the gas component of the liquid" is applied, then it indicates a situation, where change is about to take place, and thus where thermal equilibrium has not been established yet. For example, if a liquid 1, having a characteristic saturation pressure of $P_{SAT}$, is placed in a closed environment containing a gas phase, where the partial pressure of the gas component of liquid 1 is $P_1$, then if $P<P_{SAT}$ liquid will evaporate. The initial relative vapor saturation of the gas component of the liquid is thus $RHI=P_1/P_{SAT}$, because it is calculated prior to any change has taken place. However, once evaporation of liquid 1 starts, the RH-value will gradually increase from the RHI-value until either (i) RH=1 thus saturating the gas phase or (ii) all the liquid has evaporated.

In the present context, the term "maximum droplet volume" refers to the greatest liquid volume a single hydrophilic feature may support if prepared under optimal conditions. In the context of evaporation of liquid from a droplet, then the volume fraction of evaporated liquid is calculated with respect to the maximum droplet volume. A sketch of an exemplary maximum droplet volume for a planar circular hydrophilic feature is provided in FIG. 6.

In the present context, the term "aggregate maximum droplet volume" refers to the sum of volumes obtained by adding together the maximum droplet volumes of a pattern containing a plurality of droplets. In the context of evaporation of liquid from the pattern, then the volume fraction of evaporated liquid is calculated with respect to the aggregate maximum droplet volume.

In the present context, the term "sample" refers to a collection of biological or chemical material, which may or may not have been subjected to laboratory processing. The sample may assume liquid or solid form and may contain specific components, which serve as input for digital counting.

In the present context, the term "analyte" refers to a specific sample component, which may become utilized in a digital counting measurement. An analyte is of biological or molecular nature and is to be (i) separated from the remaining sample material and/or (ii) distinctly manipulated during a digital counting process.

In the present context, the term "capture probe" is a chemical or biochemical agent of molecular nature able to recognize and bind to a specific region of an analyte, such as to retain and/or confine the analyte to a reaction compartment.

In the present context, the term "labelling agent" is a chemical or biochemical agent of molecular nature able to recognize and bind to a specific region of an analyte. The binding region of the labelling agent is different from the binding region of the capture probe, such that during a digital counting measurement a capture probe/analyte/labelling agent-complex may be established. Furthermore, apart from one or more analyte-binding modalities, a labelling agent includes one or more detection-modalities. The term labelling agent may furthermore refer to one or more agents, which when combined together provide an analyte-binding modality and a detection modality.

In the present context, the term "detection modality" refers to a biochemical, chemical, biological or physical moiety able to mediate generation of a signal detectable by a detector. The signal could be optical, electrical or magnetic in nature. Furthermore, the detection modality may rely on a detection agent in order to achieve signal generation.

In the present context, the term "detection agent" refers to a compound, usually of molecular nature, which may change chemical or physical state when contacted by a compatible detection modality. The change of state of the detection agent may be recorded and translated into a signal by a suitable detector. Furthermore, a detection agent which has undergone a change of state may be referred to as a reporter molecule or molecular reporter.

In the present context, the term "detectable concentration" or "minimum detectable concentration" refers to the lowest concentration of a molecular reporter confined to a reaction compartment, which may be detectable by a suitable detector. In order for a concentration to become detectable, the signal resulting from the molecular reporters should exceed that of the noise-level of the detector. In general, a higher concentration of a molecular reporter tends to produce a corresponding higher signal as recorded by the detector.

SPECIFIC EMBODIMENTS OF THE INVENTION

Disclosed herein is a flow system for digital counting of one or more distinct analyte types in a sample comprising a support having a pattern of hydrophilic features in or on a hydrophobic substrate, the hydrophobic substrate being embedded in a flow compartment comprising at least one opening, the hydrophilic features configured to support a plurality of liquid nano-to-attoliter droplets. In an embodiment, the flow compartment is configured to support a gas phase seal reducing evaporation of each nano-to-attoliter droplet. In an embodiment, the gas phase seal reduces evaporation of each nano-to-attoliter droplet to less than 50 percent of the maximum droplet volume.

In an embodiment disclosed herein, the flow system comprises a droplet region providing a pattern of hydrophilic features in or on a hydrophobic substrate to enable formation of evaporation resistant gas-phase-sealed nano-to-attoliter droplets.

In an embodiment disclosed herein, the flow system comprises one or more flow compartments, such as flow channels, overlaying the droplet region to enable liquid contact to the hydrophilic/hydrophobic pattern.

In an embodiment disclosed herein, the flow system comprises a liquid loading pad for supplying the flow compartment and droplet region with liquids and reagents.

In an embodiment disclosed herein, the flow system comprises a liquid inlet connecting the flow compartment to the liquid loading pad.

In an embodiment disclosed herein, the flow system comprises a liquid outlet connecting the flow compartment to a pressure source providing suction, and hence mediate liquid actuation through the flow compartment.

In a further embodiment disclosed herein, the flow system comprises at least five distinct elements in order to function as a single molecule digital counting device, see also FIG. 10.

These are as follows
- A droplet region providing a pattern of hydrophilic features surrounded by a hydrophobic substrate to enable formation of evaporation resistant gas-phase-sealed nano-to-attoliter droplets
- One or more flow compartments overlaying the droplet region to enable liquid contact to the hydrophilic/hydrophobic pattern
- A liquid loading pad for supplying the flow compartment with liquids and reagents
- A liquid inlet connecting the flow compartment to the liquid loading pad
- A liquid outlet connecting the flow compartment to a pressure source to provide suction, and hence mediate liquid actuation through the flow compartment.

The aforementioned five features define an exemplary flow system, where liquid is actuated across the flow compartment by means of a pressure drop from the inlet to the outlet. Instead of applying suction, the liquid reagents in the loading pad may be pushed through the flow channel. This would require the loading pad to be connected on one side to a pressure source and on the other side to the liquid inlet. In this case, the liquid outlet would not be required to be connected to a pressure source. Alternative means of actuating the liquid flow could be by gravity, in which case no pressure source would be necessary, or by dielectrophoretic actuation, which requires electrodes to be embedded in the flow channel. In one embodiment disclosed herein, liquid actuation is suction-driven.

As is known to those skilled in the arts, similar functional flow systems may be fabricated by a multitude of different approaches. These include but are not limited to:
1. Using computer numeric controlled (CNC) milling, injection molding, hot embossing or 3D printing to fabricate flow compartments in solid substrates.
2. Applying any solid substrate compatible with CNC milling, injection molding, hot embossing or 3D printing.
3. Producing the flow system out of one or more components and subsequently bonding the components together to achieve the desired geometry or functionality. Bonding techniques include pressure sensitive adhesive film, spray coating of liquid adhesives, thermal bonding, ultrasonic welding or laser welding. Instead of bonding, the individual components may be mechanically, electromechanically or magnetically clamped such as to produce a final assembly. For an overview of bonding and fabrication processes utilized for microfluidic applications, see the review by Temiz, Y., Lovchik, R., Kaigala, G. V. and Delamarche, E. in "Lab-on-a-chip devices: How to close and plug the lab" published in Microelectronics Engineering, vol. 132, pp. 156-175 (2015) (DOI: 10.1016/j.mee.2014.10.013).

As disclosed herein, the hydrophilic features on the substrate are configured to support a plurality of liquid nano-to-attoliter droplets each having a maximum droplet volume. The hydrophilic surface may be any kind which is capable of holding a droplet having that maximum droplet volume. I.e. as long as a droplet of that maximum volume will remain on a hydrophilic feature, the hydrophilic feature is configured to support such a droplet.

In an embodiment disclosed herein, the droplet region consists of a pattern of hydrophilic features surrounded by a hydrophobic medium. In this embodiment, the geometry of a hydrophilic feature, the physical/chemical properties of the liquid and the hydrophobic substrate determine the maximum droplet volume, which a single feature is able to retain, such that the liquid does not contact the surrounding hydrophobic medium. One way to experimentally determine the maximum droplet volume would be to deposit increasing amounts of liquid onto an initially dry hydrophilic feature. Liquid deposition could be conducted with the aid of an automated micro-dispenser, or in the case of micron-sized features with the aid of a piezo-actuated micro-manipulator, but should be done in a humidified chamber, such that evaporation cannot take place. Furthermore, with the aid of a microscope, the footprint of the deposited droplet may be measured. Consequently, once the measured footprint transgresses the perimeter defined by the hydrophilic feature the maximum droplet volume has been reached and exceeded.

Apart from the experimental approach, the maximum droplet volume may also be estimated from a simple theoretical model. In this case, it is to be assumed that the hydrophilic feature is circular having a radius of $R_D$, and that the liquid exhibits a contact angle of $\gamma$ when in contact with the hydrophobic medium, and that the droplet rests on a planar surface, see FIGS. 5-6. It is further assumed, that the droplet is sufficiently small such that gravity does not affect the shape of the droplet significantly. When liquid is deposited onto the hydrophilic feature, it will spread out to the perimeter and the liquid will hence form a contact angle $\alpha$. The contact angle a is defined as the angle, the tangent to the droplet surface forms with the planar hydrophilic surface at the perimeter. As the volume of the droplet increases, so does $\alpha$, but only to a certain point. If $\alpha$ exceeds $\gamma$, it will be energetically more favorable for the droplet to spread onto the hydrophobic medium, thus transgressing the hydrophilic perimeter. Consequently, at the maximum droplet volume α equals γ, and the volume ($V_D$) may be obtained from the geometrical description of a capped sphere as $$V_D = \pi R_D^3 G(\gamma) \quad \text{Eqn. 1}$$

$$G(\gamma) = \frac{2 - 3\sin\left(\frac{\pi}{2} - \gamma\right) + \sin^3\left(\frac{\pi}{2} - \gamma\right)}{3\cos^3\left(\frac{\pi}{2} - \gamma\right)}$$

For γ-values sufficiently close to 90°, Eqn. 1 may be further simplified by assuming the droplet to be a semi-spherical cap, thus exhibiting a $V_D$-value of $$2\pi R_D^3/3.$$

In yet another case, where the hydrophilic feature is shaped as a circular cavity with radius $R_D$ and depth d, then the maximum volume is found by adding the cavity volume of $\pi d R_D^2$ to Eqn. 1.

In one embodiment, the hydrophilic features are configured to support the nano-to-attoliter droplets and the liquid exhibits a contact angle on the hydrophobic substrate of at least 90 degrees and at most 150 degrees. In one embodiment, the hydrophilic features are configured to support the nano-to-attoliter droplets having a radius ($R_D$) of at least 0.1 µm and at most 100 µm.

Even though a number of approaches can be taken to fabricate an array of hydrophilic features surrounded by a hydrophobic medium, the most readily applicable one would involve photolithography. Photolithography is able to accurately produce micron-sized chemical and/or physical structures, and relies on coating of a flat wafer substrate with a photosensitive thin film. In subsequent steps the thin film is selectively removed by exposure to high-intensity ultraviolet light through a photomask providing the intended pattern. Sketches of exemplary fabrication processes are provided in FIG. 7. However, due to the optical resolution of UV photolithography, it remains technically challenging to accurately produce features below 0.1 µm. In the case, where the patterned hydrophilic feature is planar circular and exhibits an $R_D$-value of 0.1 µm, the corresponding maximum droplet volume would be $V_D$=2.9 attoliter for a γ-value of 90° and would be $V_D$=33.1 attoliter for a γ-value of 150°, according to Eqn. 1.

Hydrophilic features exhibiting $R_D$-values down to 0.1 µm allows for highly dense arrays, which in the context of single molecule digital counting translates into (i) extended dynamic range and (ii) faster detection times.

The extended dynamic range is due to the fact that for digital counting, the number of droplet compartments present in the measurement determines the signal linearity. The signal is considered linear until all droplet compartments produce a signal, i.e. the array has been saturated. For example, a regular rectangular array covering 10 mm×10 mm having a $R_D$-value of 0.1 µm and an inter-feature spacing of 0.4 µm would host 625 million droplets, thus exhibiting a linear dynamic range spanning approximately 8 orders of magnitude.

The faster detection time relies on the fact that for digital counting, the molecular reporter is usually produced by an enzyme or an enzymatically coupled system. In this embodiment, the single enzyme produces a signal by the repeated conversion of a non-fluorescent/-chemiluminescent/-colorimetric molecule into a fluorescing/luminescing/absorbing one (the molecular reporter). The minimum detectable concentration of the reporter molecule depends on the droplet volume; the smaller the volume is, the faster the concentration is reached, assuming a constant enzymatic turnover rate.

On the other hand, droplets exhibiting larger volumes in the nanoliter range (e.g. a circular planar hydrophilic feature with a $R_D$-value of 100 µm has a maximum volume of 2.1 nanoliter for a γ-value of 90° and a maximum volume of 33.1 nanoliter for a γ-value of 150°) would be advantageous in situations, (i) where a large dynamic range is not necessary, e.g. the analyte concentration is expected to be too low to saturate the array or (ii) where sub-nanoliter droplets cannot be resolved by the imaging sensor.

Alternatively, nanoliter volume droplets may be used for arraying and organizing larger biological entities such as cells, cell fragments, virus particles, vesicles, organelles, etc. prior to a measurement.

In one embodiment, the hydrophilic substrate is a glass, a hydrophilic polymer or a metaloxide compound.

The main requirement for the hydrophilic substrate is that the liquid should form a contact angle on it, which is less than for the hydrophobic substrate. Furthermore, the substrate should preferably be amenable to micro-fabrication approaches, such as photolithography, soft lithography or micro-imprinting. Silicondioxide and pure and doped variants thereof is a suitable choice for this purpose, not only because it serves as a well-characterized substrate for photolithography, but also because a great number of chemical and biochemical surface functionalization protocols are available. For example, is a wide range of silane compounds commercially available (e.g. see "Silane coupling agents, version 3.0" as published by Gelest Inc.), which may be used for straightforward derivatization of silicondioxide surfaces. Although silanization is most efficient for materials presenting silanol groups at their surface, such as silicondioxide, many other materials may be amenable to this process. These include but are not limited to aluminum, aluminosilicates, silicon, copper, tin, talc, inorganic oxides (e.g. ferrous oxides, titaniumoxide, chromiumoxide), steel, iron, nickel and zinc.

Upon silane derivatization of a substrate, a new chemical functionality is introduced to the material and hence liquid may exhibit altered contact angles on the substrate after functionalization. For this reason, an initially hydrophilic substrate such as glass might be rendered hydrophobic by functionalization with a hydrophobic silane moiety, e.g. a fluorocarbon silane. Alternatively, an initially slightly hydrophilic substrate might be rendered even more hydrophilic by functionalization with a highly hydrophilic silane moiety, e.g. a poly(ethylene glycol) silane. This is well known to those skilled in the art, and thus the liquid/solid contact angle, which is referred to in this document only relates to the resulting liquid/solid contact angle subsequent to any surface modification of any initial substrate material.

Silane-derivatization of inorganic substrates constitutes only one out of many procedures to introduce new chemical function to a substrate. Another approach includes adsorption of monothiolated compounds to gold substrates, such as to produce a self-assembled monolayer. Yet another approach, which is amenable to soft organic substrates, such as plastics would be plasma polymerization, in which thin layers of a desired chemical polymer is deposited on the plastic surface from a plasma of the corresponding monomers.

The configuration of the hydrophilic features may relate to at least one of:
- the hydrophilicity of the material constituting the hydrophilic feature;
- the hydrophobicity of the material constituting the hydrophobic substrate;
- the area of the feature; and
- the thickness of the feature In one embodiment, the maximum droplet volume is $V_D$ as calculated by Eqn. 1. Accordingly, the hydrophilic features may be provided such that a droplet of this volume can be held at each of the hydrophilic features.

As examples of how to get from the maximum droplet volume to the specific configuration of the individual hydrophilic feature, the following steps may be carried out by 1. First choosing a suitable droplet volume for the application at hand, cf. the aforementioned discussion on droplet volumes.
2. Next, obtain the solid/liquid contact angle y for the liquid applied in the present application.
3. Next, decide on a desired geometrical shape of the hydrophilic feature, i.e. a circle, a square, a hexagon, etc. The shape is likely to depend on the fabrication procedure applied to produce the pattern.
4. Calculate the relationship between the perimeter length of the particular shape from step 3 and the corresponding maximum droplet volume. In the case of a circular shape, the relationship is provided in Eqn. 1. For other geometrical shapes, the relationship would have to be derived in a similar fashion as that stated for the derivation of Eqn. 1.
5. Obtain the perimeter length corresponding to the chosen droplet volume from the relationship in step 4. In the case of a circular shape, it is sufficient to solve Eqn. 1 for $R_D$.

In a further embodiment, the configuration of the flow compartment in which the pattern of hydrophilic features resides needs to be determined in order to provide a functional gas phase seal to reduce evaporation from the micron-sized droplets. For example, if an attoliter aqueous droplet is deposited on a substrate at ambient conditions, it will evaporate within seconds due to the high surface/volume ratio. Consequently, for applications where droplet contents need to be measured, the droplets are required to be stable for extended periods of time, and hence evaporation should be greatly reduced or completely negated.

In a further embodiment disclosed herein, is a flow compartment hosting a pattern of hydrophilic features, the hydrophilic features configured to support droplets of a certain maximum volume as described above, wherein the flow compartment exhibits a volume $V_C$ and the maximum attainable aggregate volume of a droplet-bearing hydrophilic pattern is denoted $V_{DA}$. If the pattern hosts a number of droplets ($N_D$) each exhibiting the same maximum droplet volume ($V_D$), then $V_{DA}=V_D \cdot N_D$. If the pattern hosts droplets of varying sizes, then the corresponding $V_{DA}$-value is given as $$V_{DA} = \sum_{i=1}^{N_D} V_{D,i} \qquad \text{Eqn. 2}$$

where $V_{D,i}$ is the maximum volume of the i'th droplet on the pattern. Consequently, the corresponding molar amount of liquid ($n_{DA}$) is then $$n_{DA} = \frac{V_{DA}\rho_L}{M_W} \qquad \text{Eqn. 3}$$

where $M_W$ is the molar weight of the liquid and $\rho_L$ is the density of the liquid. If all droplets were to evaporate completely, and assuming the evaporated vapor behaves as an ideal gas, the resulting vapor would produce a corresponding vapor pressure ($P_{VAP}$) in the flow compartment given as $$P_{VAP} = \frac{n_{DA}RT}{V_C} \qquad \text{Eqn. 4}$$

where R is the molar gas constant and T is the temperature. However, complete droplet evaporation is only possible for $V_C \gg V_{DA}$, because in that case the amount of vapor produced by complete droplet evaporation would not change the initial vapor pressure of the flow compartment significantly. However, for a flow compartment volume approaching that of $V_{DA}$, the droplet vapor would increase the pressure in the flow compartment until the saturation vapor pressure ($P_{SAT}$) has become established. Once $P_{SAT}$ has been reached further evaporation is not possible. The $P_{SAT}$-value, i.e. the vapor pressure exerted by the gas-component of the liquid at thermodynamic equilibrium, is given by the Clausius-Clapeyron equation as $$P_{SAT} = P_0 \exp\left(\frac{\Delta H_{VAP}}{R}\left(\frac{1}{T_0} - \frac{1}{T}\right)\right) \quad \text{Eqn. 5}$$

where $\Delta H_{VAP}$ is the enthalpy of evaporation of the liquid and $P_0$ is a reference vapor pressure of the liquid at a corresponding reference temperature $T_0$.

Consequently, the maximum allowed molar amount of liquid able to evaporate ($n_{VAP}$) can be obtained from the ideal gas equation as $$n_{VAP} = \frac{V_C P_{SAT}}{RT} = \frac{V_c P_0}{RT} \exp\left(\frac{\Delta H_{VAP}}{R}\left(\frac{1}{T_0} - \frac{1}{T}\right)\right) \quad \text{Eqn. 6}$$

For $n_{VAP} \geq n_{DA}$ complete droplet evaporation takes place. An expression for the maximum flow compartment volume ($V_{MAX}$), i.e. the greatest possible flow compartment volume where droplets are not completely evaporated, may now be obtained as $$n_{VAP}(V_c = V_{MAX}) = n_{DA} \Rightarrow \quad \text{Eqn. 7}$$

$$V_{MAX} = V_{DA} \frac{\rho_L RT}{M_W P_0} \exp\left(\frac{\Delta H_{VAP}}{R}\left(\frac{1}{T} - \frac{1}{T_0}\right)\right)$$

Consequently, any flow compartment able to host a functional and long-term stable droplet pattern should be configured such that $V_C < V_{MAX}$.

The expression in Eqn. 7 refers to a state of equilibrium. The paths to equilibrium are numerous, but may be described as; (i) a pattern of hydrophilic features are contacted with liquid such as to produce a pattern of droplets, each droplet initially exhibiting the maximum possible volume, (ii) liquid will evaporate from the droplets until the saturation pressure is established in the flow compartment and (iii) the droplets, now having a reduced volume due to the evaporation, remain stable.

Importantly, the pattern needs to be contacted with liquid in a suitable fashion to produce a functional gas phase seal. For example, by actuating a liquid plug across the pattern, thus depositing liquid micro-droplets on the hydrophilic features. Once the liquid plug has contacted all features on the array, the liquid inlet and outlet needs to be blocked such as to provide a closed environment. This may be achieved in a number of ways, for example (i) by having installed valves at the liquid inlet and outlet or (ii) by synchronizing the liquid flow such that the first liquid plug is followed by a second plug, the first one being actuated to the liquid outlet and then stopped, the second being actuated into the liquid inlet, thus blocking inlet and outlet with liquid. In this way, the evaporated liquid from the droplets will establish the saturation pressure in the flow compartment and hence become evaporation resistant. This is exemplified in Examples 1 and 2.

Furthermore, in Eqn. 7 and the following discussion, it was assumed that the gas phase in which the flow system is prepared did not contain any evaporated liquid (i.e. the gas-component of the liquid) prior to contacting the pattern of hydrophilic features with liquid. However, this may not always be the case. For example, in the case where the liquid is water and the gas phase is atmospheric air, the air may initially contain a certain fraction of water vapor. For atmospheric air, the relative humidity (RH) provides the water vapor pressure relative to the saturation pressure, i.e. $RH=P_W/P_{SAT}$, where $P_W$ is the partial pressure of water vapor in atmospheric air. If the initial relative water vapor saturation of the atmospheric air (RHI) is equal to 0, the air will have no water vapor content and hence Eqn. 7 may be applied. On the other hand, if RHI>0, Eqn. 7 requires modification, because less of the liquid droplet needs to evaporate in order to establish the saturation pressure, thus cf. Eqn. 6

$$n_{VAP} = \frac{V_C}{RT}(1 - RHI)P_{SAT} = \frac{V_C(1-RHI)P_0}{RT}\exp\left(\frac{\Delta H_{VAP}}{R}\left(\frac{1}{T_0} - \frac{1}{T}\right)\right) \quad \text{Eqn. 8}$$

This translates into the following solution for $V_{MAX}$:

$$V_{MAX} = V_{DA}\frac{\rho_L RT}{(1-RHI)M_W P_0}\exp\left(\frac{\Delta H_{VAP}}{R}\left(\frac{1}{T} - \frac{1}{T_0}\right)\right) \quad \text{Eqn. 9}$$

In the present context, RHI is to be understood as general as possible, i.e. thus not only relating to water, but also to any other liquid (see the above section on Definitions). In this case, the more general definition of RHI is $RHI=P_L/P_{SAT}$, where $P_L$ is the initial vapor pressure of the gas component of the liquid applied. The $P_L$-value refers to the gas phase in which the flow system is used prior to the formation of the droplet array. The gas phase seal becomes established once the saturation pressure is reached inside the flow compartment. Thus, locally in the flow compartment, the RH-value will rise from the initial value to 1, indicating complete saturation and a functional gas phase seal.

In one embodiment, the flow compartment disclosed herein has a volume ($V_C$), where the volume ($V_C$) is greater than the aggregate maximum droplet volume ($V_{DA}$) of all liquid nano-to-attoliter droplets and is less than $V_{MAX}$ as calculated in Eqn. 9.

In an embodiment as disclosed herein, to obtain the optimal configuration of a flow system for digital counting of analytes comprising a pattern of hydrophilic features in or on a hydrophobic substrate, it is necessary to consider (i) the configuration of the individual hydrophilic feature, (ii) the configuration of the pattern of the features and (iii) the configuration of the compartment in which the pattern is residing. Collectively, these three configurations provide the flow system with the ability to maintain an evaporation resistant pattern of micro-droplets by way of a gas phase seal. The configuration of the individual hydrophilic feature has been outlined above. Exemplary next steps to determine the flow system configuration is as follows:

1) Decide on the total number of droplets required for the application. As discussed above, the total number of droplets determines the dynamic range of the measurement, and should thus be matched to the expected concentration range of the analyte.
2) The $V_{DA}$-value for the pattern may now be calculated from Eqn. 2, thus providing the lower bound for the flow compartment volume, i.e. the $V_C$-value.
3) Determine the nominal molar weight ($M_W$) and the volume density ($\rho_L$) of the liquid applied, as well as the temperature (T) and RHI-value at which the measurement will take place. Apply a suitable set of values for the reference temperature, pressure and enthalpy of vaporization to calculate the $V_{MAX}$-value for the flow compartment volume using Eqn. 9. For example, is $P_0=1.0$ atm at $T_0=373$ K for water, which exhibits a $\Delta H_{VAP}$-value of 40.7 kJ/mol.
4) Decide on the specific arrangement of the pattern of hydrophilic features, e.g. a square lattice array, a hexagonal lattice array, a rectangular lattice array, a rhombic lattice array, etc. The preferred array geometry will usually be determined by the fabrication method. Decide on the length and width of the array in order to accommodate the total number of droplets.
5) Decide on the flow compartment geometry, e.g. a rectangular channel, a circular channel, a semi-circular channel, etc. The preferred array geometry will usually be determined by the fabrication method.
6) Scale the flow compartment geometry, such that the total volume is less than $V_{MAX}$. An example of this is provided in Example 2. Briefly, in the case of a rectangular channel, the total volume is given as the width×length×height of the channel. The width and length of the channel could for example be matched to that of the array, thus leaving the height variable. The height may thus be chosen to provide a total volume less than $V_{MAX}$.

In a further embodiment disclosed herein, is a flow system wherein the hydrophilic features are circular having a radius ($R_D$), and where the maximum droplet volume ($V_D$) a single hydrophilic circle can support is provided in Eqn. 1.

In an embodiment, the evaporation of each nano-to-attoliter droplet is less than 50 percent, less than 40 percent, less than 30 percent, less than 20 percent, less than 10 percent, less than 5 percent, less than 1 percent of the maximum droplet volume of each nano-to-attoliter droplet.

For a given configuration of the flow system, i.e. a specified set of $V_C$- and $V_{DA}$-values, the corresponding evaporated fraction $\theta_{VAP}$ may be calculated. The evaporated fraction is defined as the droplet volume fraction evaporated into the gas phase, i.e. $\theta_{VAP}=n_{VAP}/n_{DA}$. Inserting Eqn. 3 and Eqn. 8 in to this expression yields $$\theta_{VAP} = \frac{(1-RHI)V_C}{RT} \frac{M_W}{V_{DA}\rho_L} P_{SAT} = \qquad \text{Eqn. 10}$$

$$\frac{V_C}{V_{DA}} \frac{(1-RHI)M_W P_0}{\rho_L RT} \exp\left(\frac{\Delta H_{VAP}}{R}\left(\frac{1}{T_0} - \frac{1}{T}\right)\right)$$

If $\theta_{VAP}$ assumes values greater than 1, then the entire droplet array has evaporated due to e.g. a too large flow compartment volume, too few droplets on the array, a too high temperature, a too small hydrophilic feature, etc. On the other hand, if $\theta_{VAP}$ is less than 1, then the gas phase seal is considered functional, because intact droplets—although exhibiting a reduced volume—may remain on the hydrophilic features.

In principle, any gas known to the skilled person able to seal the droplets against evaporation may be used. Examples of a gas phase seal is atmospheric air, nitrogen, argon or helium or mixes thereof. In one embodiment, the gas phase seal is provided by atmospheric air, nitrogen, argon or helium. In a further embodiment, the gas phase seal is provided by atmospheric air.

A digital counting measurement allows single analyte molecules to become directly detected, and hence counted to determine their concentration in a sample. Digital counting measurements are applied in digital polymerase chain reaction (dPCR), digital enzyme-linked immunosorbent assay (dELISA) and variant thereof. For dPCR single nucleotide analytes are isolated in reaction compartments and subjected to polymerase-assisted nucleotide amplification and fluorescence labeling of the amplicons. For dELISA single protein/peptide analytes are captured on the surface of micro-colloid particles, labelled with enzyme-conjugated antibodies, isolated in microscopic reaction compartments and supplied with detection reagents. The detection reagents produce an optical signal (e.g. fluorescence, chemiluminescence, absorbance) when processed by the enzyme, which due to the microscopic volume of the reaction compartment rapidly reaches a detectable concentration. The principle of a digital counting measurement is outlined in FIG. 8.

In an embodiment disclosed herein, to conduct a digital counting measurement of a given analyte using the flow system as described herein, at least the following three general steps are required; (1) analyte capture, (2) analyte labelling and (3) analyte counting, see for example the sketch in FIG. 9. In step 1, analytes from a sample become specifically captured on the hydrophilic features. In step 2, the captured analytes become specifically labelled with a suitable agent, e.g. an enzyme-conjugate. In step 3, an array of micro-droplets is formed such that the liquid contains a detection agent. In the case where the labelling agent is an enzyme, the detection agent could be a fluorogenic-/chromogenic-/chemiluminescent substrate for the enzyme. Upon processing of the substrate a detectable optical signal is produced in droplets, which initially harbored both the labelling agent and the detection reagent. Next, droplets producing a signal may be counted by optical imaging of the array.

In one embodiment, the flow system comprises one or more capture probes for one or more distinct analyte types, the capture probe(s) being attached to the hydrophilic features. In a further embodiment the different types of capture probes are arranged in regions.

An advantage of the present invention over that of dPCR and micro-colloid assisted dELISA is that analytes may become captured and organized specifically on the hydrophilic features. This is appreciated when it comes to (i) measuring several different analyte types in a single measurement and (ii) if a repeated measurement is desired.

In the first case, different capture probes may be placed on different regions in the flow compartment, such that a capture probe specific to one analyte type is localized in a first region, another capture probe specific to another analyte type is localized in a second region and so forth. This is a well-known strategy in the field of DNA- and protein-microarray studies in which several hundred target analytes can be detected in a single measurement, see for example the review by Weinrich, D. et al entitled "Applications of Protein Biochips in Biomedical and Biotechnological Research" published in *Angewandte Chemie International Edition* (2009), vol. 48, pp. 7744-7751. (DOI: 10.1002/anie.200901480).

In the second case, it is possible to repeat the digital counting by removing labelling and detection agents and re-introducing them to the flow system. Because the captured analytes remain immobilized on the hydrophilic features, the digital counting measurement may be repeated in order to improve e.g. the signal-to-noise ratio, see Example 5. This is not possible for either dPCR or dELISA, because labelling and detection agents cannot be removed without also removing the analytes.

In one embodiment, the one or more capture probes for one or more distinct analyte types are attached to the hydrophilic features by a linker moiety. The linker molecule serves to connect the—in most cases—hard inorganic surface of the hydrophilic features to the soft organic capture probes. Linker molecules may thus contain a dual chemical functionality in order to connect the capture probe to the surface. Linker molecules may be chosen to be poly(ethylene-glycol) polymers, which are flexible, inert and hydrophilic. They may also be chosen to be linear alkane chains. Poly(ethylene glycol) linkers may be prepared in different sizes/lengths and hence provide a greater separation between the surface and the capture probe, whereas alkane chains are generally shorter. Other linker molecules include but are not limited to polypeptides or oligonucleotides. The chemical functionality present on the linker molecule may be chosen from a great selection of reactive chemical groups such as aldehyde, alkyne, amine, azide, biotin, Boc/Fmoc-protected amine, carboxylic acid, epoxides, hydrazide, hydroxyl, maleimide, N-hydroxysuccinimide, thiols, vinylsulfones and variants thereof.

In one embodiment, more than one type of capture probes is attached to the hydrophilic features, and the different types of capture probes are arranged in regions. In one embodiment, the capture probes are selected from the following group of probes: oligonucleotides, proteins, peptides or synthetic variants thereof.

In the case where the capture probe is an oligonucleotide, the probe may be able to capture other oligonucleotides, which display a complementary sequence to that of the capture probe. Synthetic oligonucleotide variants, such as locked nucleic acids (LNA) or peptide nucleic acids (PNA), which exhibit strand-invading properties may also be utilized to capture single- or double-stranded DNA. Aptamers too may be utilized as capture probes to enable the capture of proteins or peptides. Furthermore, antibodies or fragments of antibodies may become used as capture probes in order to mediate specific capture of proteins, peptides or small molecules.

In one embodiment, the hydrophobic support having the pattern of hydrophilic features substrate is planar. In a further embodiment, the pattern of hydrophilic features comprises at least one region in which the hydrophilic features are arranged in an array.

In an embodiment, the hydrophilic features are organized in a quadratic planar array, the features being shaped as circles having a radius ($R_D$), the array having a pitch ($\delta$) between neighboring features, where $\delta$ is at least $3R_D$, the array extending a length ($L_{AX}$) along the flow direction, the array extending a length ($L_{AY}$) perpendicular to the flow direction, the channel having a length ($L_{CX}$) along the flow direction, where $L_{CX}$ is greater than or equal to $L_{AX}$, the channel having a length ($L_{CY}$) perpendicular to the flow direction, where $L_{CY}$ is greater than or equal to $L_{AY}$, the channel having a height (h), which is at least $2R_D$ and at most $h_{MAX}$, where $h_{MAX}$ is calculated from the following equation $$h_{MAX} = \theta_{MAX} \frac{L_{AX} L_{AY}}{L_{CX} L_{CY} \delta^2} \frac{\rho_L RT}{(1-RHI) M_W P_0} \exp\left(\frac{\Delta H_{VAP}}{R}\left(\frac{1}{T} - \frac{1}{T_0}\right)\right) V_D(R_D, \gamma) \qquad \text{Eqn. 11}$$

where $\theta_{MAX}$ is the maximum acceptable evaporated volume fraction of the droplets and $V_D(R_D, \gamma)$ is the maximum droplet volume according to Eqn. 1. In order to arrive at Eqn. 11, it is necessary to consider Eqn. 10, which expresses the evaporated fraction ($\theta_{VAP}$) as a function of the flow compartment volume ($V_C$) and the maximum aggregate volume of the droplet array ($V_{DA}$). For a flow compartment exhibiting the abovementioned geometry, the flow compartment volume is $V_C = h L_{CX} L_{Cy}$ and the maximum aggregate droplet array volume is $V_{DA} = V_D(R_D,\gamma) L_{AX} L_{AY} \delta^{-2}$. One approach to establishing a functional configuration of the flow compartment in order to provide a gas phase seal is to set the maximum acceptable evaporated volume fraction of the droplets to a suitable value, e.g. $\theta_{MAX}=0.05$. Next, by leaving the flow compartment height as the only variable parameter, the maximum allowed height ($h_{MAX}$) may be obtained by inserting $V_C=V_{MAX}=h_{MAX}L_{CX}L_{CY}$, $V_{DA}$ and $\eta_{MAX}$ into Eqn. 10 and solving for $h_{MAX}$, thus arriving at the result in Eqn. 11.

In one embodiment, the pattern of hydrophilic features comprises at least two regions, and the array of one region differs from the array of another region.

In the case where the hydrophilic features are configured to support droplets of various sizes, the calculation of $h_{MAX}$ in Eqn. 11 should be carried out using the $V_D$-value corresponding to the smallest of the droplet volumes on the pattern. In this way, both the smallest and largest droplets on the array may remain stable without evaporating more than set forth by the $\theta_{MAX}$-value.

In one embodiment, the support for the hydrophilic features is located centrally within the flow compartment.

Even though a central location in the flow compartment of the array comprising the hydrophilic features would usually be the preferred, the exact location of the array does not influence the results of the previous calculations. This is due to the calculations are based on the assumption that thermodynamic equilibrium becomes established within the flow compartment, i.e. an equilibrium where the evaporation rate from the liquid droplets supported by the hydrophilic features equals the condensation rate of the vapor in the flow compartment onto the droplets. However, a centrally located array may reach equilibrium faster compared to a decentrally located one due to the transport kinetics of vapor within the compartment.

In one embodiment, the number of hydrophilic features is at least 1,000, at least 10,000, at least 100,000, at least 1,000,000, at least 10,000,000.

In one embodiment, the hydrophobic layer is a molecular monolayer covalently grafted to the substrate. In one embodiment, the hydrophobic layer is a molecular monolayer chemisorbed on a metal substrate.

In one embodiment, the flow compartment is channel shaped and forms a flow direction between two openings in opposite ends of the flow compartment. In one embodiment, the flow compartment and the openings have a rectangular shape in a cross section perpendicular to the flow direction. In one embodiment, the flow compartment has a rectangular shape and the openings have a circular shape in a cross section perpendicular to the flow direction.

In one aspect disclosed herein is a method of preparing a flow system.

To provide an overall understanding of the invention, certain illustrative embodiments will now be described, including a system that supports an array of microdroplets to allow sELISA analysis of an enzyme. However, it will be understood by one of ordinary skill in the art that the systems and methods described herein can be adapted and modified for other suitable applications and that such other additions and modifications will not depart from the scope hereof.

Figure 1:
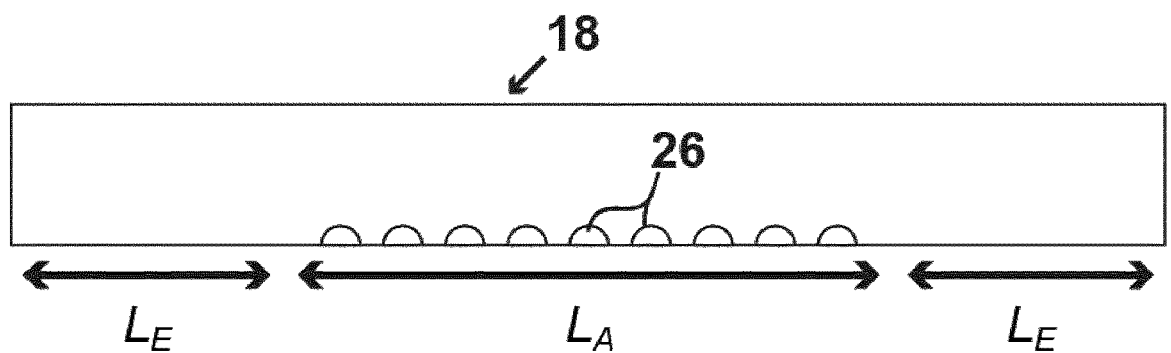
FIG. 1 depicts one example of a flow compartment 18 having a plurality of microdroplets 26. The sketch is not drawn to scale.

FIG. 1 depicts one embodiment of a system for supporting a plurality of microdroplets with reduced rate of evaporation. Specifically, FIG. 1 illustrates a system 18 wherein a rectangular flow compartment houses a plurality of microdroplets. The microdroplets are placed on a bottom surface of the flow compartment. Each end of the flow compartment is open to the ambient environment.

Figure 2:
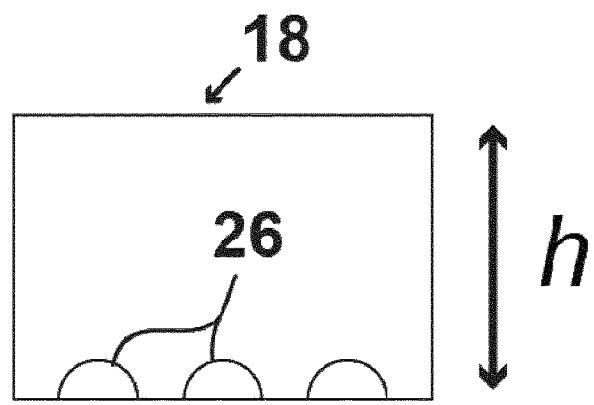
FIG. 2 depicts one example of an end of the flow compartment 18 in FIG. 1. The sketch is not drawn to scale.

FIG. 2 is a cross-sectional view of an end of the flow compartment. FIG. 2 shows that for this embodiment the end is square in shape of height h (depicted by the vertical arrow). Returning to FIG. 1, it is shown that each end of the array of microdroplets is spaced a distance $L_E$ (illustrated by the double arrow) from the end of the flow compartment.

The flow compartment of FIG. 1 is a flowchannel that supports an array of microdroplets. The microdroplets may be inserted into the flowchannel using any known technique. The dimensions of the depicted flowchannel can be generally understood from FIG. 1 and are characterized by the height h, of the channel, $L_A$, which is the length of the flowchannel covered by the array of microdroplets, $L_E$, which is the length of the channel that separates the microarray from the inlet and the outlet (and not supporting any portion of the array of microdroplets). Given the length and height and shape of the flowchannel, it is possible to calculate the volume of that flow channel. Details of one such calculation are set out in Example 2.

Each droplet is essentially a hemisphere and can be modeled as such. The hemispherical droplet will have a radius. The drops are spaced apart essentially a standard pitch. The dots may be in a linear array, a square array, or any other suitable arrangement. It is of course possible to estimate the total aggregate volume of liquid contained in the array of microdroplets as a function of the radius and the number of droplets. Details of one such calculation are set out in Example 2.

Figure 3:
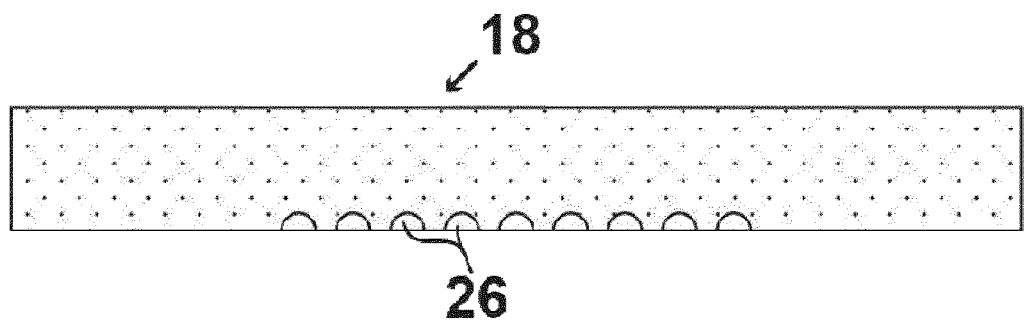
FIG. 3 depicts an exemplary representation of a flow compartment 18 with a vapor phase forming a gas seal. The sketch is not drawn to scale.

Once the geometry of the flowchannel is known, the available volume can be calculated. The volume and the equilibrium water vapor pressure ($P_W$) determines the amount of water, which will evaporate, as stated by the Clausius-Clapeyron equation. Details of one such calculation are set out in Example 2. Because the vapor pressure is generated by the evaporated water from the droplets, it thus humidifies and saturates the air in the flowchannel. Consequently, if only a small fraction of the aggregate droplet volume is sufficient to establish the equilibrium vapor pressure, then the remaining water volume will be preserved on the surface as droplets. In this way, the humidified air provides a gas-phase seal as shown in FIG. 3 (shown by the dotted filling surrounding the microdroplets).

By selecting, for example, a particular height, h, for a certain volume of solution, the amount of evaporated water can be held at about 5%, as shown in FIG. 11B.

The process by which a gas-phase seal is established is shown on a micrograph in FIG. 4. Here, a plug of water is actuated from one end of the flowchannel to the other, leaving behind well-defined micron-sized aqueous droplets. The receding water-front can be seen on the left side of the micrograph, and the array of droplets can be seen to the right of the water-front. The black arrow indicates the direction in which the liquid is being actuated.

APPLICATIONS

The invention described here has many possible applications, which are known to those skilled in the art, e.g. see Witters et al. in Digital Biology and Chemistry (DOI: 10.1039/C4LC00248B, (Frontier) Lab on a Chip, 2014, 14, pp. 3225-3232). These include a class of assays, which we term single enzyme-linked molecular analysis (SELMA). SELMA-based assays rely on manipulation and detection of single peptide, protein and/or oligonucleotide molecules.

In one aspect, the flow system as disclosed herein may be used in a method of digital counting of at least one or more distinct analyte types.

A SELMA-based measurement is a digital counting assay in which the analytes become immobilized inside gas phase sealed droplets, and where the analytes subsequently in one or more steps undergo labeling with an enzyme-conjugated agent. Due to the nano-to-attoliter volume of the droplets, a single enzyme is able to produce a detectable optical signal within seconds-to-minutes by continuous enzymatic conversion of a detection agent. In FIG. 9 a sketch on an exemplary SELMA-based measurement is provided and in Example 4 an experimental demonstration of SELMA is described.

In one aspect disclosed herein is a method for digital counting of at least one or more distinct analyte types, the method comprising counting the analyte types contained in a plurality of liquid nano-to-attoliter droplets under a gas phase seal.

In an embodiment as disclosed herein, the gas phase seal establishes a vapor pressure within the flow compartment capable of reducing evaporation of the microdroplets.

In an embodiment as disclosed herein, the digital counting is performed in a flow system, which flow system comprises a support having a pattern of hydrophilic features in or on a hydrophobic substrate, the hydrophobic substrate being embedded in a flow compartment comprising at least one opening, the hydrophilic features configured to support the plurality of liquid nano-to-attoliter droplets.

In an embodiment as disclosed herein, the hydrophilic features are circular having a radius ($R_D$), and where the maximum droplet volume ($V_D$) a single hydrophilic circle can support is $$V_D = \pi R_D^3 G(\gamma)$$

$$G(\gamma) = \frac{2 - 3\sin\left(\frac{\pi}{2} - \gamma\right) + \sin^3\left(\frac{\pi}{2} - \gamma\right)}{3\cos^3\left(\frac{\pi}{2} - \gamma\right)}$$

where $\gamma$ is the liquid contact angle on the hydrophobic substrate.

In an embodiment as disclosed herein, the gas phase seal reduces evaporation of each nano-to-attoliter droplet to less than 50 percent of the maximum droplet volume.

In an embodiment as disclosed herein, the flow system as described herein is used in the method disclosed herein.

In an embodiment as disclosed herein, the method further comprises the step of (i) contacting a pattern of hydrophilic features in or on a hydrophobic substrate with a sample containing the one or more analyte types.

In an embodiment as disclosed herein, the method further comprises the step of (ii) capturing at least one analyte type on the hydrophilic features.

A great number of analyte types may become captured on hydrophilic features, which have undergone (bio)chemical functionalization as previously described in more detail. For example, to specifically capture oligonucleotide-based analytes such as RNA, mRNA, viral RNA, DNA, viral DNA, bacterial DNA, DNA/RNA-complexes or protein/DNA/RNA-complexes, it may be necessary to apply oligonucleotide-based capture probes displaying complementary oligonucleotide sequences to those of the analyte. To specifically capture protein- or peptide-based analytes or complexes thereof, it may be necessary to apply antibody- or aptamer-based capture probes, which specifically recognize the tertiary structure of the analyte, i.e. an antigen/antibody association. Analytes comprising entire biological entities or macro-molecular assemblies such as cells, bacteria, virus, virus-like particles, nanoparticles or cellular fragments may be captured in the same way by using antibodies specifically targeting antigens displayed by the analyte. Alternatively, the aforementioned analyte types may be captured without the aid of capture probes, but instead by matching the size of the micro-droplet (i.e. the $V_D$-value) to the size of the analyte, such that only one analyte may be able to reside in a droplet.

Furthermore, the capture probes may be supplemented with helper probes to mediate the capture, such that the helper probe first binds specifically to the analyte, and next binds specifically to the capture probe on the surface, thus acting as a tether, e.g. see the sketch in FIG. 9.

In addition, all of the aforementioned analyte types may become non-specifically captured on the hydrophilic features by use of heterobifunctional chemical crosslinking agents, such that one end of the crosslinking agent binds to the analyte and the other binds to the surface.

In an embodiment as disclosed herein, the method further comprises the step of (iii) labeling the at least one captured analyte type with a labeling agent specific to the analyte type to be detected.

The labeling agent may be selected in the same way as the capture probe, in order to mediate specific labeling of the analyte. For example, if the analyte is an oligonucleotide, then both the capture probe and the labeling agent may be oligonucleotides or synthetic variants thereof. In this case, the capture probe may recognize one specific sequence on the analyte and the labeling agent may recognize another specific sequence. The labeling agent may contain one module for the specific recognition of the analyte and another module for the subsequent detection of the analyte. At least three classes of labeling agents fulfill these criteria; enzyme-conjugated oligonucleotides, enzyme-conjugated proteins/peptides or enzyme-conjugated aptamers. The analyte-recognition module is provided by the oligonucleotide, the protein/peptide or the aptamer, respectively, whereas the detection module is provided by the enzyme.

In an embodiment as disclosed herein, the method further comprises the step of (iv) flowing across and withdrawing from the pattern a detection agent to produce the individual droplets in the form of nano-to-attoliter droplets.

With the formation of aqueous microdroplets containing detection reagents, it is possible to trigger signal-generation in the subset of droplets presenting both the labeling agent and the detection agent. In the case where the labeling agent comprises an enzyme, a suitable detection reagent would be any compatible enzyme substrate able to generate an optical signal in response to enzymatic processing. For example, in the case where the enzyme belongs to the class of peroxidases suitable detection agents include ABTS (2,2'-Azinobis [3-ethylbenzothiazoline-6-sulfonic acid]-diammonium salt), OPD (o-phenylenediamine dihydrochloride), TMB (3,3',5, 5'-tetramethylbenzidine), as well as the following tradename products Quantablu, QuantaRed, Amplex UltraRed or SuperSignal ELISA pico/femto. In the case, where the enzyme belongs to the class of phosphatases suitable detection agents include PNPP (p-Nitrophenyl Phosphate), 4-MUP (4-Methylumbelliferyl phosphate), BCIP/NBT (5-Bromo-4-chloro-3-indolyl phosphate/nitro blue tetrazolium), as well as the following tradename products CSPD, CPD Star or Dynalight. In the case where the enzyme belongs to the galactosidase class, suitable detection agents include FDG (Fluorescein Di-β-D-Galactopyranoside), DDAO galactoside (9H-(1,3-Dichloro-9,9-Dimethylacridin-2-One-7-yl) β-D-Galactopyranoside), MUG (4-Methylumbelliferyl β-D-Galactopyranoside), ONPG (o-nitrophenyl-β-D-galactopyranoside), Resorufin β-D-Galactopyranoside, X-gal (5-Bromo-4-Chloro-3-Indolyl β-D-Galactopyranoside), as well as the following tradename products Galacton-Star or Bluo-Gal. Furthermore, any ELISA-compatible enzyme/substrate pair may be applied.

In an embodiment as disclosed herein, the method further comprises the step of (v) counting the number of the droplets hosting both the labeling and detection reagent.

The counting of droplets exhibiting an optical signal is most conveniently executed with the aid of an imaging device, such as an optical microscope. Using microscopy, individual droplets may be imaged and their signal level evaluated from the relative intensity units of the micrograph. In the case, where the signal is chemiluminescent or fluorescent in nature, the acquired micrographs may be recorded using a fluorescence filterset. Furthermore, as shown in Example 4, fluorescence micrographs may be supplemented with brightfield micrographs acquired on the same position, such as to verify the position and appearance of the droplets and to correlate it to the position of the fluorescence signal.

In the case where the signal is colorimetric in nature, the acquired micrographs may be recorded by brightfield microscopy imaging such as to evaluate the absorbance, reflectance or transmittance of individual droplets.

In the case, where the droplet array covers a large area, such that the field-of-view of a single micrograph cannot contain it, several micrographs may be recorded at several positions in order to reconstruct a larger micrograph displaying the entire array. In order to guide the imaging reconstruction (e.g. micrograph stitching) easily recognizable micro-patterns may be incorporated on the array.

In an embodiment as disclosed herein, the method further comprises repeating steps (iii), (iv) and (v) one or more times.

In an embodiment as disclosed herein, the method further comprises repeating steps (iii), (iv) and (v) by using, instead of the first labeling agent, a second labeling agent specific to a second analyte type to be detected.

In an embodiment as disclosed herein, the method further comprises a step of deactivating the labeling agents present in the previous step before repeating steps (iii), (iv) and (v).

The ability to repeat the steps of labeling, adding detection reagents and counting the signal-positive droplets is a unique property of a SELMA measurement, which poses at least two advantages:

Firstly, by removing labeling and detection agents from a previous measurement and subsequently re-introducing them may increase the signal-to-noise ratio. This is due to the fact that labeling agents may bind non-specifically to the surface of the hydrophilic features without any analytes present. The non-specifically bound labeling agents may thus comprise a background noise in the counting measurement and hence lead to a potentially low signal-to-noise ratio. However, because the non-specific binding takes place at random positions on the array, whereas the specific binding to the analyte takes place only on the array features having an analyte present, then the two binding modes may be distinguished by a repeated measurement. In repeated measurements, a droplet only exhibiting non-specific binding may not provide a positive signal every time the measurement is repeated, whereas a droplet exhibiting specific binding may provide a positive signal each time. In this way, the background noise may be significantly reduced, thus leading to a greater measurement sensitivity.

Secondly, by removing labeling and detection agents specific to a first analyte type from a previous measurement and subsequently introducing labeling and detection agents specific to another analyte type may provide higher multiplexing capacity. In this case, each time the measurement is repeated a new set of analyte types become counted. For example, if the array is functionalized with capture probes specific to 10 different analyte types, then by repeating the measurement 10 times—each time introducing new labeling and detection agents—all 10 analytes may become quantified.

In an embodiment as disclosed herein, the labeling agent is deactivated by detachment from the surface-bound analyte and removed by flushing of the flow system.

As is known to those skilled in the art, there exists numerous approaches to deactivating molecular probes. In the case of a SELMA measurement, the most convenient approach relies on releasing the labeling agent from the analyte, while retaining the analyte bound to the capture probe. Once the labeling agent has become detached it may be removed by flushing the flow channel with a rinsing solution. Detection agents are more readily removed since they are not intended for binding to the array surface, and hence does not require a detachment step.

In an embodiment as disclosed herein, the labeling agent is detached by enzymatic cleavage.

In the case where the capture probe, the analyte and the labeling agent are oligonucleotides it is possible to specifically remove the labeling agent by exonuclease treatment. An exonuclease is an enzyme, which degrades double-stranded DNA, such as the complementary sequence between the analyte and the labeling agent. By rendering the capture probe inert to exonuclease treatment (e.g. by choosing a peptide nucleic acid, a locked nucleic acid or a chemically modified single-stranded DNA as the capture probe) only the binding between analyte and labeling agent may become disrupted.

In one embodiment, the labeling agent is detached by chemical cleavage or desorption, for example by adding or adjusting pH, ionic strength, denaturing salts or detergents.

In one embodiment, the labeling agent is detached by raising the temperature of the flow system.

In one embodiment, the labeling agent is deactivated by changing its chemical or physical state.

In an embodiment, where the analyte and the labeling agent both are oligonucleotides and bound to each other by base-pair sequence complementarity it is possible to specifically remove the labeling agent by changing the pH or the ionic strength of the solution. For example, when the pH is raised the double-stranded structure of DNA is disrupted due to deprotonation of the nucleobases. Furthermore, detachment of duplex DNA may also be achieved by decreasing the ionic strength of the solution, thus enhancing the electrostatic repulsion between the charged phosphate groups on the DNA backbone. Even further, by increasing the temperature to above the melting transition of duplex DNA may lead to separation of the labeling agent from the analyte.

In an embodiment, where the analyte and the labeling agent are protein- or peptide-based, the labeling agent may become detached by disrupting/denaturing the tertiary structure using detergents, denaturing salts or by increasing the temperature.

In one embodiment the labeling agent comprises an enzyme and the labelling agent may become deactivated by changing the state of the enzyme by chemical or biochemical modification of the active site.

Enzymes may become deactivated by disrupting the active site, such that further enzymatic processing is not possible. For example, in the case where the enzyme belongs to the class of peroxidase enzymes, the active site becomes irreversibly disrupted, when exposed to phenol solutions, see for example the work of Mao, L., Luo, S., Huang, Q. and Lu, J. in "Horseradish peroxidase inactivation: Heme destruction and influence of polyethylene glycol" published in Scientific Reports, vol. 3, article number 3126 (2013) (DOI: 10.1038/srep03126). Furthermore, in the case where the enzyme belongs to the class of phosphatase enzymes, the active site requires a zinc- and magnesium-ion complex to function. Consequently, by removal of these ions using chelating agents such as EDTA (ethylene-diamine-tetraacetic acid) may lead to irreversible inactivation of the enzyme, i.e. termination of enzyme activity, see for example the work of Ackermann, B. P. and Ahlers, J. in "Kinetics of alkaline phosphatase from pig kidney. Influence of complexing agents on stability and activity" published in Biochemical Journal, vol. 153, pp. 151-157 (1976) (DOI: 10.1042/bj1530151).

In one embodiment, the labeling agent comprises an enzyme and wherein the state of the enzyme is changed by chemical or physical disruption of the tertiary structure of the enzyme.

For example, the structure of an enzyme may be changed by increasing the temperature of the solution, by increasing or decreasing the pH, by increasing or decreasing the ionic strength of the solution, by adding detergents or by using chemical crosslinking agents to covalently modify the enzyme.

In one embodiment, the labeling agent comprises an enzyme and a specific analyte recognition moiety, and the analyte recognition moiety is chosen from the following group of molecules: oligonucleotides, proteins, peptides, aptamers, antibodies, complexes thereof or synthetic variants thereof.

In one embodiment, the sample containing the one or more analyte types in a liquid is contacted with the substrate containing the hydrophilic features by full immersion.

In one embodiment, the method further comprises removing the liquid and washing the substrate.

In one embodiment, the labeling is performed by bringing a solution containing a labelling agent for the analyte in contact with the captured analyte by full immersion.

In one embodiment, the method further comprises removing the solution containing residual labelling agents and washing the substrate.

In an embodiment disclosed herein, the substrate hosting the pattern of hydrophilic features is situated inside a flow compartment thus enabling liquid contact by pressure-driven actuation of liquid plugs from the inlet to the outlet. Different solutions containing different reagents (labeling agents, detection agents, deactivation agents, rinsing solutions) may be loaded into the liquid loading pad and actuated into the flow compartment. The liquid contact mode may be classified as (i) a flow-through contact or (ii) as an infuse-stop-withdraw contact. In a flow-through contact mode, a liquid plug is actuated across the flow compartment until the entire volume of the plug has passed through. In an infuse-stop-withdraw contact mode, a liquid plug is actuated until it fills out the entire volume of the flow compartment and then stopped. Following a certain waiting period, the plug is actuated out of the flow channel and into the liquid outlet.

The flow-through contact mode is typically suitable for reaction steps in which the reagents are in excess. The duration of such a step may be determined by the flow-rate (volume/time) and the volume of the liquid plug and may be adjusted in order to achieve the required process time. Steps such as rinsing steps, labeling steps, deactivation steps and detection steps could typically be performed in flow-through contact mode.

The infuse-stop-withdraw contact may be suitable for steps requiring longer incubation times and where the reagents are present at low concentrations. For example, the capture step in which a sample containing a low concentration of analytes is to be bound to the capture probes on the surface of the hydrophilic features. For a capture step, it may be advantageous to prolong the duration of the step in order to ensure complete capture of all analytes from the sample, i.e. a sufficient incubation time to allow for analytes to diffuse from the top to the bottom of the flow compartment, as well as sufficient time to enable successful capture at the surface. The infuse-stop-withdraw contact is equivalent to full immersion of the hydrophilic pattern in a solution.

In one embodiment, the analyte is selected from the following group of analytes: single-stranded oligonucleotides, double-stranded oligonucleotide complexes, proteins, protein/oligonucleotide complexes, protein/lipid complexes, peptides, exosomes, virus particles, virus like particles, nanoparticles, cell fragments or cells.

In one embodiment, the sample is selected from the following group of samples: blood, plasma, serum, urine, saliva, cerebrospinal fluid, tear fluid, or tissue.

In one embodiment, the sample is selected from laboratory-processed samples of the following sample group: blood, plasma, serum, urine, saliva, cerebrospinal fluid, tear fluid or tissue such as blood.

Depending on the type of sample, different kinds of analyte types may be present, and different laboratory protocols may be required in order to prepare the analytes for the measurement. For example, if the sample is a blood sample, it might be necessary to treat the blood with an anticoagulant (e.g. ethylene-diamine-tetra-acetic acid (EDTA), citrate or oxalate) to prevent clotting. Another example of laboratory processing of a blood sample could be to centrifuge or filter the blood in order to remove cells from the sample. Even another example of laboratory processing of a blood sample could be to dilute the blood or to add active components to facilitate specific extraction of the biomarker of interest. For example, DNA analytes may be purified from liquid samples using solid-phase reversible immobilization, in which the blood is mixed with crowding agents and carboxylic acid coated paramagnetic microparticles. These reaction conditions may favor the selective adsorption of DNA to the surface of the microparticles, which may then become extracted by application of a magnetic field. For other applications, it might be advantageous to subject the diluted—or otherwise processed—sample to (i) an electrophoretic step or (ii) a dialysis step to select molecules from the sample based on their charge, size and molecular weight.

In one embodiment, the one or more captured analytes become covalently crosslinked or coupled to the capture probe subsequent to capture.

It may be advantageous to establish a covalent link between the analyte and the capture probe, because it provides an essentially irreversible immobilization of the analyte to the surface. In this way, detachment of the labelling agent may be more readily achieved, because the link between analyte and labelling agent is non-covalent and thus weaker. For example, if both the capture probe and the analyte are oligonucleotides and bound together by complementary base-pairing and in addition bound together through one or more covalent linkages, and if the labeling agent is also an oligonucleotide, but only bound to the analyte by complementary base-pairing, then the labelling agent may be readily dissociated from the analyte by subjecting the complex to alkaline pH. The alkaline pH is not likely to affect a strong covalent linkage between capture probe/analyte to the same extent as the weaker base-pairing link between analyte/labelling agent.

As another example, consider that the capture probe is an antibody and the analyte is a protein or a peptide, and that a covalent link has been established between the two. If the labelling agent is antibody-based, and bound to the analyte through antibody/antigen-interactions, then it may be readily removed by adding detergents or by adding denaturants, while still retaining the covalent link between the capture probe and the analyte.

In one embodiment, the capture probe is an oligonucleotide or a synthetic oligonucleotide, the analyte is an oligonucleotide bound to the capture probe via a base-pairing to the capture probe sequence and where the covalent crosslinking is carried out by using an interstrand crosslinking agent such as platinum complexes, mitomycin C, nitrogen mustards, psoralens or aldehydes. Interstrand crosslinking agents as the ones mentioned above are capable of forming covalent bonds between nucleobases on opposing strands in duplex DNA, duplex DNA/RNA or synthetic variants thereof containing nucleobases. An interstrand covalent linkage provides enhanced stability as compared to the non-covalent interstrand base-pairing linkage, thus providing a virtually irreversible immobilization of the analyte to the capture probe and hence the hydrophilic feature.

In one embodiment, the capture probe is a protein, a peptide or synthetic variants thereof, the analyte is a protein, a peptide or complexes containing proteins or peptides, the analyte is bound to the capture probe by structural recognition of a specific region of the analyte and where the covalent crosslinking is carried out by using a chemical fixation agent such as formaldehyde, glutaraldehyde, osmium tetroxide or uranyl acetate. Chemical fixatives as the ones mentioned above are able to crosslink amino acids, thus providing covalent linkages at the contact zone between the analyte and the capture probe. This may lead to a virtually irreversible immobilization of the analyte to the capture probe and hence the hydrophilic feature.

In an embodiment of the method and the flow system described herein, the gas phase is provided by atmospheric air, and/or the capture probes are selected from the group of single-stranded DNA oligos, single-stranded locked nucleic acid oligos or single-stranded peptide nucleic acid oligos, and/or the different types of capture probes are arranged in regions, and/or the analytes are single-stranded DNA extracted from a processed blood sample, and/or the labelling agent comprises a detection modality and a recognition moiety, and/or the detection modality is an enzyme and/or the recognition moiety is selected from the group of single-stranded DNA oligo, a single-stranded locked nucleic acid oligo or a single-stranded peptide nucleic acid oligo.

In another embodiment of the method and the flow system described herein, the gas phase is provided by atmospheric air, the capture probes are selected from the group of single-stranded DNA oligos, single-stranded locked nucleic acid oligos or single-stranded peptide nucleic acid oligos, the different types of capture probes are arranged in regions, the analytes are single-stranded DNA extracted from a processed blood sample, the labelling agent comprises a detection modality and a recognition moiety, the detection modality is an enzyme and the recognition moiety is selected from the group of single-stranded DNA oligo, a single-stranded locked nucleic acid oligo or a single-stranded peptide nucleic acid oligo.

In the following, some non-limiting examples of applications are described:

Single enzyme-linked immunosorbent assays (sELISA), in which protein or peptide analytes are captured by surface-bound antibody-probes and later labeled and detected by single enzyme-conjugated detection probes.

Single oligonucleotide hybridization assays, in which oligonucleotide analytes are captured by surface-bound complementary oligonucleotide-probes and later labeled and detected by single enzyme-conjugated detection probes Another class of applications deals with manipulation and quantification of single biological entities, such as cells, cellular fragments/organelles, bacteria, virus capsids, etc. In these cases, the assay may use surface-bound capture-probes to immobilize any of the aforementioned biological entities and later apply specific detection-probes to quantify their number and kind. Alternatively, after the biological entities have been captured, they may be ruptured and their content of proteins, peptides, lipids or oligonucleotides may be captured by another set of surface-bound capture probes and later labeled and detected by single enzyme-conjugated detection probes.

Furthermore, the invention would be suitable for conducting digital polymerase chain reaction (dPCR) or variants thereof. In one embodiment of the invention, the dPCR assay detects specific oligonucleotide sequences by containing the target sequence as well as amplification reagents and detection probes within a single droplet. As the PCR takes place, the target sequence becomes amplified and thus rendered detectable by the detection probes. In another embodiment of the invention, the target oligonucleotide is first specifically captured by surface-bound probes and next amplification reagents and detection probes are supplied to the individual droplets to allow for the PCR and detection reaction to take place.

Those skilled in the art will know or be able to ascertain using no more than routine experimentation, many equivalents to the embodiments and practices described herein.

Accordingly, it will be understood that the invention is not to be limited to the embodiments disclosed herein, but is to be understood from the following claims, which are to be interpreted as broadly as allowed under the law.

FURTHER SPECIFIC EMBODIMENTS OF THE INVENTION

A process for holding microdroplets of a picoliter or less in volume in place on a substrate and in the liquid phase, comprising, placing the microdroplets within a channel having at least one opening, setting the volume of the channel to a value that establishes a vapor pressure within the channel capable of reducing evaporation of the microdroplets.

In particular, the invention relates to the following embodiments:

Embodiment 1. A flow system for digital counting of one or more analyte types in a sample comprising a support having a pattern of hydrophilic features in or on a hydrophobic substrate, the hydrophobic substrate being embedded in a flow compartment comprising at least one opening, the hydrophilic features configured to support a plurality of liquid nano-to-attoliter droplets each having a maximum droplet volume, and the flow compartment configured to support a gas phase seal reducing evaporation of each nano-to-attoliter droplet.

Embodiment 2. The flow system according to embodiment Error! Reference source not found., wherein the flow compartment has a volume ($V_C$), where the volume ($V_C$) is greater than the aggregate maximum droplet volume ($V_{DA}$) of all liquid nano-to-attoliter droplets and is less than $V_{MAX}$ calculated by the following equation:

$$V_{MAX} = V_{DA}\frac{\rho_L RT}{(1-RHI)M_W P_0}\exp\left(\frac{\Delta H_{VAP}}{R}\left(\frac{1}{T}-\frac{1}{T_0}\right)\right)$$

where $\rho_L$ is the volume density of the liquid, R is the molar gas constant, T is the temperature, RHI is the initial relative vapor saturation of the gas component of the liquid, $P_0$ is a reference vapor pressure of the liquid at a corresponding reference temperature $T_0$, $M_W$ is the molar weight of the liquid and $\Delta H_{VAP}$ is the enthalpy of evaporation of the liquid.

Embodiment 3. The flow system according to any one of embodiments 1-2, wherein the hydrophilic features are circular having a radius ($R_D$), and where the maximum droplet volume ($V_D$) a single hydrophilic circle can support is $$V_D = \pi R_D^3 G(\gamma)$$

$$G(\gamma) = \frac{2 - 3\sin\left(\frac{\pi}{2}-\gamma\right) + \sin^3\left(\frac{\pi}{2}-\gamma\right)}{3\cos^3\left(\frac{\pi}{2}-\gamma\right)}$$

where $\gamma$ is the liquid contact angle on the hydrophobic substrate.

Embodiment 4. The flow system according to any one of the preceding embodiments, wherein the evaporation of each nano-to-attoliter droplet is less than 50 percent of the maximum droplet volume, less than 40 percent, preferably less than 30 percent, preferably less than 20 percent, preferably less than 10 percent, preferably less than 5 percent, preferably less than 1 percent of the maximum droplet volume of each nano-to-attoliter droplet.

Embodiment 5. The flow system according to any one of the preceding embodiments, wherein the gas phase seal is comprised by atmospheric air, nitrogen, argon and/or helium.

Embodiment 6. The flow system according to any one of the preceding embodiments, wherein the gas phase seal is comprised by atmospheric air.

Embodiment 7. A flow system for digital counting of one or more distinct analyte types in a sample comprising a support having a pattern of hydrophilic features in or on a hydrophobic substrate, the hydrophobic substrate being embedded in a flow compartment comprising at least one opening, the hydrophilic features configured to support a plurality of liquid nano-to-attoliter droplets.

Embodiment 8. The flow system according to any one of the preceding embodiments comprising one or more flow compartments overlaying the droplet region to enable liquid contact to the hydrophilic/hydrophobic pattern.

Embodiment 9. The flow system according to any one of the preceding embodiments comprising one or more liquid loading pads for supplying the flow system with liquids and reagents.

Embodiment 10. The flow system according to any one of the preceding embodiments comprising a liquid inlet connecting the flow compartment(s) to the liquid loading pad(s).

Embodiment 11. The flow system according to any one of the preceding embodiments, where liquid is actuated across the flow channel by means of a pressure drop from the inlet to the outlet Embodiment 12. The flow system according to any one of the preceding embodiments comprising a liquid outlet connecting the flow channel to a pressure source to provide suction, and hence mediate liquid actuation through the flow channel.

Embodiment 13. The flow system according to any one of the preceding embodiments, wherein the gas phase seal is comprised by atmospheric air, nitrogen, argon and/or helium.

Embodiment 14. The flow system according to any one of the preceding embodiments, wherein the gas phase is comprised by atmospheric air.

Embodiment 15. The flow system according to any one of the preceding embodiments, comprising at least one capture probe for one or more distinct analyte types, the capture probe(s) being attached to the hydrophilic features.

Embodiment 16. The flow system according to anyone of the preceding embodiments, wherein different types of capture probe(s) are arranged in regions.

Embodiment 17. The flow system according to anyone of the preceding embodiments, wherein the support is planar.

Embodiment 18. The flow system according to any one of the preceding embodiments, wherein the hydrophilic feature(s) is planar.

Embodiment 19. The flow system according to anyone of the preceding embodiments, wherein the pattern of hydrophilic features comprises at least one region in which the hydrophilic features are arranged in an array.

Embodiment 20. The flow system according to anyone of the preceding embodiments, wherein the hydrophilic features are organized in a quadratic planar array, the features being shaped as circles having a radius ($R_D$), the array having a pitch ($\delta$) between neighboring features, where $\delta$ is at least $3R_D$, the array extending a length ($L_{AX}$) along the flow direction, the array extending a length ($L_{AY}$) perpendicular to the flow direction, the channel having a length ($L_{CX}$) along the flow direction, where $L_{CX}$ is greater than or equal to $L_{AX}$, the channel having a length ($L_{CY}$) perpendicular to the flow direction, where $L_{Cy}$ is greater than or equal to $L_{AY}$, the channel having a height (h), which is at least $2R_D$ and at most $h_{MAX}$, where $h_{MAX}$ is calculated from the following equation $$h_{MAX} = \theta_{MAX} \frac{L_{AX}L_{AY}}{L_{CX}L_{CY}\delta^2} \frac{\rho_L RT}{(1-RHI)M_W P_0} \exp\left(\frac{\Delta H_{VAP}}{R}\left(\frac{1}{T}-\frac{1}{T_0}\right)\right)\pi R_D^3 G(\gamma)$$

$$G(\gamma) = \frac{2 - 3\sin\left(\frac{\pi}{2}-\gamma\right) + \sin^3\left(\frac{\pi}{2}-\gamma\right)}{3\cos^3\left(\frac{\pi}{2}-\gamma\right)}$$

where $\gamma$ is the liquid contact angle for the hydrophobic material, $\theta_{MAX}$ is the maximum acceptable evaporated volume fraction of the droplets, $\rho_L$ is the volume density of the liquid, R is the molar gas constant, T is the temperature, RHI is the initial relative vapor saturation of the gas component of the liquid, $P_0$ is a reference vapor pressure of the liquid at a corresponding reference temperature $T_0$, $M_W$ is the molar weight of the liquid and $\Delta H_{VAP}$ is the enthalpy of evaporation of the liquid.

Embodiment 21. The flow system according to anyone of the preceding embodiments, wherein the pattern of hydrophilic features comprises at least two regions, and where the array of one region differs from the array of another region.

Embodiment 22. The flow system according to anyone of the preceding embodiments, wherein the region supporting the hydrophilic features is located centrally within the flow compartment.

Embodiment 23. The flow system according to anyone of the preceding embodiments, wherein the number of hydrophilic features is at least 1,000, preferably at least 10,000, preferably at least 100,000, preferably at least 1,000,000, preferably at least 10,000,000.

Embodiment 24. The flow system according to anyone of the preceding embodiments, wherein the flow compartment is channel shaped and forms a flow direction between two openings in opposite ends of the compartment.

Embodiment 25. The flow system according to embodiment 13, wherein the flow compartment and the openings have a rectangular shape in a cross section perpendicular to the flow direction.

Embodiment 26. The flow system according to embodiment 13, wherein the flow compartment has a rectangular shape and the openings have a circular shape in a cross section perpendicular to the flow direction.

Embodiment 27. The flow system according to anyone of the preceding embodiments, wherein the hydrophilic features is configured to support the nano-to-attoliter droplets and where the liquid exhibits a contact angle on the hydrophobic substrate of at least 90 degrees and at most 150 degrees.

Embodiment 28. The flow system according to anyone of the preceding embodiments, wherein the hydrophilic features is configured to support the nano-to-attoliter droplets having a radius of at least 0.1 µm and at most 100 µm.

Embodiment 29. The flow system according to anyone of the preceding embodiments, wherein the hydrophilic substrate is glass, a hydrophilic polymer or a metaloxide compound.

Embodiment 30. The flow system according to anyone of the preceding embodiments, wherein the hydrophobic layer is a molecular monolayer covalently grafted to the substrate.

Embodiment 31. The flow system according to anyone of the preceding embodiments, wherein the hydrophobic layer is a molecular monolayer chemisorbed on a metal substrate.

Embodiment 32. The flow system according to anyone of the preceding embodiments, wherein the one or more captured analytes become covalently crosslinked or coupled to the capture probe subsequent to capture.

Embodiment 33. The flow system according to anyone of the preceding embodiments, wherein the capture probe is an oligonucleotide or a synthetic oligonucleotide, the analyte is an oligonucleotide or a molecular complex containing oligonucleotides, where the analyte is bound to the capture probe via a sequence complementary to the capture probe sequence and where the covalent crosslinking is carried out by using an interstrand crosslinking agent such as platinum complexes, mitomycin C, nitrogen mustards, psoralens or aldehydes.

Embodiment 34. The flow system according to anyone of the preceding embodiments, wherein the capture probe is a protein, a peptide or synthetic variants thereof, the analyte is a protein, a peptide or complexes containing proteins or peptides, the analyte is bound to the capture probe by structural recognition of a specific region of the analyte and where the covalent crosslinking is carried out by using a chemical fixation agent such as formaldehyde, glutaraldehyde, osmium tetroxide or uranyl acetate.

Embodiment 35. The flow system according to anyone of the preceding embodiments, wherein the digital counting is a digital counting measurement.

Embodiment 36. The flow system according to anyone of the preceding embodiments, wherein the digital counting measurement is a single-enzyme linked molecular analysis (SELMA), digital polymerase chain reaction (dPCR), single enzyme-linked immunosorbent assay (sELISA) or digital single-enzyme linked immunosorbent assay (dELISA).

Embodiment 37. A method of preparing a flow system as defined in any one of the preceding embodiments.

Embodiment 38. A method of using a flow system as defined in any one of the preceding embodiments for digital counting of at least one or more distinct analyte types.

Embodiment 39. A method for digital counting of at least one or more distinct analyte types, the method comprising counting the analyte types contained in a plurality of liquid nano-to-attoliter droplets under a gas phase seal.

Embodiment 40. The method according to embodiment 39, wherein the gas phase seal establishes a vapor pressure within the flow system capable of reducing evaporation of the microdroplets.

Embodiment 41. The method according to any one of embodiments 39-40, wherein the digital counting is performed in a flow system, which flow system comprises a support having a pattern of hydrophilic features in or on a hydrophobic substrate, the hydrophobic substrate being embedded in a flow compartment comprising at least one opening, the hydrophilic features configured to support the plurality of liquid nano-to-attoliter droplets.

Embodiment 42. The method according to any one of embodiments 39-41, wherein the hydrophilic features are circular having a radius ($R_D$), and where the maximum droplet volume ($V_D$) a single hydrophilic circle can support is $$V_D = \pi R_D^3 G(\gamma)$$

$$G(\gamma) = \frac{2 - 3\sin\left(\frac{\pi}{2} - \gamma\right) + \sin^3\left(\frac{\pi}{2} - \gamma\right)}{3\cos^3\left(\frac{\pi}{2} - \gamma\right)}$$

where $\gamma$ is the liquid contact angle on the hydrophobic substrate.

Embodiment 43. The method according to any one of embodiments 39-42, wherein the gas phase seal reduces evaporation of each nano-to-attoliter droplet to less than 50 percent of the maximum droplet volume.

Embodiment 44. The method according to any one of embodiments 39-43, wherein the flow system is as defined in any one of embodiments 1-36.

Embodiment 45. The method according to any one of embodiments 39-44, further comprising the step of (i) contacting a pattern of hydrophilic features in or on a hydrophobic substrate with a sample containing the one or more analyte types.

Embodiment 46. The method according to any one of embodiments 39-45, comprising the step of (ii) capturing at least one analyte type on the hydrophilic features.

Embodiment 47. The method according to any one of embodiments 39-46, comprising the step of (iii) labeling the at least one captured analyte type with a labeling agent specific to the analyte type to be detected.

Embodiment 48. The method according to any one of embodiments 39-47, comprising the step of (iv) flowing across and withdrawing from the pattern a detection agent to produce the individual droplets in the form of nano-to-attoliter droplets.

Embodiment 49. The method according to any one of embodiments 39-48, comprising the step of (v) counting the number of the droplets hosting both the labeling and detection agent.

Embodiment 50. The method according to any one of embodiments 39-49, comprising repeating steps (iii), (iv) and (v) one or more times.

Embodiment 51. The method according to any one of embodiments 39-50, comprising repeating steps (iii), (iv) and (v) by using, instead of the first labeling agent, a second labeling agent specific to a second analyte type to be detected.

Embodiment 52. The method according to any one of embodiments 39-51, comprising a step of deactivating the labeling agents present in the previous step before repeating steps (iii), (iv) and (v).

Embodiment 53. The method according to any one of embodiments 39-52, wherein the labeling agent is deactivated by detachment from the surface-bound analyte and removed by flushing of the flow system.

Embodiment 54. The method according to any one of embodiments 39-53, wherein the labeling agent is detached by enzymatic cleavage.

Embodiment 55. The method according to any one of embodiments 39-54, wherein the labeling agent is detached by chemical cleavage or desorption by adjusting the pH, adjusting the ionic strength, adding denaturing salts or adding detergents.

Embodiment 56. The method according to any one of embodiments 39-55, wherein the labeling agent is detached by raising the temperature of the flow system.

Embodiment 57. The method according to any one of embodiments 39-56, wherein the labeling agent is deactivated by changing its chemical or physical state.

Embodiment 58. The method according to any one of embodiments 39-57, wherein the labeling agent comprises an enzyme and wherein the state of the enzyme is changed by chemical or biochemical modification of the active site.

Embodiment 59. The method according to any one of embodiments 39-58, wherein the labeling agent comprises an enzyme and wherein the state of the enzyme is changed by chemical or physical disruption of the tertiary structure of the enzyme.

Embodiment 60. The method according to any one of embodiments 39-59, wherein the labeling agent comprises an enzyme and a specific analyte recognition moiety, and the analyte recognition moiety is chosen from the following group of molecules: oligonucleotides, proteins, peptides, aptamers, antibodies, complexes thereof or synthetic variants thereof.

Embodiment 61. The method according to any one of embodiments 39-60, wherein one or more capture probes for one or more distinct analyte types are attached to the hydrophilic features.

Embodiment 62. The method according to any one of embodiments 39-61, wherein one or more capture probes for one or more distinct analyte types are attached to the hydrophilic features by a linker moiety, the linker moiety being chosen from the following group of molecules: poly (ethylene glycols), linear or branched alkanes, peptides, oligonucleotides or synthetic variants thereof.

Embodiment 63. The method according to any one of embodiments 39-62, comprising more than one type of capture probe attached to the hydrophilic features, and wherein the different types of capture probes are arranged in the regions.

Embodiment 64. The method according to any one of embodiments 39-63, wherein the capture probes are selected from the following group of probes: oligonucleotides, proteins, peptides or synthetic variants thereof.

Embodiment 65. The method according to any one of embodiments 39-64, wherein the sample containing the one or more analyte types in a liquid is contacted with the substrate containing the hydrophilic features by full immersion.

Embodiment 66. The method according to any one of embodiments 39-65, comprising removing the liquid and washing the substrate.

Embodiment 67. The method according to any one of embodiments 39-66, wherein the labeling is performed by bringing a solution containing a labelling agent for the analyte in contact with the captured analyte by full immersion.

Embodiment 68. The method according to any one of embodiments 39-67, comprising removing the solution containing residual probes and washing the substrate.

Embodiment 69. The method according to any one of embodiments 39-68, wherein the liquid is actuated across the flow channel by means of a pressure drop from the inlet to the outlet.

Embodiment 70. The method according to any one of embodiments 39-69, wherein the analyte is selected from the following group of analytes: single-stranded oligonucleotides, double-stranded oligonucleotide complexes, proteins, protein/oligonucleotide complexes, protein/lipid complexes, peptides, exosomes, virus particles, virus like particles, nanoparticles, cell fragments or cells.

Embodiment 71. The method according to any one of embodiments 39-70, wherein the sample is selected from the following group of samples: blood, plasma, serum, urine, saliva, cerebrospinal fluid, tear fluid, or tissue.

Embodiment 72. The method according to any one of embodiments 39-71, wherein the sample is selected from laboratory-processed samples of the following sample group: blood, plasma, serum, urine, saliva, cerebrospinal fluid, tear fluid or tissue such as a processed blood sample.

Embodiment 73. The method according to any one of embodiments 39-72, wherein the one or more captured analytes become covalently crosslinked or coupled to the capture probe subsequent to capture.

Embodiment 74. The method according to any one of embodiments 39-73, wherein the capture probe is an oligonucleotide or a synthetic oligonucleotide, the analyte is an oligonucleotide bound to the capture probe via a sequence complementary to the capture probe sequence and where the covalent crosslinking is carried out by using an interstrand crosslinking agent such as platinum complexes, mitomycin C, nitrogen mustards, psoralens or aldehydes.

Embodiment 75. The method according to any one of embodiments 39-74, wherein the capture probe is a protein, a peptide or synthetic variants thereof, the analyte is a protein, a peptide or complexes containing proteins or peptides, the analyte is bound to the capture probe by structural recognition of a specific region of the analyte and where the covalent crosslinking is carried out by using a chemical fixation agent such as formaldehyde, glutaraldehyde, osmium tetroxide or uranyl acetate.

Embodiment 76. The method according to any one of embodiments 39-75, wherein the digital counting is a digital counting measurement.

Embodiment 77. The method according to any one of embodiments 39-76, wherein the digital counting measurement is a single-enzyme linked molecular analysis (SELMA), digital polymerase chain reaction (dPCR), single enzyme-linked immunosorbent assay (sELISA) or digital single-enzyme linked immunosorbent assay (dELISA).

Embodiment 78. The flow system according to any one of embodiments 1-38, wherein the gas phase is provided by atmospheric air, and/or wherein the capture probes are selected from the group of single-stranded DNA oligos, single-stranded locked nucleic acid oligos or single-stranded peptide nucleic acid oligos, and/or where different types of capture probes are arranged in regions, and/or where the analytes are single- or double-stranded DNA extracted from a processed blood sample, and/or where the labelling agent comprises a detection modality and a recognition moiety, and/or where the detection modality is an enzyme and/or the recognition moiety is selected from the group of single-stranded DNA oligo, a single-stranded locked nucleic acid oligo or a single-stranded peptide nucleic acid oligo.

Embodiment 79. The method according to any one of embodiments 39-77, wherein the gas phase is provided by atmospheric air, and/or wherein the capture probes are selected from the group of single-stranded DNA oligos, single-stranded locked nucleic acid oligos or single-stranded peptide nucleic acid oligos, and/or where different types of capture probes are arranged in regions, and/or where the analytes are single- or double-stranded DNA extracted from a processed blood sample, and/or where the labelling agent comprises a detection modality and a recognition moiety, and/or where the detection modality is an enzyme and/or the recognition moiety is selected from the group of single-stranded DNA oligo, a single-stranded locked nucleic acid oligo or a single-stranded peptide nucleic acid oligo.

Embodiment 80. Use of a plurality of liquid nano-to-attoliter droplets under a gas phase seal for digital counting of at least one or more distinct analyte types.

Embodiment 81. The use according to embodiment 80, which is carried out by the method according to any one of the embodiments 39-77 and 79.

Embodiment 82. The use according to any one of embodiments 80-81, which is carried in a flow system according to any one of the embodiments 1-38 and 78.

In the following, some non-limiting examples of applications are described:

EXAMPLE 1: FORMATION AND PRESERVATION OF A FEMTOLITER AQUEOUS MICRODROPLET ARRAY

To form stable microdroplets, a regular quadratic array of hydrophilic circular features embedded on a planar hydrophobic region was contacted with a phosphate buffered aqueous solution. A 10 µl plug of the solution was actuated across the surface of the array, thus leaving microdroplets behind on the hydrophilic features as shown on the micrograph in FIG. 4.

The flow system was defined by two openings at each end of a rectangular channel to guide the liquid. The width of the channel was 3 mm, the length was 16 mm and the height was 150 µm. The array was placed centrally in the channel, with a width of 2.9 mm, a length of 14 mm and comprised a total of 406,000 hydrophilic features. The diameter of the hydrophilic circles was 5 µm, and the intercircle spacing was 10 µm. The contact angle of the aqueous solution on the hydrophobic surface was approx. 110 degrees and the experiment was conducted at ambient temperature of 21° C. At most 3% of the droplet volume was allowed to evaporate, which according to Eqn. 11 implies a maximum height of the channel of approx. 680 µm for dry air (RHI=0). Because the height of the flow compartment was only 150 µm and hence less than the maximum height, the gas phase seal was functional and was able to keep the microdroplets intact.

The array was contacted with the bulk aqueous solution by placing a 10-µl volume into a loading pad connected to the channel inlet. Next, at the channel outlet a negative pressure was applied, thus actuating the 10-µl liquid plug across the channel at a flowrate of 5 µl/min. Once the receding edge of the bulk liquid had reached the channel outlet, the pressure was terminated and a new liquid plug placed on the loading pad. Due to the functional gas phase seal, the droplets formed on top of the hydrophilic features remained stable for more than one hour, without experiencing any significant evaporation, see for example FIG. 12C.

EXAMPLE 2: HOW TO RENDER AN ARRAY OF AQUEOUS MICRO-DROPLETS EVAPORATION-RESISTANT BY OPTIMIZING FLOWCHANNEL-, DROPLET- AND ARRAY-GEOMETRY

Consider a flow channel in which a chemically patterned solid substrate has been embedded. The chemical pattern consists of circular hydrophilic regions organized into an array. The hydrophilic array is surrounded by a continuous hydrophobic region. In this way, an array of microdroplets is formed on top of the hydrophilic features once an aqueous solution is infused and subsequently withdrawn from the flowchannel, as illustrated in Example 1.

The dimensions of the flow channel are defined on FIG. 13, and are characterized by h, which is the height of the channel, $I_A$, which is the length of the flowchannel covered by the array, $I_E$, which is the length of the excess part of the channel leading to the inlet/outlet, but not hosting the array. The parameters defining the array are the droplet radius $R_D$, defined as the radius of the hydrophilic feature on the solid substrate and $\delta$ which is the center-to-center distance between neighboring droplets. In the following we will assume an array organized in a tetragonal pattern, however solutions for other array patterns may be derived using the same principles as shown below.

First, we will calculate the total molar amount of water present in the flow channel. This is done by calculating the volume of a droplet ($V_D$) and multiplying it with the total number of droplets present. We will assume that a droplet can be represented by a hemi-sphere exhibiting half the volume of a sphere. Because the array and flow channel is identical along the y-direction, we only need to consider a one-dimensional array (as the one sketched) comprised of a single line of droplets, as well as a pseudo one-dimensional flowchannel with a width of the interdroplet spacing $\delta$. The total number of droplets ($N_D$) along the one-dimensional array is then $$N_D = l_A/\delta \qquad \text{Eqn. 12}$$

The total molar amount ($n_{TOT}$) of all the droplets can now be evaluated as $$n_{TOT} = \frac{m_W}{M_W} = \frac{N_D V_D \rho_W}{M_W} = \frac{l_A}{\delta} \frac{2\pi R_D^3 \rho_W}{3 M_W} \qquad \text{Eqn. 13}$$

Here, $m_w$ is the total mass of all the droplets, $M_W$ is the molar weight of water (18.016 g/mol) and $\rho_w$ is the density of water (1000 g/l). To calculate how much of the water that is going to evaporate at a given temperature, we need to utilize the Clausius-Clapeyron equation to calculate the equilibrium vapor pressure of water ($P_W$):

$$P_W = P_0 \exp\left(\frac{\Delta H_{VAP}}{R}\left(\frac{1}{T_0} - \frac{1}{T}\right)\right) \qquad \text{Eqn. 14}$$

Here, $P_0$ is a reference equilibrium vapor pressure at the reference temperature $T_0$, T is the reaction temperature, R is the gas-constant (8.31 J·mol$^{-1}$·K$^{-1}$) and $\Delta H_{VAP}$ (40.65 kJ·mol$^{-1}$) is the enthalpy change upon evaporation of water. Suitable values for Po and To could be 2.34 kPa at a temperature of 293 K, respectively. For a closed flow channel having a volume of $V_F$, the vapor pressure of water indicates how much water can be transferred into the air as water vapor. The molar amount of water vapor at equilibrium ($n_{EVAP}$) follows from the ideal gas law as $$n_{EVAP} = \frac{P_W}{RT} V_F = \frac{P_0}{RT} \exp\left(\frac{\Delta H_{VAP}}{R}\left(\frac{1}{T_0} - \frac{1}{T}\right)\right)(2l_E + l_A)h\delta \qquad \text{Eqn. 15}$$

The fraction of evaporated water ($\theta_W$) may now be evaluated as the ratio of evaporated water to the total molar amount of water.

$$\theta_W = \frac{n_{EVAP}}{n_{TOT}} = \frac{P_0}{RT}\exp\left(\frac{\Delta H_{VAP}}{R}\left(\frac{1}{T_0} - \frac{1}{T}\right)\right)(2l_E + l_A)h\delta \frac{3M_W\delta}{2\pi l_A R_D^3} = \qquad \text{Eqn. 16}$$

-continued
$$\frac{3hP_0 M_W}{2\pi RT\rho_W}\exp\left(\frac{\Delta H_{VAP}}{R}\left(\frac{1}{T_0} - \frac{1}{T}\right)\right)\frac{\delta^2}{R_D^3}\left(2\frac{l_E}{l_A} + 1\right)$$

We will now introduce (i) the dimensionless scaling factor $N=\delta/R_D$, which is a geometrical parameter characterizing the array (i.e. greater N-values leads to a more scarcely populated array), and (ii) the dimensionless scaling factor $\varphi=l_E/l_A$, which is a geometrical parameter characterizing the flow channel design (i.e. a large $\varphi$-value indicates that the array occupies only a small part of the flow channel). Using this notation, Eqn. 16 may be rewritten as $$\theta_W = \frac{3hP_0 M_W}{2\pi RT\rho_W}\frac{1}{R_D}\exp\left(\frac{\Delta H_{VAP}}{R}\left(\frac{1}{T_0} - \frac{1}{T}\right)\right)N^2(2\varphi + 1) \qquad \text{Eqn. 17}$$

Eqn. 17 may be rearranged such that if a desired maximum evaporated fraction ($\theta_{MAX}$) is chosen, then the corresponding maximum height ($h_{MAX}$) can be evaluated:

$$h_{MAX} = \frac{2\pi RT\rho_W}{3P_0 M_W}\exp\left(\frac{\Delta H_{VAP}}{R}\left(\frac{1}{T} - \frac{1}{T_0}\right)\right)\frac{R_D}{N^2(2\varphi + 1)}\theta_{MAX} \qquad \text{Eqn. 18}$$

In FIG. 11, Eqn. 17 and Eqn. 18 are plotted for various flow channel/droplet/array geometries and temperatures. Further in FIG. 12, the experimental demonstration of droplet stability as a function of temperature and flowchannel geometry has been shown. For a flowchannel optimized for droplet preservation (FIG. 12C), the droplet array remains stable for at range of temperatures (25-45° C., as demonstrated here) and for an extended period of time of at least 1.5 hours. In principle, once thermodynamic equilibrium has been established, the droplet array would be stable indefinitely. However, in reality the flowchannel/array cannot be perfectly sealed from the external environment and hence droplets may slowly evaporate.

EXAMPLE 3: FABRICATION OF A FLOW SYSTEM

Fabrication of a flow system took place in two main steps; one step utilizes UV photolithography and microfabrication processing to produce the patterned hydrophilic features, whereas the second step deals with integrating the hydrophilic pattern into a flow compartment exhibiting the right geometry. Below both steps will be described in more detail.

Microfabrication of a Patterned Hydrophilic Substrate

In this embodiment of the invention, the hydrophilic features were composed of quartz ($SiO_2$) and the hydrophobic region was composed of perfluorodecyltrichlorosilane (FDTS). In the first step of the fabrication process, a molecular monolayer of FDTS was deposited on the quartz wafer by molecular vapor deposition using an MVD 100 Molecular Vapor Deposition system (Applied Microstructures Inc.). The FDTS underwent covalent attachment to silanol groups on the surface of the quartz and hence produced a hydrophobic monolayer on the wafer surface.

Next, a layer of AZ5214E photoresist (Microchemicals GmbH) was deposited on top of the FDTS-treated wafer by spin-coating followed by a soft bake of the wafer at 90° C.

to evaporate excess solvents. The photoresist was exposed to UV illumination through a chromium mask using a SÜSS Mask Aligner, model MA6 (SÜSS MicroTec), followed by development of the wafer in AZ351B developer solution (Microchemicals GmbH). In this way, a connected pattern of photoresist remained on the wafer thus exposing circular holes to the FDTS monolayer below.

In the final processing step, the FDTS monolayer was selectively removed to expose the hydrophilic quartz surface beneath. This was achieved by subjecting the wafer to an oxygen-plasma for a short duration using a model 300 Plasma Processor (TePla), thus removing the FDTS monolayer, but leaving behind the thicker photoresist film. In order to remove the photoresist film, the wafer was sonicated in acetone for 10 min., thus dissolving the film and hence providing a pattern of hydrophilic quartz features surrounded by a hydrophobic FDTS molecular monolayer.

Integration of the Microfabricated Array in a Flow Channel

Prior to integration, the microstructured wafer was cut into rectangular pieces (25 mm×12 mm) to fit into the flow compartment. In the cases, where the array required further surface functionalization, the functionalization protocol was conducted prior to compartment integration, as described in Examples 4-5 below.

The flow channel and a liquid loading pad was prepared by CNC milling of a poly(methyl methacrylate) (PMMA) sheet. The flow channel had a width of 1 mm, a length of 8 mm, a height of 100 µm and a wall-thickness of 200 µm. The flow channel was terminated by an outlet connected to a peristaltic pump, which provided the suction required for liquid actuation. The liquid loading pad exhibited a volume of approximately 100 µl and was connected to the flow channel via the inlet. The flow channel, loading pad, inlet and outlet were carved out of a single 8 mm thickness PMMA slab, which will henceforth be referred to as the PMMA flow structure.

To attach a rectangular wafer-piece (chip) hosting the microfabricated array of hydrophilic features to the PMMA flow structure, a piece of double-sided pressure-sensitive adhesive film (ARcare 90106, Adhesives Research, Inc.) with a nominal thickness of 142 µm was cut with a $CO_2$ laser instrument. The geometry of the laser-cut adhesive film was matched to that of the PMMA flow structure, but slightly smaller, such that the flow channel was surrounded by—but not in contact with—the adhesive. Next, the adhesive was attached to the bottom side of the PMMA flow structure, followed by placing the array chip on top of the adhesive. The assembly—PMMA flow structure, adhesive and array chip—was then sandwiched between two flat 5 mm thickness PMMA sheets and placed in a bonding press. The sandwich was clamped at a pressure of 6 kN for 60 sec. at 40° C. In this way, the adhesive was compressed to a thickness of 100 µm as defined by the height of the flow channel. The resulting bonded assembly defined a functional flow system.

EXAMPLE 4: DIGITAL COUNTING OF SINGLE DNA MOLECULES

In this example, it is shown how single biomolecules—in this case single stranded DNA—can be detected and digitally counted by use of a flow system with an integrated droplet array chip. The flow system assembly was produced and operated according to the procedures described in Examples 1-3, but prior to integration of the droplet array chip into the PMMA flow structure, the chip was subjected to further surface functionalization to allow for specific capture of the single stranded target DNA. The microfabricated chip consisted of 93,750 circular hydrophilic features having diameters of 4 µm and arranged in a square array with an inter-feature spacing of 8 µm.

Surface Functionalization Protocol

The droplet array chips were cleaned thoroughly by 10 min. sonication in acetone followed by 10 min. sonication in isopropanol followed by 10 min. sonication in ethanol. The chips were dried under a nitrogen flow and immersed in a solution of 1% (v/v) epoxysilane (Dynasylan GLYEO, Evonik Industries) solution in 95% (v/v) ethanol. The chips were incubated for 30 min. in the epoxysilane solution, and was subsequently washed three times with 95% ethanol, dried under a nitrogen flow and cured at 110° C. for 30 min.

Next, epoxy-groups on the silanized chips were reacted with amine groups present on poly(ethylene glycol) moieties. The poly(ethylene glycol) consisted of a mixture of methoxy-poly(ethylene glycol)$_{2000}$-amine (OH-PEG$_{2000}$-NH$_2$) (Jenkem Technology) and carboxylic acid-poly(ethylene glycol)$_{2000}$-amine (COOH-PEG$_{2000}$-NH$_2$) (Jenkem Technology). The mixture had a 10:1 molar ratio of OH-PEG$_{2000}$-NH$_2$ to COOH-PEG$_{2000}$-NH$_2$ and a nominal total concentration of 100 g/l in 10 mM phosphate buffered saline (PBS), 138 mM NaCl, 2.7 mM KCl, 1.5 M ammonium-sulphate, pH 7.4. The chips were incubated with the mixture for 20 hours at 40° C. Subsequently, the chips were washed three times with Milli-Q water (Millipore Corp.) and dried under a nitrogen flow.

In the last surface modification step, the chips were functionalized with a capture probe specific to the DNA target. The capture probe was a 14-mer peptide nucleic acid (PNA) with a lysine group at the N-terminal, which was used for attachment to the carboxylic acid-group on the surface grafted COOH-PEG$_{2000}$-NH$_2$. The sequence of the PNA probe from N-terminal to C-terminal was K-O-ACA TAG TTG ACA CG-OO (SEQ ID NO: 1: ACA TAG TTG ACA CG) (Panagene), where K represents a lysine group, O represents an ethylene glycol linker and the letters G, C, A and T represent PNA analogues of the DNA nucleobases.

First, the surface of the chips were prepared for reaction to the PNA probe by immersing them in a mixture of N-hydroxysuccinimide and N-(3-dimethylaminopropyl)-N'-ethylcarbodiimide hydrochloride at a molar ratio of 1:1 and at a nominal concentration of 25 g/l for each of the compounds in 100 mM 2-(N-morpholino)ethanesulfonic (MES) buffer. The chips were incubated in the mixture for 30 min. at 4° C. followed by a brief flushing in 100 mM MES buffer. Next, the chips were immersed in a 100 nM solution of the PNA probe in 100 mM MES buffer and incubated for 30 min. at ambient temperature. Subsequently, the chips were flushed briefly with 100 mM MES buffer followed by immersion in 50 mM tris(hydroxymethyl)aminomethane for 10 min. The chips were flushed with Milli-Q water three times, dried under a nitrogen flow and stored in a vacuum desiccator until they were bonded to the PMMA flow structure, as outlined in example 3.

Detection Protocol

The target for detection was a 50-bp DNA oligo (5'- TCT GTC GTA GGC ACA GAG CGG TCT TAC GGC CAG TCG CGT GTC AAC TAT GT-3' (SEQ ID NO: 2)). The last 14 basepairs of the DNA oligo were complementary to the PNA capture probe, whereas the first 12 basepairs of the DNA oligo were complementary to a DNA-based labelling agent. The labelling agent was comprised by one or more 12-bp DNA oligos conjugated to a horseradish peroxidase enzyme.

The sequence of the labeling DNA oligo was 5'- GCC TAC GAC AGA -3'-TEG-biotin (SEQ ID NO: 3 coupled to TEG-biotin), where TEG represents a tetra(ethylene glycol) linker.

The labelling agent was prepared by mixing a neutravidin-horseradish peroxidase (NAv-HRP) conjugate (Invitrogen, A2664) with the labeling oligo in a 1:3 molar ratio of NAv-HRP to oligo. The final concentration of NAv-HRP was 100 nM and the mixture was prepared in a 5X saline sodium citrate (SSC) buffer, 1.0 g/l bovine serum albumin (BSA), 0.5% (v/v) Triton X-100, pH 7.0. The mixture was incubated at 4° C. for 24 hours, thus enabling the biotinylated DNA oligos to become attached to the neutravidin moiety on NAv-HRP. The resulting conjugate exhibits an average of 3 bound DNA oligos per NAv-HRP and will be abbreviated by NAv-HRP-LO$_3$ henceforth.

The following buffers were used for the detection experiment:

Passivation Buffer: 5×SSC buffer, 0.5% (v/v) Triton X-100, 10 g/l BSA, pH 7.0.

Labeling Buffer: 5×SSC buffer, 0.5% (v/v) Triton X-100, 10 g/l BSA, pH 7.0.

Cleaning Buffer 1: 10 mM PBS, 138 mM NaCl, 2.7 mM KCl, 0.1% (v/v) Triton X-100, 50 g/l 20 kDa molar weight poly(ethylene glycol) (PEG$_{20000}$), pH 7.4.

Cleaning Buffer 2: 10 mM PBS, 138 mM NaCl, 2.7 mM KCl, 50 g/l PEG$_{20000}$, pH 7.4.

Detection Buffer: 10 mM PBS, 138 mM NaCl, 2.7 mM KCl, 10 g/l PEG$_{20000}$, 1.0 mM H$_2$O$_2$, pH 7.4.

Solutions of varying nominal DNA target concentrations (10 fM, 1 fM and 100 aM) as well as a control containing no DNA target were prepared in 5×SSC buffer, 0.5% Triton X-100, pH 7.0 immediately prior to the detection experiments. In order to conduct a detection experiment the flow system was operated in the following way:

Step 1: Actuate 25 µl of DNA target solution through the flow channel at a flowrate of 0.2 µl/min.

Step 2: Infuse the flow channel with 10 µl Passivation Buffer

Step 3: Incubate for 10 min. and actuate the solution out of the flow channel

Step 4: Infuse the flow channel with 10 µl of 50 pM NAv-HRP-LO$_3$ in Labeling Buffer Step 5: Incubate for 10 min. and actuate the solution out of the flow channel Step 6: Actuate 100 µl Cleaning Buffer 1 at a flowrate of 10 µl/min Step 7: Actuate 100 µl Cleaning Buffer 2 at a flowrate of 10 µl/min Step 8: Actuate 3 µl 200 µM ampliflu red (Sigma Aldrich, 90101-5MG-F) solution in Detection Buffer at a flowrate of 5 µl/min Briefly, the above protocol enabled the DNA target to become bound to the surface-attached PNA capture probes in step 1. Next, the captured DNA target was labelled with the NAv-HRP-LO$_3$ in steps 4-5. After removing excess labelling agents in steps 6-7, microdroplets containing the detection reagent ampliflu red was established in step 8. Ampliflu red is a fluorogenic substrate for horseradish peroxidase, which upon enzymatic processing is converted into the fluorescing compound resorufin (excitation 570 nm, emission 585 nm). Consequently, droplets hosting the labelling agent generated a fluorescence signal, which was readily detected using a fluorescence microscope.

Subsequent to step 8, the flow system was inspected under a fluorescence microscope (Zeiss Axio Vert.A1) using a 555-nm LED excitation source in combination with an appropriate fluorescence filter-set to detect the emitted signal from resorufin. Corresponding brightfield and fluorescence micrographs were recorded with a 1.4 MP CCD camera (AxioCam MR3), as shown in FIG. 14.

The fluorescence micrographs were quantified using the image analysis software ImageJ in order to count the number of fluorescing droplets. Briefly, grayscale micrographs were converted to binary format by formatting pixel values below a certain intensity threshold to 0 and pixel values above to 1. Next, connected pixel clusters of value "1" were counted. Clusters consisting of less than 4 pixels were discarded as noise. The total number of clusters for the entire array was recorded for subsequent data analysis. The same intensity threshold value was applied to all fluorescence micrographs from all detection experiments.

The results from a total of 20 detection experiments are shown on FIG. 15. The figure shows the percentwise fraction of droplets present on the array exhibiting a detectable fluorescence signal for different concentrations of DNA target. In the control sample, where no DNA target was present, still a number of droplets were detectable. This is likely due to the presence of non-specifically bound (e.g. physisorption or chemisorption) labelling agents on the array. Non-specific binding (NSB) is a common phenomenon, which is more pronounced in high-sensitive applications such as single-molecule counting. In the experiments shown here, the fraction of droplets hosting a NSB labelling agent was 0.280+/−0.097% (average +/− standard deviation from five experiments). On the other hand, samples containing target DNA was found to exhibit a higher fraction of detectable microdroplets, thus demonstrating specific detection and quantification of minute amounts of the molecular target. However, as the concentration of the target DNA increased, the number of fluorescing droplets did not increase in a directly proportional fashion. This might be due to a concentration dependent loss of target by e.g. non-specific adsorption on the other surfaces of the flowsystem, or possibly an incomplete labelling of the surface-bound DNA targets.

EXAMPLE 5: REPEATED DETECTION OF SINGLE DNA MOLECULES

In this example, it is shown how captured DNA targets may become repeatedly detected by deactivation of the labelling agents. The flow system used in this example was produced and operated according to Examples 1-3 and was functionalized according to the surface functionalization protocol provided in Example 4.

As will be illustrated below, the advantage of using repeated detection of a captured target is that each time the detection is repeated the signal-to-noise ratio is improved, and so is the limit-of-detection. Furthermore, this may enable an increased specificity in terms of discriminating between DNA targets harboring one or more single nucleotide polymorphisms (SNPs) and wildtype DNA strands without the SNPs, but otherwise identical, e.g. Example 6.

In the present example, we applied the same detection protocol as described in Example 4, but repeated the labelling and detection steps three times. Since the capture probe was based on PNA and the labelling agent was based on DNA, it was possible to selectively remove the labelling agent using T7 Exonuclease to digest the labelling agent, while keeping the capture probe/target-complex intact. Furthermore, to remove the signal from NSB labelling agents, the enzyme part of the probe was deactivated with a solution of phenol, which selectively altered the structure of the active site of the peroxidase enzyme, thus preventing it from producing a signal in the following detection assays.

The Passivation Buffer, Labeling Buffer, Cleaning Buffer 1, Cleaning Buffer 2 and Detection Buffer were the same as applied in Example 4. In addition, the following two reagents were applied:

Digestion Buffer: 1500 units/ml of T7 Exonuclease (New England Biolabs, M0263L) in 50 mM potassium acetate, 20 mM tris-acetate, 10 mM magnesium acetate, 1 mM DTT, pH 7.9

Deactivation Buffer: 5.0 mM Phenol, 1.0 mM $H_2O_2$ in 10 mM PBS, 138 mM NaCl, 2.7 mM KCl, pH 7.4

The experiment was carried out in the following way to enable three distinct detection steps of the same captured DNA targets.

Step 1: Actuate 25 µl of DNA target solution through the flow channel at a flowrate of 0.2 µl/min.

Step 2: Infuse the flow channel with 10 µl Passivation Buffer

Step 3: Incubate for 10 min. and actuate the solution out of the flow channel

Step 4: Infuse the flow channel with 10 µl of 50 pM NAv-HRP-$LO_3$ in Labeling Buffer Step 5: Incubate for 10 min. and actuate the solution out of the flow channel Step 6: Actuate 100 µl Cleaning Buffer 1 through the flow channel at a flowrate of 10 µl/min Step 7: Actuate 100 µl Cleaning Buffer 2 through the flow channel at a flowrate of 10 µl/min Step 8: Actuate 3 µl 200 µM ampliflu red (Sigma Aldrich, 90101-5MG-F) solution in Detection Buffer at a flowrate of 5 µl/min Step 9: Record fluorescence and brightfield micrographs of the droplet array Step 10: Infuse the flow channel with 10 µl Digestion Buffer Step 11: Incubate for 10 min. and actuate the solution out of the flow channel Step 12: Actuate 20 µl Deactivation Buffer through the flow channel at a flowrate of 5 µl/min Step 13: Actuate 50 µl Cleaning Buffer 1 through the flow channel at a flowrate of 10 µl/min Step 14: Repeat steps 4-13

Step 15: Repeat steps 4-9

For each sample a series of three consecutive fluorescence micrographs were recorded and analyzed using the same setup and procedures as outlined in Example 4. The first micrograph in a series correspond to the first detection step, the next micrograph in a series correspond to the second detection step and so forth. By using specific markings on the flow system surface, which were visible on the brightfield micrographs, the coordinates of the fluorescence micrographs were corrected for changes in the XY-position between detection steps. In this way, it was possible to compare the XY-positions of individual droplets for the different detection steps. Next, for each micrograph in the detection series, the XY-pixel position of droplets exhibiting a fluorescence signal was recorded and compared to the remaining two members of the series. Droplet positions which did not differ by more than 4 pixels between the detection steps were considered to be a "persistent" droplet, i.e. a droplet repeatedly producing a signal, when labelling and detection agents are added.

The results of the three detection steps are shown in FIG. 16, in which a series of fluorescence micrographs are shown for a sample containing 100 aM DNA target. On the micrographs, persistent droplets have been labeled with a circle. For the control sample, where no DNA target was added, no persistent droplets could be identified in all three detection steps.

The following table shows a quantitative comparison between the 100 aM DNA target sample and the control sample. The table in summarizes the average results from 5 identically prepared samples containing 100 aM target DNA and 5 identically prepared control samples containing no target DNA. The table provides the average positive fraction of persistent droplets (Avg.), as defined in Example 5, for the control sample (first row) and for the 100 aM target DNA sample (second row). The standard deviation (St. dev.) corresponds to the standard deviation of the 5 samples. The third row provides the signal-to-noise (S/N) ratio resulting from each subsequent detection step. The S/N-ratio is provided as the experimentally measured value supplemented in parenthesis by the theoretical value. The experimental value was obtained by dividing the average values in the second row with the average values in the first row. The theoretical value was calculated by dividing the average value for the 100 aM samples with (i) 0.28% for the first detection step, (ii) $7.84 \cdot 10^{-4}$% (0.28%·0.28%) for the second detection step and (iii) $2.2 \cdot 10^{-6}$% (0.28%·0.28%·0.28%) for the third detection step.

|  | Analysis 1 | | Analysis 2 | | Analysis 3 | |
| --- | --- | --- | --- | --- | --- | --- |
|  | Avg. | St. dev. | Avg. | St. Dev. | Avg. | St. Dev. |
| Control | 0.280% | 0.097% | $6.1 \cdot 10^{-4}$% | $9.2 \cdot 10^{-4}$% | N/A | N/A |
| 100 aM | 0.507% | 0.160% | 0.243% | 0.091% | 0.221% | 0.084% |
| S/N ratio | 1.81 (1.81) | | 398 (310) | | Inf. (100,674) | |

The percentwise fraction of persistent droplets for the control sample decreased for each repetition of the detection step, and consequently lead to an increase in the S/N-ratio. The reason for this is that in the control sample only NSB labelling agents provide the fluorescence signal. These bind in a random fashion to the array, and because their signal is deactivated between subsequent detection steps, it is unlikely that the same droplet will produce a signal in a subsequent detection step. For example—assuming a random binding pattern of NSB labelling agents—if the fraction of droplets hosting a NSB labelling agent is 0.28% in each detection step, e.g. FIG. 15D, then there is only a $2.2 \cdot 10^{-6}$% (0.28%·0.28%·0.28%) chance of observing persistent droplets in all three detection steps. For an array hosting 100,000 droplets, the false-positive detection rate of $2.2 \cdot 10^{-6}$% corresponds to only 0.002 false-positive detections. It is thus highly unlikely to observe any persistent droplets for the control sample.

Consequently, for these particular experimental settings all noise derived from NSB labelling agents can be ruled out, and hence any droplet that persists for at least three consecutive detection steps represents—with very high probability—a functionally assembled capture-probe/DNA-target/labelling-probe complex.

EXAMPLE 6: DESCRIPTION OF A FLOW SYSTEM SETUP FOR DETECTION OF SINGLE DNA MOLECULES IN A 1:10,000 (TARGET:NON-TARGET) BACKGROUND OF NON-TARGET DNA DIFFERING IN SEQUENCE FROM THE TARGET BY A SINGLE BASEPAIR

In this example, a flow system able to perform digital detection of a DNA analyte present in a 100 µl sample solution is obtained by following the steps described below. The analyte (target DNA) is expected to be present at a concentration of approx. 10 aM in the sample and contains the following sequence segment: 5'-TCT GTC GTA GGC ACA GAG CGG TCT TAC GGC CAG TCG CGT GTC AAC TAT-3' (SEQ ID NO: 4). In addition to the analyte, the sample is expected to contain another non-target DNA molecule (wildtype DNA) at a concentration approx. 10,000 times higher, i.e. 100 fM, and containing the following sequence segment: 5'-TCT GTC GTA GGC ACA GAG CGG TCT TAC GGC CAG TCG CGT GTC CAC TAT-3' (SEQ ID NO: 5). The target and the wildtype DNA differs in sequence only at the bolded and underlined position.

The capture probe is a single-stranded PNA oligo selected to be complementary to the 5'-end of the target and wildtype DNA, which can be achieved by using a capture probe containing the following sequence: 5'-GTG CCT ACG ACA GA-3' (SEQ ID NO: 6), where 5' and 3' corresponds to the N- and C-terminus of the probe, respectively. According to IDT Oligo Analyzer software (https://eu.idtdna.com/calc/analyzer), the melting temperature for the capture probe is expected to be at least 46.8° C., and hence 100% of both target and wildtype DNA will be bound at ambient temperature, i.e. 23° C. Consequently, the array needs to be designed to accommodate binding of at least 6 mio. DNA molecules, which corresponds to 100% binding of a 100 µl sample containing 100 fM DNA.

To conduct a digital counting measurement, the captured target DNA have to be labeled with a labelling agent consisting of a single-stranded DNA oligo containing the following sequence 5-ATA GTT GAC AC-3' (SEQ ID NO: 7) conjugated to an enzyme such as horseradish peroxidase, alkaline phosphatase or beta-galactosidase—all of which have fluorogenic substrates commercially available. The labelling agent exactly matches the sequence of the DNA target at the 3'-end. Under optimal binding conditions 82.6% of the target DNA will be bound to the labelling agent at a temperature of 23° C. (IDT Oligo Analyzer). However, under the same conditions 1% of the wildtype DNA will also be bound by the labelling agent due to the high sequence similarity between target and wildtype. Consequently, to conduct a digital counting measurement, the array is required to present at least 120,000 hydrophilic features. The amount of 120,000 features is chosen such that when the first labelling and the first detection steps have been conducted, then approx. half of the droplets of the array will produce a fluorescence signal, i.e. 1% of 6 mio. wildtype DNA+82.6% of 600 target DNA.

To accommodate 120,000 hydrophilic features, the features are to be shaped as circles having a diameter of 5 µm and placed in a regular quadratic array with a nearest neighbor separation of 10 µm. According to Eqn. 1 an individual hydrophilic feature may thus support an aqueous droplet having a maximum volume of $V_D$=52 femtoliter. To calculate the maximum droplet volume, a γ-value of 110° corresponding to the contact angle of water on a perfluorodecyltrichlorosilane (FDTS) support was applied. Consequently, the aggregate volume of the droplet array is $V_{DA}$=6.2 nanoliter (120,000 times 52 femtoliter). The maximum flow compartment volume is then obtained from Eqn. 9 as $V_{MAX}$=326 µl.

To calculate the maximum flow compartment volume, the following values were applied; $\rho_L$=1000 kg/m³ is the volume density of water, R=8.31 J/(mol·K) is the molar gas constant, T=296 K (23° C.) is the temperature, RHI=0 is taken as the initial relative water vapor saturation of dry atmospheric air, $P_0$=226 Pa is the vapor pressure of water vapor at temperature $T_0$=283 K (10° C.), $M_W$=18.016·10⁻³ kg/mol is the molar weight of water and $\Delta H_{VAP}$=40.65·10³ J/mol is the enthalpy of evaporation of water. The values were obtained from Lange's Handbook of Physical Chemistry (ISBN-13: 9780070163843) and from Atkin's Physical Chemistry, Volume 1: Thermodynamics and Kinetics (ISBN-13: 9780716785675).

However, in order for the droplets to (i) remain stable during the imaging detection step and (ii) provide optimal conditions for the enzymatic reaction only a small fraction of the droplet volume is allowed to evaporate. The maximum acceptable evaporated volume fraction of the droplets is thus set to 5%, i.e. $\theta_{MAX}$=0.05, hence leading to a flow compartment volume of $V_C$=16.3 µl, i.e. $V_C$=$\theta_{MAX} \cdot V_{MAX}$.

The final geometrical design of the flow compartment is obtained by choosing a rectangular channel-shape for the compartment exhibiting an aspect ratio of 10:1 and a length of $L_{CX}$=15 mm and a width of $L_{CY}$=1.5 mm. The height of the channel is thus required to be less than $h_{MAX}$=724 µm ($h_{MAX}$=$V_C/(L_{CY} \cdot L_{CX})$) in order to ensure that no more than 5% of the maximum droplet volume evaporates. The 10:1 aspect ratio may be applied to the array of hydrophilic features, such that the array will present 1,091×110 circular features, corresponding to $L_{AX}$=10.9 mm and $L_{AY}$=1.1 mm.

For the flow system setup outlined above, the DNA targets may become reliably detected in a background outnumbering the target 10,000-fold by repeating the labelling and detection steps three times, as described in Example 5. In this way, on average 60,496 DNA molecules (1% of 6 mio. wildtype DNA+82.6% of target DNA) is expected to provide a signal in the first detection step, corresponding to 60,000 false-positive detections of the wildtype DNA and 496 correct detections of target DNA.

In the second detection step, on average 1,010 DNA molecules (1% of 60,000 wildtype DNA+82.6% of 496 target DNA) is expected to provide a persistent signal, corresponding to 600 false-positive detections of wildtype DNA and 410 correct detections of target DNA. In the third detection step, on average 344 DNA molecules (1% of 600 wildtype DNA+82.6% of 410 target DNA) is expected to provide a persistent signal, corresponding to 6 false-positive detections of the wildtype DNA and 338 correct detections of target DNA.

For the third detection step, the number of correct detections is expected to surpass the number of false-positive detections by a factor of 56, thus providing an excellent quantification accuracy. However, by repeating the labelling and detection step a fourth time, the false-positive detections are expected to become completely removed.

SEQUENCE LISTING

SEQ ID NO: 1:
ACA TAG TTG ACA CG

SEQ ID NO: 2:
5'-TCT GTC GTA GGC ACA GAG CGG TCT TAC GGC CAG TCG CGT GTC AAC TAT GT-3'

SEQ ID NO. 3:
5'-GCC TAC GAC AGA-3'

SEQ ID NO: 4:
5'-TCT GTC GTA GGC ACA GAG CGG TCT TAC GGC CAG TCG CGT GTC AAC TAT-3'

SEQ ID NO: 5:
5'-TCT GTC GTA GGC ACA GAG CGG TCT TAC GGC CAG TCG CGT GTC CAC TAT-3'

SEQ ID NO: 6:
5'-GTG CCT ACG ACA GA-3'

SEQ ID NO: 7:
5'-ATA GTT GAC AC-3'

The invention claimed is:

1. A method of stabilizing a droplet pattern comprising the following steps: 1) providing a pattern of hydrophilic features in or on a hydrophobic substrate, the hydrophobic substrate being embedded in a flow compartment comprising a separate inlet and outlet, the hydrophilic features configured to support a plurality of liquid nano-to-attoliter droplets, 2) allowing a liquid to enter the inlet and exit the outlet of the flow compartment to form a plurality of liquid nano-to-attoliter droplets having an aggregate liquid volume $V_{DA}$ with a corresponding aggregate molar amount of liquid $n_{DA}$, 3) blocking the inlet and outlet to provide a closed environment in the flow compartment of volume $V_C$, 4) establishing a gas phase seal by allowing evaporation from the droplets into gas to establish a saturation vapor pressure within the closed flow compartment, wherein the vapor pressure increase at saturation is less than $n_{DA}RT/V_C$, where T is the temperature and R is the universal gas constant, such that the droplets, now having a reduced volume due to the evaporation, remain stable.

2. The method according to claim 1, wherein the gas phase seal reduces evaporation of each of a nano-to-attoliter droplet to less than 50 percent of the maximum droplet volume.

3. The method according to claim 1, comprising the step of contacting the pattern of hydrophilic features in or on a hydrophobic substrate with a sample containing one or more analyte types.

4. The method according to claim 3, comprising the step of capturing at least one analyte type on the hydrophilic features.

5. The method according to claim 4, comprising the step of labeling the at least one captured analyte type with a labeling agent specific to the analyte type to be detected.

6. The method according to claim 5, comprising the step of flowing across and withdrawing from the pattern a detection agent to produce individual droplets.

7. The method according to claim 6, comprising the step of counting the number of the droplets hosting both the labeling and detection reagent.

8. The method according to claim 7, comprising the step of counting of droplets exhibiting an optical signal using an imaging device.

9. The method according to claim 3, where the analyte is selected from the following group of analytes: single-stranded oligonucleotides, double-stranded oligonucleotide complexes, proteins, protein/oligonucleotide complexes, protein/lipid complexes, peptides, exosomes, virus particles, virus like particles, nanoparticles, cell fragments or cells.

10. The method according to claim 1, wherein the method is performed in a flow system for digital counting of one or more distinct analyte types in a sample comprising a support having the pattern of hydrophilic features in or on a hydrophobic substrate, the hydrophobic substrate being embedded in the flow compartment, the hydrophilic features configured to support a plurality of liquid nano-to-attoliter droplets.

11. The method according to claim 1, wherein the volume ($V_C$) is greater than an aggregate maximum droplet volume ($V_{DA}$) of all liquid nano-to-attoliter droplets and is less than $V_{MAX}$ calculated by the following equation:

$$V_{MAX} = V_{DA} \frac{\rho_L RT}{(1-RHI)M_w P_0} \exp\left(\frac{\Delta H_{VAP}}{R}\left(\frac{1}{T} - \frac{1}{T_0}\right)\right)$$

where $\rho_L$, is the volume density of the liquid, R is the molar gas constant, T is the temperature, RHI is the initial relative vapor saturation of the gas component of the liquid, $P_0$ is a reference vapor pressure of the liquid at a corresponding reference temperature $T_0$, $M_W$ is the molar weight of the liquid and $\Delta H_{VAP}$ is the enthalpy of evaporation of the liquid.

12. The method according to claim 1, wherein an enzymatic reaction is conducted in one or more of the droplets.

13. The method according to claim 1, wherein the droplets are in the form of nano-to-attoliter droplets.

14. The method according to claim 10, wherein the hydrophilic features contain one or more labelling agents, where the labelling agent includes an enzyme, where droplets are produced by flowing across and withdrawing from the pattern a liquid comprising a detection agent, where the detection agent is an enzyme substrate and where the produced droplets are imaged with an imaging device.

15. The method according to claim 10, where the hydrophilic features contain one or more analytes, where the analyte is a cell, a cell fragments or a virus particle, where the analytes are labelled with a labelling agent, where the labelling agent includes an enzyme, where droplets are produced by flowing across and withdrawing from the pattern a liquid comprising a detection agent, where the detection agent is an enzyme substrate and where the produced droplets are imaged with an imaging device.

16. The method according to claim 10, wherein capture probes are attached to the hydrophilic features, where the capture probes can bind to one or more analytes, where the analyte is a single- or double-stranded oligonucleotides derived from a sample, where the analyte is labelled with a labelling agent, where the labelling agent includes an enzyme, where droplets are produced by flowing across and withdrawing from the pattern a liquid comprising a detection agent, where the detection agent is an enzyme substrate and where the produced droplets are imaged with an imaging device.

17. The method according to claim 16, where the labelling agent selectively labels the analyte based on the oligonucleotide sequence.

18. The method according claim 17, wherein two labelling agents are applied, the first labelling agent includes an enzyme and an oligonucleotide having a first sequence, the second labelling agent is an oligonucleotide having a second and a third sequence, where the second sequence is complementary to the captured analytes, where the third sequence is complementary to the first sequence, such that the second labelling agent attaches to the captured analyte and the first labelling agent attaches to the second labelling agent.

19. The method according to claim 10, wherein capture probes are attached to the hydrophilic features, where the capture probes can bind to one or more analytes, where the analyte is a protein or a peptide derived from a sample, where the analyte is labelled with a labelling agent, where the labelling agent includes an enzyme, where droplets are produced by flowing across and withdrawing from the pattern a liquid comprising a detection agent, where the detection agent is an enzyme substrate and where the produced droplets are imaged with an imaging device.

20. The method according to claim 19, wherein two labelling agents are applied, the first labelling agent includes an enzyme and an oligonucleotide having a first sequence, the second labelling agent includes an oligonucleotide having a second sequence and an analyte-binding antibody or aptamer, where the second sequence is complementary to the first sequence, such that the second labelling agent attaches to the captured analyte and the first labelling agent attaches to the second labelling agent.

21. The method according to claim 1, where less than 50 percent of the droplet volume has evaporated after one minute.

22. The method according to claim 1, where less than 10 percent of the droplet volume has evaporated after at least one minute.

23. The method according to claim 1, where less than 1 percent of the droplet volume has evaporated after one minute.

* * * * *